United States Patent
Thavandiran et al.

(10) Patent No.: US 10,034,738 B2
(45) Date of Patent: Jul. 31, 2018

(54) CARDIAC TISSUE CONSTRUCTS AND METHODS OF FABRICATION THEREOF

(71) Applicant: THE GOVERNING COUNCIL OF THE UNIVERSITY OF TORONTO, Toronto (CA)

(72) Inventors: Nimalan Thavandiran, Milton (CA); Milica Radisic, Toronto (CA); Peter Zandstra, Toronto (CA)

(73) Assignee: THE GOVERNING COUNCIL OF THE UNIVERSITY OF TORONTO, Toronto, ON (CA)

( * ) Notice: Subject to any disclaimer, the term of this patent is extended or adjusted under 35 U.S.C. 154(b) by 0 days.

(21) Appl. No.: 14/650,227

(22) PCT Filed: Dec. 6, 2013

(86) PCT No.: PCT/CA2013/050940
§ 371 (c)(1),
(2) Date: Jun. 5, 2015

(87) PCT Pub. No.: WO2014/085933
PCT Pub. Date: Jun. 12, 2014

(65) Prior Publication Data
US 2015/0313704 A1 Nov. 5, 2015

Related U.S. Application Data

(60) Provisional application No. 61/843,285, filed on Jul. 5, 2013, provisional application No. 61/734,859, filed on Dec. 7, 2012.

(51) Int. Cl.
*A61F 2/02* (2006.01)
*A61L 27/24* (2006.01)
(Continued)

(52) U.S. Cl.
CPC ............. *A61F 2/02* (2013.01); *A61L 27/24* (2013.01); *A61L 27/3886* (2013.01);
(Continued)

(58) Field of Classification Search
CPC ............. A61F 2/02; A61F 2230/0002; A61F 2240/002; A61L 27/24; A61L 27/3386;
(Continued)

(56) References Cited

U.S. PATENT DOCUMENTS 6,306,646 B1 * 10/2001 Saad .................... C12M 23/00
422/547
7,338,798 B2 3/2008 Dennis et al.
(Continued)

FOREIGN PATENT DOCUMENTS

| WO | 2010129725 | 11/2010 |
| WO | 2012043820 | 5/2012 |
| WO | 2013056019 | 4/2013 |

OTHER PUBLICATIONS

Nimalan Thavandiran et al., Design and formulation of functional pluripotent stem cell-derived cardiac microtissues, PNAS, Nov. 18, 2013, 10 pages.
(Continued)

*Primary Examiner* — William H. Beisner
*Assistant Examiner* — Danielle B Henkel
(74) *Attorney, Agent, or Firm* — Lynn C. Schumacher; Hill & Schumacher

(57) ABSTRACT

Methods and devices are provided for the formation of cardiac tissue constructs. In some embodiments, methods are provided for forming cardiac tissue constructs that including cardiomyocytes, non-myocytes, and extracellular matrix, and which exhibit properties associated with healthy cardiac tissue. In some embodiments, microfabrication platforms are provided to support the transmission of dynamic
(Continued)

electromechanical forces, such that the cardiac microtissue constructs may be formed mimicking the basic microenvironment found in the heart. The microfabrication platform may include retaining features for stabilizing the position of the microtissue construct during its formation, and the microfabrication platform may include a ramped support configured to produce tissue constructs having a ring geometry. In some embodiments, the microfabrication platform may be configured to for the application of point electrical stimulation, and/or to amplify the transduction of force into a visible displacement.

29 Claims, 75 Drawing Sheets

(51) Int. Cl.
A61L 27/38 (2006.01)
C12N 5/071 (2010.01)
C12N 5/077 (2010.01)
C12M 3/00 (2006.01)
C12M 1/42 (2006.01)
C12M 1/12 (2006.01)

(52) U.S. Cl.
CPC ............ C12M 21/08 (2013.01); C12M 25/00 (2013.01); C12M 35/04 (2013.01); C12N 5/0657 (2013.01); C12N 5/0697 (2013.01); A61F 2230/0002 (2013.01); A61F 2240/002 (2013.01); A61L 2430/20 (2013.01); C12N 2506/02 (2013.01); C12N 2513/00 (2013.01); C12N 2529/00 (2013.01); C12N 2533/54 (2013.01)

(58) Field of Classification Search
CPC ... A61L 2430/20; C12M 21/08; C12M 25/00; C12M 35/04; C12N 5/0657; C12N 5/0697; C12N 250/02; C12N 2513/00; C12N 2529/00; C12N 2533/54
See application file for complete search history.

(56) References Cited

U.S. PATENT DOCUMENTS

| 7,618,452 | B2 | 11/2009 | Eschenhagen | |
| 2003/0059936 | A1* | 3/2003 | Baumann | C12M 35/02 435/325 |
| 2005/0112759 | A1 | 5/2005 | Radisic et al. | |
| 2006/0104958 | A1 | 5/2006 | Akins, Jr. | |
| 2006/0105357 | A1 | 5/2006 | Benesch et al. | |
| 2008/0038812 | A1 | 2/2008 | Elson et al. | |
| 2008/0075750 | A1 | 3/2008 | Akins, Jr. | |
| 2008/0220516 | A1 | 9/2008 | Eddington et al. | |
| 2009/0061410 | A1 | 3/2009 | Zimmermann et al. | |
| 2009/0318962 | A1 | 12/2009 | Spedden et al. | |
| 2010/0068793 | A1* | 3/2010 | Ungrin | B01L 3/5085 435/283.1 |
| 2011/0034867 | A1 | 2/2011 | Guyette et al. | |
| 2011/0171712 | A1 | 7/2011 | Rivron et al. | |
| 2012/0142556 | A1 | 6/2012 | Parker et al. | |
| 2013/0217778 | A1* | 8/2013 | Vandenburgh | A61K 31/155 514/635 |

OTHER PUBLICATIONS

Nima Badie et al., Novel Micropatterned Cardiac Cell Cultures with Realistic Ventricular Microstructure, Biophysical Journal, vol. 96, May 2009, 3873-3885.
David A. Elliot et al., NKX2-5 hESCs for isolation of human cardiac progenitors and cardiomyocytes, Nature Methods, vol. 8, No. 12, Dec. 2011, 7 pages.
Paul W. Burridge et al., Production of De Novo Cardiomyocytes: Human Pluripotent Stem Cell Differentiation and Direct Reprograming, Cell Stem Cell, Jan. 6, 2012, 19(1): 16-28.
Jianhua Zhang et al., Extracellular Matrix Promotes Highly Efficient Cardiac Differentiation of Human Pluripotent Stem Cells: The Matrix Sandwich Method, Circ Res. Oct. 12, 2012; 111(9): 1125-1136.
Chunhui Xu et al., Efficient generation and cryopreservation of cardiomyocytes derived from human embryonic stem cells, Regen Med. Jan. 2011; 6(1): 53-66.
Wei-Zhong Zhu, Methods for the Derivation and Use of Cardiomyocytes from Human Pluripotent Stem Cells, Methods Mol. Biol. 2011; 767:419-431.
Xiaojun Lian et al., Robust Cardiumyocyte Differentation from Human Pluripotent Stem Cells via Temporal Modulation of Canonical Wnt Signaling, PNAS, May 29, 2012, 10 pages.
Steven J. Kattman et al., Stage-Specific Optimization of Activin/Nodal and BMP Signaling Promotes Cardiac Differentiation of Mouse and Human Pluripotent Stem Cell Lines, Cell Stem Cell 8, 228-240, Feb. 4, 2011.
Hideki Usoaki et al., Efficient and Scalable Purification of Cardiomyocytes from Human Embryonic and Induced Pluripotent Stem Cells by VCAM1 Surface Expression, Aug. 2011, vol. 6, Issue 8, 9 pages.
Nicole C. Dubois et al., SIRPA is a specific cell-surface marker for isolating cardiomyocytes derived from human stem cells, Nature Biotechnology, vol. 29, No. 11, Nov. 2011, 9 pages.
Thomas J. Kean et al., Development of a peptide-targeted, myocardial ischemia-homing, mesenchymal stem cell, Journal of Drug Targeting, 2012: 20(1): pp. 23-32.
Daniela Panakova et al., Wnt11 patters a myocardial electrical gradient via regulation of the L-type Ca2 channel, Nature, Aug. 12, 2010; 466(7308), 874-878, 11 pages.
Hiroshi Kurazumi et al., The effects of Mechanical Stress on the Growth, Differentiation, and Paracrine Factor Production of Cardiac Stem Cells, Dec. 2011, vol. 6, Issue 12, 8 pages.
Deok-Ho Kim et al., Nanoscale cues regulate the structure and function of macroscopic cardiac tissue constructs, PNAS, Jan. 12, 2010, vol. 107, No. 2, 565-570.
Yuliang Feng et al., Recent concepts for the roles of progenitor/stem cell niche in heart repair, Am J Cardiovasc Dis 2012;2(1):75-83.
Mukesh K. Gupta et al., Combinatorial Polymer Electrospun Matrices Promote Physiologically-Relevant Cardiomyogenic Stem Cell Differentiation, Plos One, Dec. 2011, vol. 6, Issue 12, 12 pages.
Sebastian Schaaf et al., Human Engineered Heart Tissue as a Versatile Tool in Basic Research and Preclinical Toxicology, PLOS ONE, Oct. 2011, vol. 6, Issue 10, 11 pages.
Chiara Sassoli et al., Mesenchymal stromal cells affect cardiomyocyte growth through juxtacrine Notch-1/Jagged-1 signaling and paracrine mechanisms: Clues for cardiac regeneration, Journal of Molecular and Cellular Cardiology, 51 (2011) 399-408.
Nima Badie et al., Conduction block in micropatterened cardiomyocyte cultures replicating the structure of ventricular cross-sections, Cardiovascular Research (2012) 93, 263-271.
Milica Radisic et al., Functional assembly of engineered myocardium by electrical stimulation of cardiac myocytes cultured on scaffolds, PNAS, Dec. 28, 2004, vol. 101, No. 52, 18129-18134.
Vikram S. Deshpande et al., A bio-chemo-mechanical model for cell contractility, PNAS, Nov. 7, 2006, vol. 103, No. 45, 8 pages.
Vicky A. Cameron et al., Minireview: Natriuretic Peptides during Development of the Fetal Heart and Circulation, Endocrinology 144(6):2191-2194.
Celine L. Bauwens, Ph.D. et al., Geometric Control of Cardiomyogenic Induction in Human Pluripotent Stem Cells, Tissue Engineering: Part A, vol. 17, Nos. 15 and 16, 2011, 10 pages.
Wesley R. Legant et al., Microfabricated tissue gauges to measure and manipulate forces from 3D microtissues, PNAS, Jun. 23, 2009, vol. 106, No. 25, 10097-10102.
Tomoji Ishisaka et al., Muscle-Actuated Power Generator Using Cultured Cardiomyocytes and PZT Fiber, IEEE, 4 pages.

(56) References Cited

OTHER PUBLICATIONS

Xiaobo Wang et al., Cellular Dynamics International, ACEA Biosciences, and Roche Applied Sciences Cooperate to Evaluate iCell, Cardiomyocytes on the xCELLigence System, Sep. 16, 2010, 5 pages.
Vikram S. Deshpande et al., A model for the contractility of the cytoskeleton including the effects of stress-fibre formation and dissociation, The Royal Society, Sep. 21, 2012, 30 pages.
Nathaniel L. Tulloch et al., Growth of Engineered Human Myocardium with Mechanical Loading and Vascular Co-culture, Circ. Res. Jun. 24, 2011, 109(1) 47-59.
Keith Baar et al., Self-organization of rat cardiac cells into contractile 3-D cardiac tissue, FASEB Journal, 10.1096/fj.04-2034fje. Dec. 1, 2004, 21 pages.
Herman Vandenburgh et al., Automated drug screening with contractile muscle tissue engineered from dystrophic myoblasts, FASEB Journal, 0892-6638/0910023-3325, 10 pages.
Milica Radisic et al., Functional assembly of engineered myocardium by electrical stimulation of cardiac myocytes culturedon scaffolds, PNAS, Dec. 28, 2004, vol. 101, No. 52, 18129-18134.
Wolfram H. Zimmermann et al., Three-Dimensional Engineered Heart Tissue from Neonatal Rat Cardiac Myocytes, 2000 John Wiley & Sons, Inc., 9 pages.
Thomas Eschenhagen et al., Three-dimensional reconstitution of embryonic cardiomyocytes in a collagen matrix: a new heart muscle model system, 0892-6638/97/0011-0683 FSAB.
Tal Dvir et al., Nanowired three-dimensional cardiac patches, Nature Nanotechnology, vol. 6, Nov. 2011, 6 pages.
Matthew W. Curtis et al., Cardiac Tissue Engineering, Journal of Cardiovascular Nursing, vol. 24, No. 2, pp. 87-92.
Qiming Pang, Design and Development of a Biostretch Apparatus for Tissue Engineering, thesis submitted University of Toronto, 2009, 135 pages.
Jana Dengler, An In Vitro Model System for Cardiac Cell Therapy, thesis submitted University of Toronto, 2009, 71 pages.
Wolfram-Hubertus Zimmermann et al., Engineered heart tissue grafts improve systolic and diastolic function in infarcted rat hearts, Nature Medicine, vol. 12, No. 4, Apr. 2006, 7 pages.
Thomas Boudou Ph.D., et al., A Microfabricated Platform to Measure and Manipulate the Mechanics of Engineered Cardiac Microtissues, Tissue Engineering: Part A, vol. 18, Nos. 9 and 10, 2012, 10 pages.
Herman Vandenburgh, PhD., et al., Drug-Screening Platform Based on the Contractility of Tissue-Engineered Muscle, Muscle Nerve 37:438-447, 2008.
Weining Bian et al., Engineered skeletal muscle tissue networks with controllable architecture, Biomaterials, Mar. 2009; 30(7): 1401-1412.
International Search Report in PCT/CA2013/050940 dated Apr. 9, 2014.
Written Opinion in PCT/CA2013/050940 dated Apr. 9, 2014.

\* cited by examiner

| Conditions | | %NKX2.5+ | %CD90+ | Tissue composition |
|---|---|---|---|---|
| CMW A | Cardiac microwire | 100 | 0 | |
| CMW B | Cardiac microwire | 75 | 25 | |
| CMW C | Cardiac microwire | 50 | 50 | |
| CMW D | Cardiac microwire | 25 | 75 | |
| Agg A | Re-aggregate | 100 | 0 | |
| Agg B | Re-aggregate | 75 | 25 | |
| Agg C | Re-aggregate | 50 | 50 | |
| Agg D | Re-aggregate | 25 | 75 | |

Figure 3(a)

| Subject | Conduction Velocity (cm/s) | Reference |
|---|---|---|
| Cardiomyopathic human heart during ventricular fibrillation | 25 ± 4.0 | [1] |
| Cardiomyopathic human heart during pacing | 41 (min) – 87 (max) | [1] |
| Healthy human heart | 46.4 ± 2.7 | [2] |
| Human CMW | 47.4 ± 12.4 | - |
| Healthy human heart - Purkinje fibres | ≈ 2000 | [2] |

Figure 5

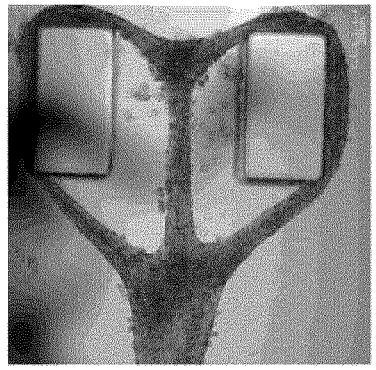
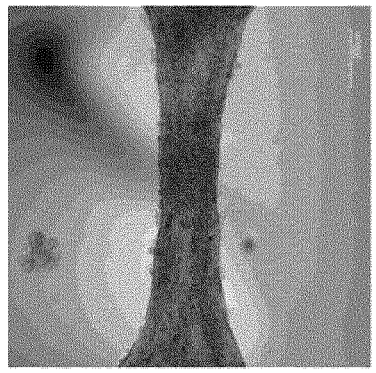
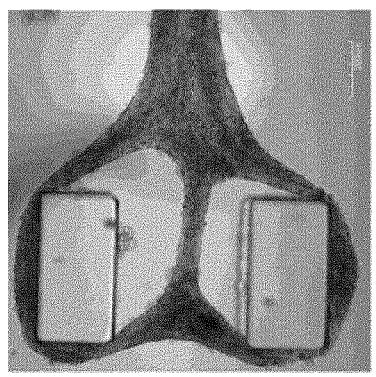
Figure 6(d)
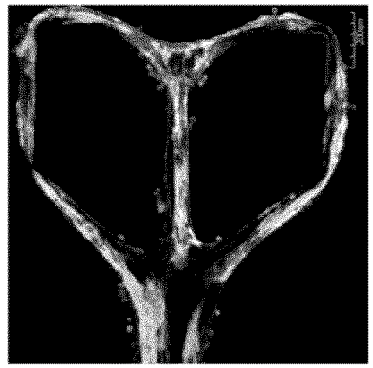
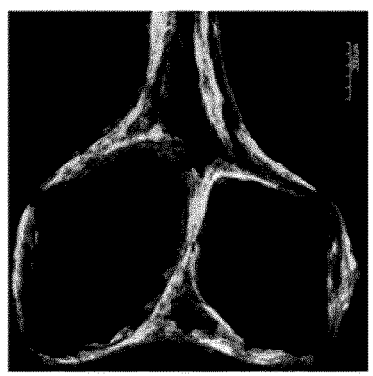
Figure 6(e)

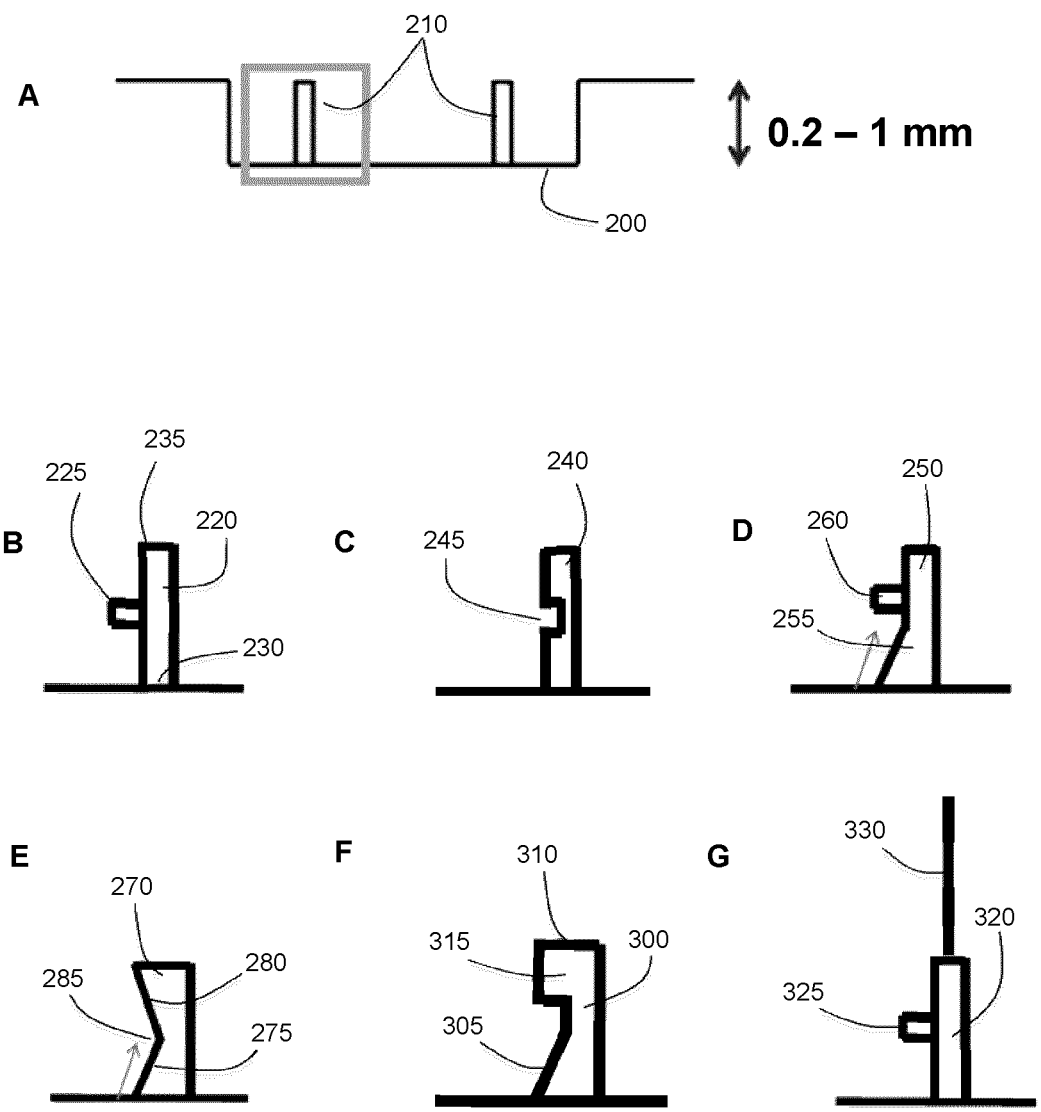
Figures 16 (a)-(g)

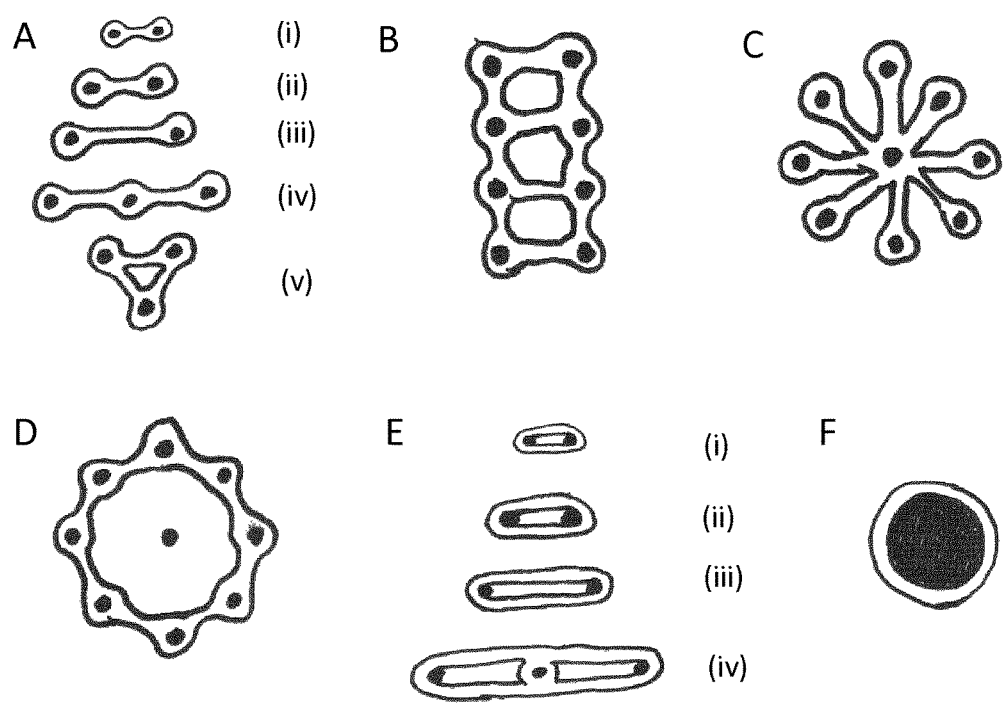
Figures 17 (a)-(f)

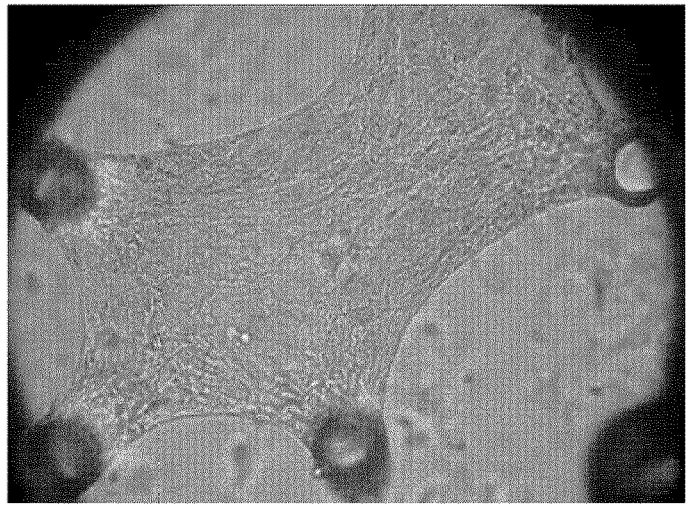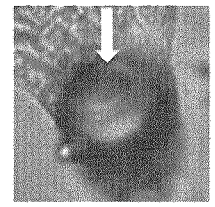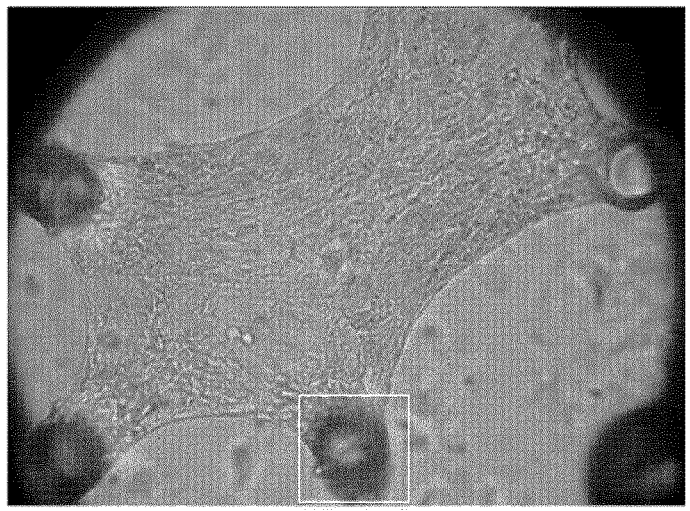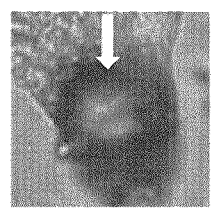
Figures 18 (a)-(d)

| Group | Collagen Concentration | Population Per Well |
|---|---|---|
| C1/0.25 | 2.0mg/ml | 0.25E6 |
| C2/0.25 | 2.5mg/ml | 0.25E6 |
| C3/0.25 | 3.0mg/ml | 0.25E6 |
| C1/1.0 | 2.0mg/ml | 1.0E6 |
| C2/1.0 | 2.5mg/ml | 1.0E6 |
| C3/1.0 | 2.5mg/ml | 1.0E6 |

|  | Day1 | Day2 | Day3 |
|---|---|---|---|
| C1/0.25 | 10.1039501 | 13.04347826 | 12.13191991 |
| C1/1.0 | 3.064150943 | 10.61489752 | 4.672897196 |
| C2/0.25 | 3.034257749 | 2.171099928 | 3.346411262 |
| C2/1.0 | 7.34229576 | 6.585762913 | 12.64874394 |
| C3/0.25 | 3.709896541 | 9.251360494 | 1.536058318 |
| C3/1.0 | 5.824330672 | 2.866196169 | 3.722397476 |

| Factor | Concentration (ng/mL) |
|---|---|
| GLP-1 | 100 |
| IGF-1 | 100 |
| HRG | 100 |
| VEGF | 80 |
| BFGF | 100 |
| G-CSF | 80 |
| SDF-1 | 100 |

CARDIAC TISSUE CONSTRUCTS AND METHODS OF FABRICATION THEREOF

CROSS-REFERENCE TO RELATED APPLICATION

This application is a National Phase application claiming the benefit of the international PCT Patent Application No. PCT/CA2013/050940, filed on Dec. 6, 2013, in English, which claims priority to U.S. Provisional Application No. 61/734,859, titled "CARDIAC TISSUE CONSTRUCTS AND METHODS OF FABRICATION THEREOF" and filed on Dec. 7, 2012, the entire contents of which are incorporated herein by reference, and to U.S. Provisional Application No. 61/843,285, titled "CARDIAC TISSUE CONSTRUCTS AND METHODS OF FABRICATION THEREOF" and filed on Jul. 5, 2013, the entire contents of which is incorporated herein by reference.

BACKGROUND

The present disclosure relates to tissue constructs and microscale platforms for their fabrication. More particularly, the present disclosure relates to cardiac tissue constructs, and applications thereof in screening.

Drug- and cell-based strategies for treating heart disease, including myocardial infarction, face significant roadblocks on the path to the clinic, a primary obstacle being the lack of information-rich in vitro human model systems. Conventional model systems are hampered by at least one of three fundamental limitations which include 1) the lack of a mature in vivo-like microenvironment specifically engineered for the input cell population, 2) a relatively low-throughput assay, and 3) the low-content nature of output parameters.

Directed differentiation strategies for generating and preserving human pluripotent stem cell (hPSC)-derived cardiomyocytes in scaled-up quantities are capable of efficiencies greater than 90% [1-7]. Additionally, several cell surface markers for cardiomyocytes have been discovered which can be used to sort out purified populations of interest using combinations of appropriate antibodies [8, 9]. Along with the recent advances in induced Pluripotent Stem Cell (iPSC) technology, one now has the ability to derive patient-specific cardiomyocytes on demand without lack in cell quantity. Despite these advances in scale-up of cardiomyocyte production and improvements in methods of purification and preservation, there is much needed work to be done in developing suitable methods of effectively using these target cells in a clinically useful manner.

One such area of value is in developing physiologically relevant in vitro model platforms for cardiac toxicity and drug screening. Although inducing hPSC to differentiate into contracting cardiomyocytes is an established technique, the maturation stage of these cells lack severely in comparison to adult cardiomyocytes [5]. Conventionally, hPSC-derived cardiomyocytes are used at early stages of differentiation, and cultured without supporting cells on two-dimensional stiff surfaces that 1) do not mimic the native heart microenvironment and 2) are not amenable to measuring appropriate parameters which can be linked to cardiac physiology (such as impulse propagation, conduction velocity, and force of contraction).

SUMMARY

Methods and devices are provided for the formation of cardiac tissue constructs. In some embodiments, methods are provided for forming cardiac tissue constructs that including cardiomyocytes, non-myocytes, and extracellular matrix, and which exhibit properties associated with healthy cardiac tissue. In some embodiments, microfabrication platforms are provided to support the transmission of dynamic electromechanical forces, such that the cardiac microtissue constructs may be formed mimicking the basic microenvironment found in the heart. The microfabrication platform may include retaining features for stabilizing the position of the microtissue construct during its formation. In some embodiments, the microfabrication platform may be configured to the application of point electrical stimulation, and/or to amplify the transduction of force into a visible displacement.

Accordingly, in one aspect, there is provided a microfabrication platform for forming a tissue construct, comprising:
 a substrate; and
 two or more retaining structures supported by said substrate, wherein said retaining structures are positioned to apply tension to a tissue construct seeded on said substrate during formation of the tissue construct;
 wherein at least one retaining structure includes a stabilizing feature for stabilizing the position of the tissue construct during its formation; and
 wherein said stabilizing feature is provided at an intermediate location between said substrate and a distal end of said retaining structure.

In another aspect, there is provided a microfabrication platform for forming a tissue construct, comprising:
 a substrate;
 two or more retaining structures supported by said substrate, wherein said retaining structures are positioned to apply tension to a tissue construct seeded on said substrate during formation of the tissue construct; and
 a pair of electrodes supported by said substrate and having a relative spacing suitable for point stimulation of the tissue construct.

In another aspect, there is provided a microfabrication platform for forming a tissue construct, comprising:
 a substrate; and
 two or more retaining structures supported by said substrate, wherein said retaining structures are positioned to apply tension to a tissue construct seeded on said substrate during formation of the tissue construct;
 wherein at least one retaining structure includes a stabilizing feature for stabilizing the position of the tissue construct during its formation; and
 wherein said retaining structures are adapted such that the tissue construct exhibits a pathology.

In another aspect, there is provided a method of forming a cardiac tissue construct using a microfabrication platform;
 the microfabrication platform comprising:
 a substrate; and
 two or more retaining structures supported by said substrate, wherein said retaining structures are positioned to apply tension to a tissue construct seeded on said substrate during formation of the tissue construct;
 the method comprising:
 dispensing, onto the substrate, a mixture comprising collagen mastermix, cardiomyocytes, and fibroblasts, such that the at least two retaining structures are surrounded by the mixture; and
 incubating the substrate for a time duration suitable for remodeling of the mixture into the cardiac tissue construct, such that the cardiac tissue construct is suspended between the at least two retaining structures under tension;

wherein a ratio of cardiomyocytes to the total number of cells is provided such that the cardiac tissue construct exhibits a conduction velocity characteristic of healthy human heart tissue.

In another aspect, there is provided a microfabrication platform for forming a tissue construct, comprising:
a microwell;
a ramped support structure provided within said microwell, said ramped support structure extending upwardly from a base of said microwell; and
one or more retaining structures provided on said ramped support structure, wherein said one or more retaining structures are positioned to apply tension to a tissue construct seeded within said microwell during formation of the tissue construct.

In another aspect, there is provided a microfabrication platform for forming a tissue construct, comprising:
a microwell;
a support structure provided within said microwell, said support structure extending upwardly from a base of said microwell; and
two or more retaining structures supported by said support structure, wherein said two or more retaining structures are configured to apply tension to a tissue construct seeded within said microwell during formation of the tissue construct;
wherein said support structure has a shape configured to prevent tissue formation between said retaining structures during a tissue remodeling process.

In another aspect, there is provided a method of forming a tissue construct using a microfabrication platform;
the microfabrication platform comprising:
a microwell;
a ramped support structure provided within the microwell, the ramped support structure extending upwardly from a base of the microwell; and
one or more retaining structures provided on the ramped support structure, wherein the one or more retaining structures are configured to apply tension to a tissue construct seeded within the microwell during formation of the tissue construct;
the method comprising:
dispensing, into the microwell, a pre-polymerized matrix that is configured to form the tissue construct according to a remodeling process, wherein the pre-polymerized matrix is dispensed into a region surrounding the ramped support structure without contacting the one or more retaining structures; and
incubating the microwell for a time duration suitable for remodeling of the pre-polymerized matrix into the tissue construct, such that the tissue construct moves upwards along the ramped support structure during the remodeling process and is retrained in a ring geometry by the retaining structures.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 1(d)(iii)-(viii) show staining for sarcomeric alpha-actinin of BITF microtissues (bright field on the left ((iii), (v), (vii)) and alpha-actinin staining on the right ((iv), (vi), (viii)). Staining for sarcomeric alpha-actinin (white filaments indicated with arrows) confirms expression in border regions. DAPI-stained nuclei are shown as round white dots.

FIGS. 1(e)(ix)-(xii) show staining for sarcomeric alpha-actinin of cardiac microwires (bright field on the left ((ix), (xi)) and sarcomeric alpha-actinin staining on the right (x), (xii)). Immunostaining for cardiac troponin T (white arrows in first column of panels) and sarcomeric alpha-actinin (white arrows in second column of panels) confirms sarcomere expression in all regions along longitudinal axis.

Figure 2A:
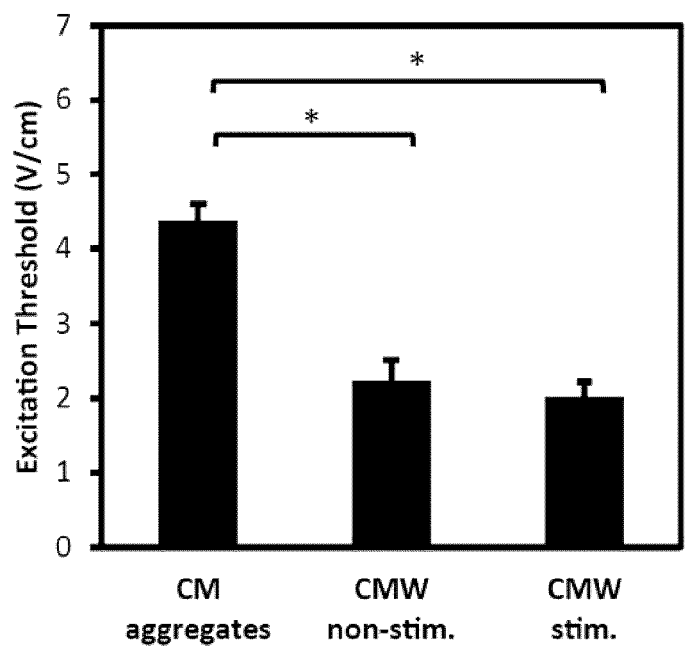
FIGS. 2(a) and 2(b) plot the electrophysiological assessment of a cardiac microwire, showing (a) excitation threshold and (b) maximum capture rate, respectively, of non-dissociated human Embryonic Stem Cell (hESC)- cardiomyocyte aggregates, non-stimulated cardiac microwire, and stimulated cardiac microwire.
Figure 2B:
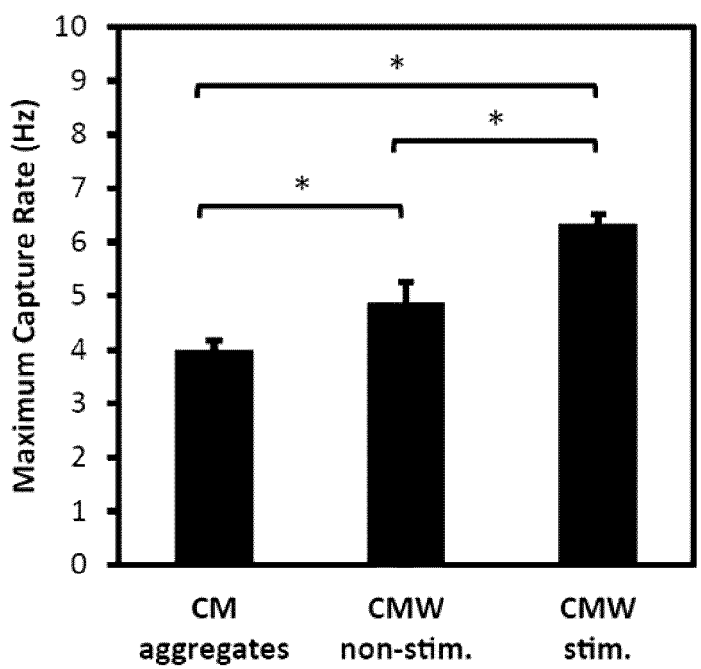
Figure 2C:
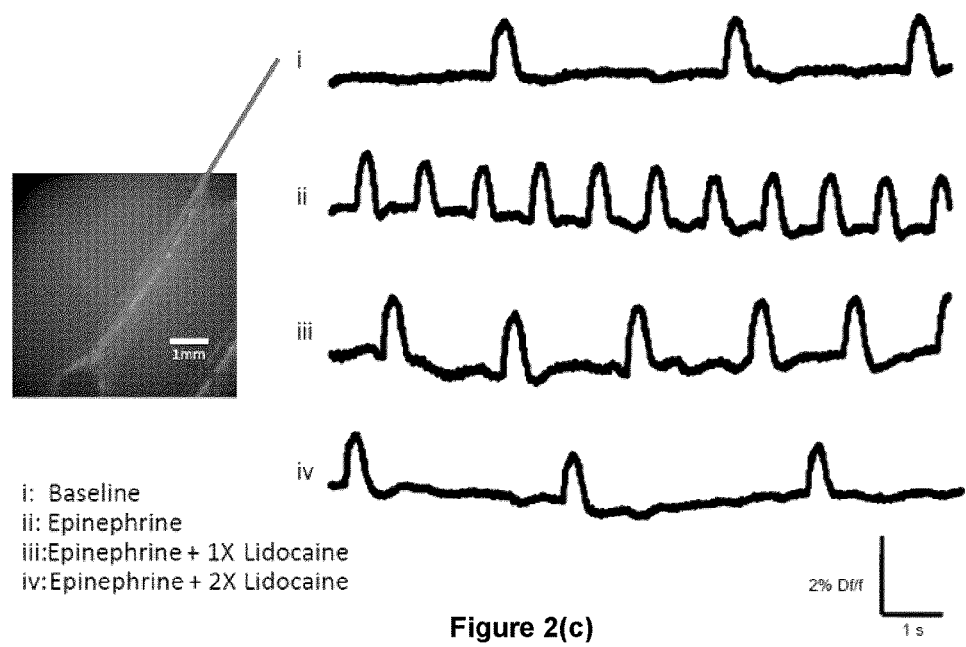
Figure 2D:
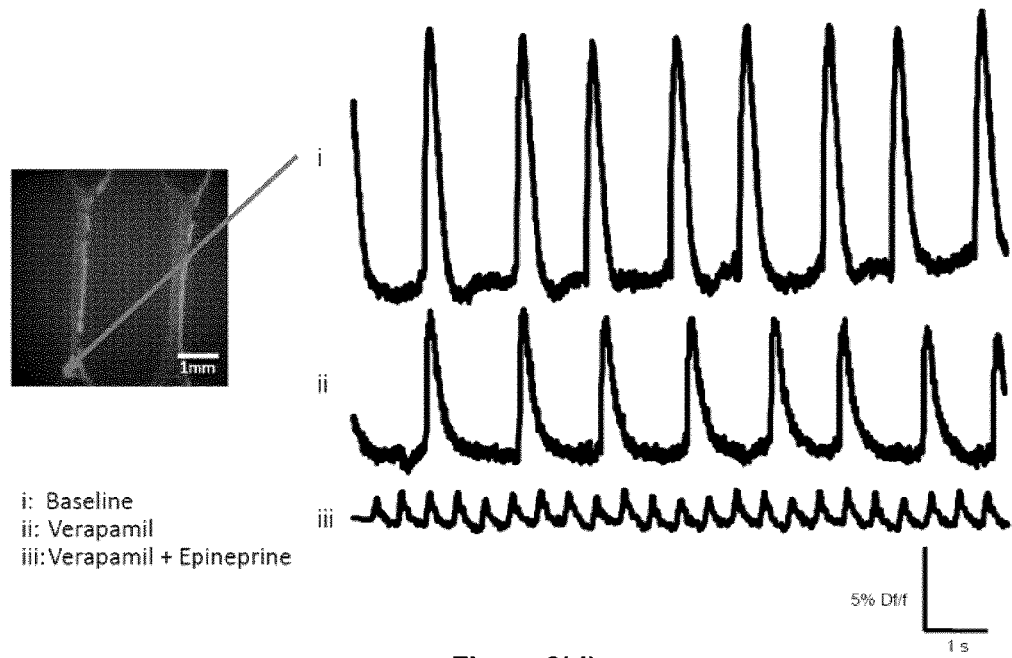

FIGS. 2(c) and 2(d) show results from optical mapping, which was employed to record transmembrane action potentials and intracellular calcium transients, for which the cardiac microwire responded as expected to drugs with known effects. FIG. 2(c) shows results for epinephrine, an adrenergic neurotransmitter, which increased activation rate (ii) and Lidocaine, an antiarrhythmic drug, which decreased the activation rate (iii, iv) relative to the baseline control (i). FIG. 2(d) shows results for Verapamil, an L-type $Ca^{2+}$ channel blocker, which reduced the amplitude of calcium waves in cardiac microwire (ii) relative to the baseline control (i) and where supplementing with Epinephrine increased the rate of calcium transients (iii).

Figure 2E:
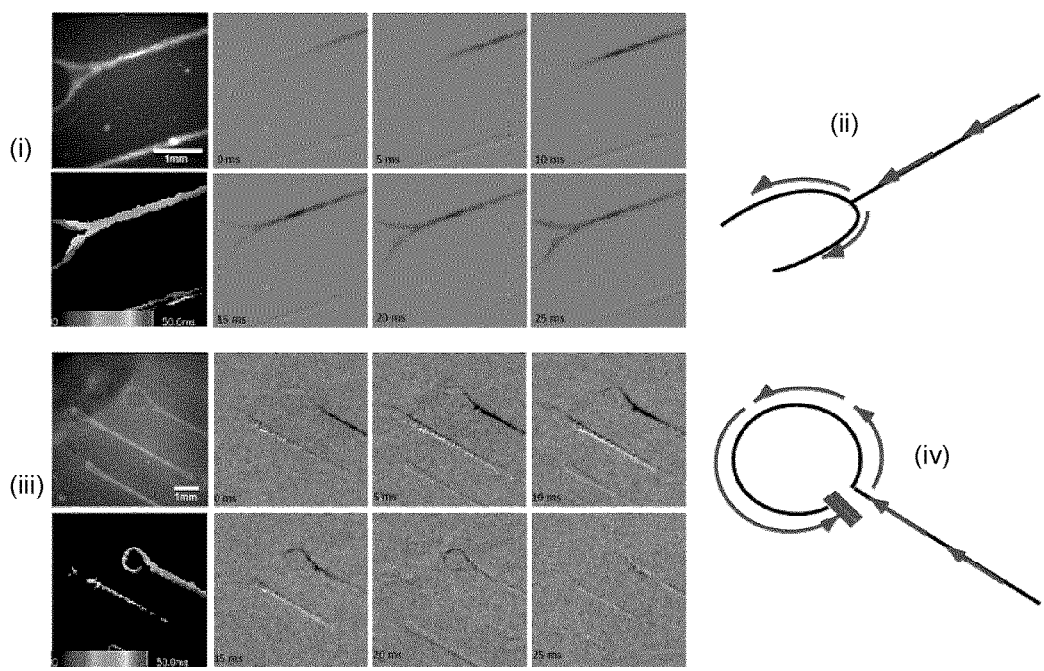

FIG. 2(e) includes a first set (i) of images showing action potential (AP) propagation of a normal cardiac microwire, where each panel depicts a time lapse of the AP propagation along the longitudinal axis of the cardiac microwire (illustrated by (ii)), and a second set of images (iii) showing AP propagation of the cardiac microwire, which was observed to be obstructed by a conduction block resulting in a re-entrant wave-like system (illustrated by (iv)).

Figure 2F:
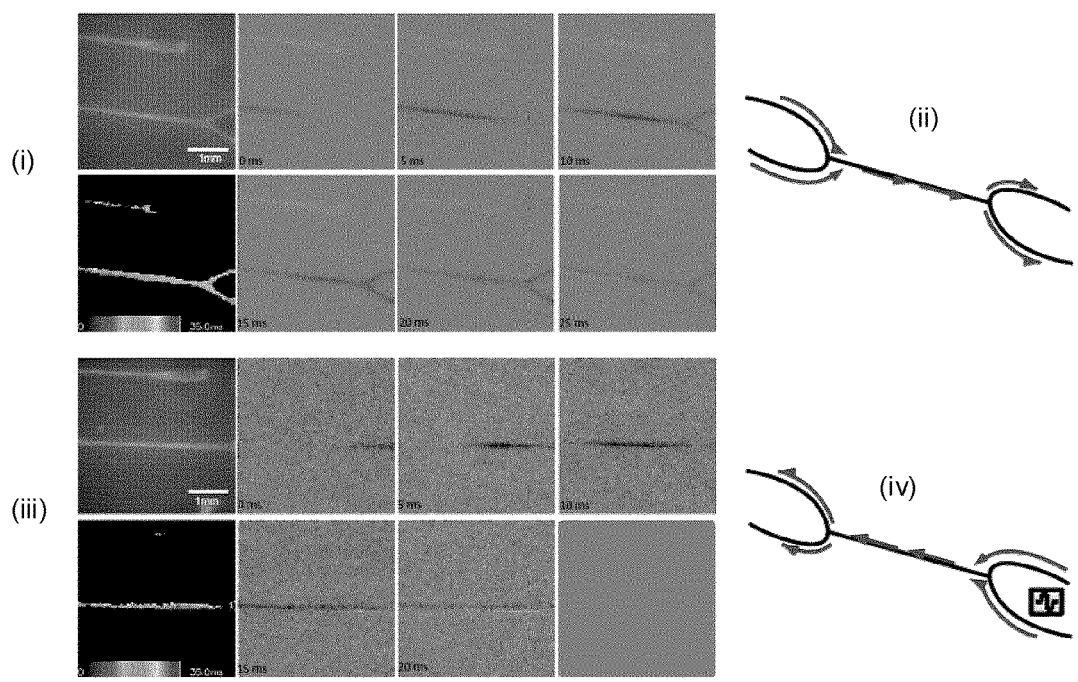

FIG. 2(f) includes a first set (i) of images showing direction of spontaneous AP propagation of normal cardiac microwire (illustrated by (ii)), and a second set (iii) of images showing how the direction can be reversed using electrical point stimulation (illustrated by (iv)). Location trace of recording and timescales are indicated.

Figure 2G:
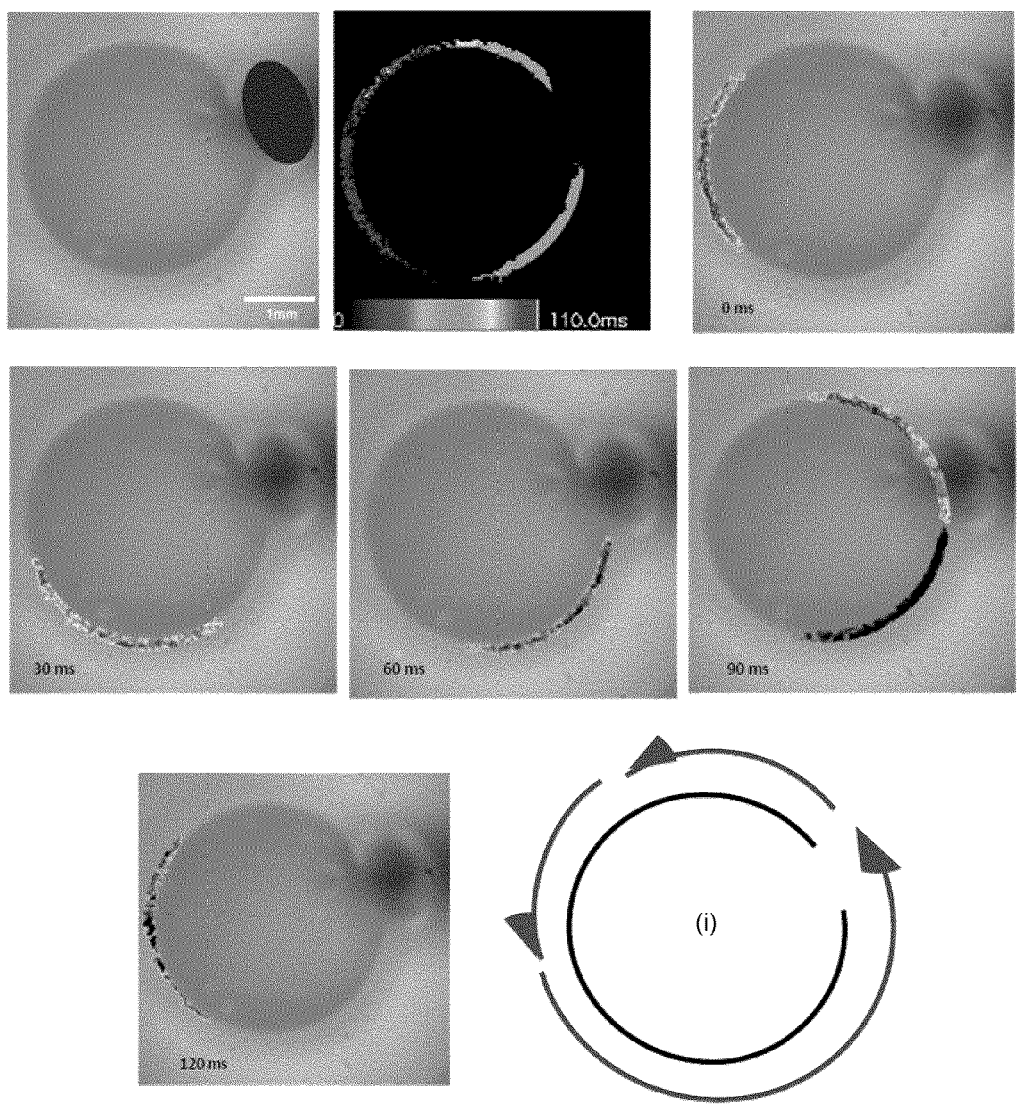

FIG. 2(g) shows images of a cardiac microwire generated using a circular substrate, which was designed to create a ring of tissue mimicking a reentrant wave during fibrillation (illustrated by (i)). Electrophysiological assessment revealed spontaneous infinite loop-like cycles of AP propagation traversing the ring; one cycle is shown. Data are reported as the mean±SEM., P<0.05 (Mann-Whitney U test).

Figure 3B:
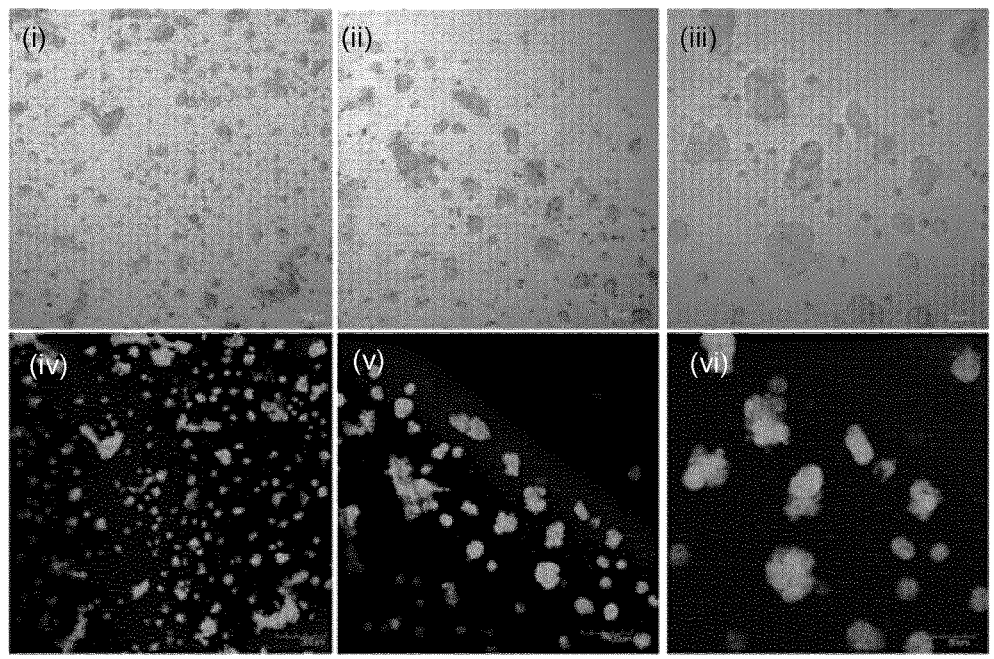
Figure 3C:
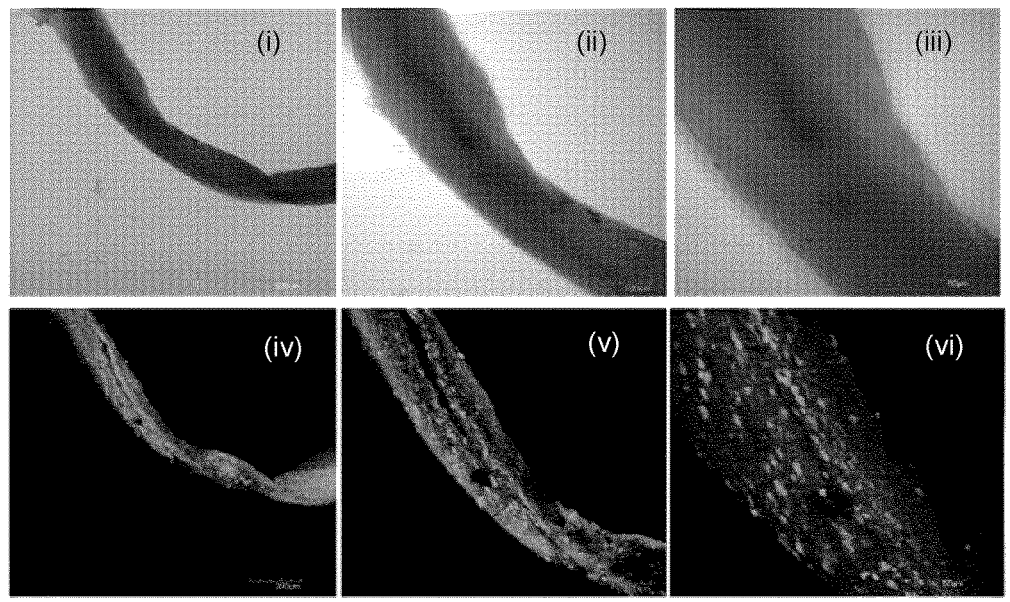
Figure 3D:
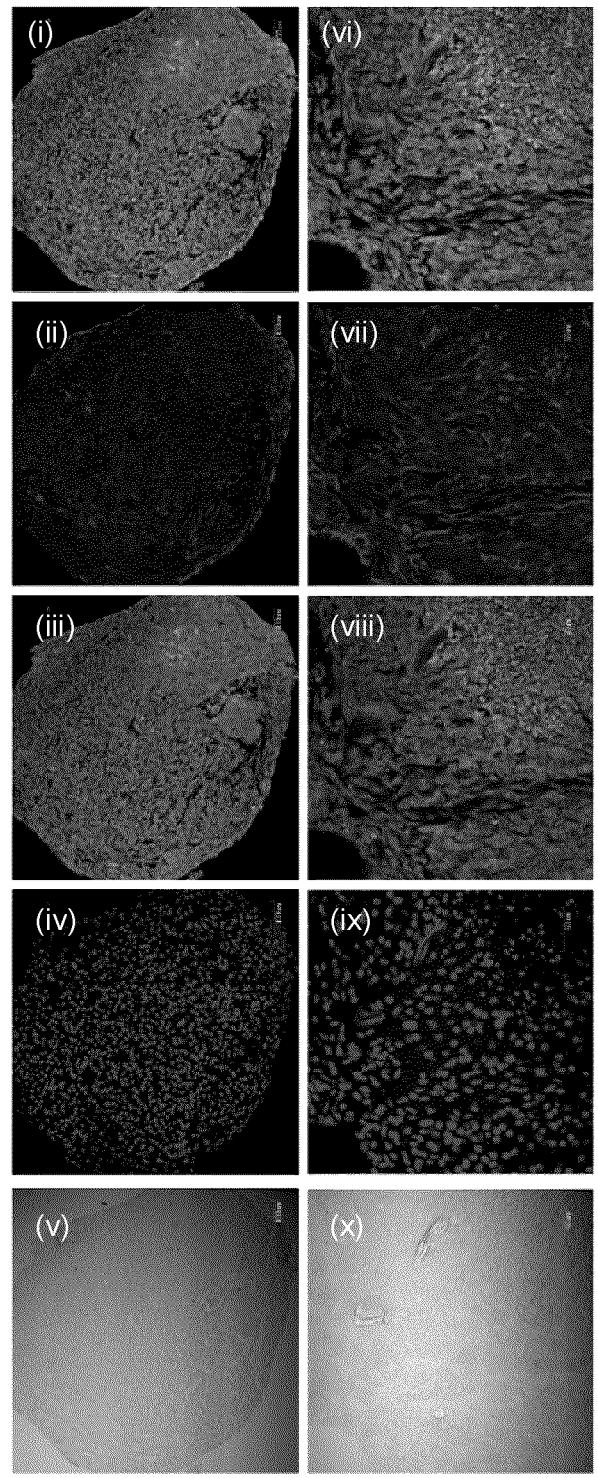
Figure 3E:
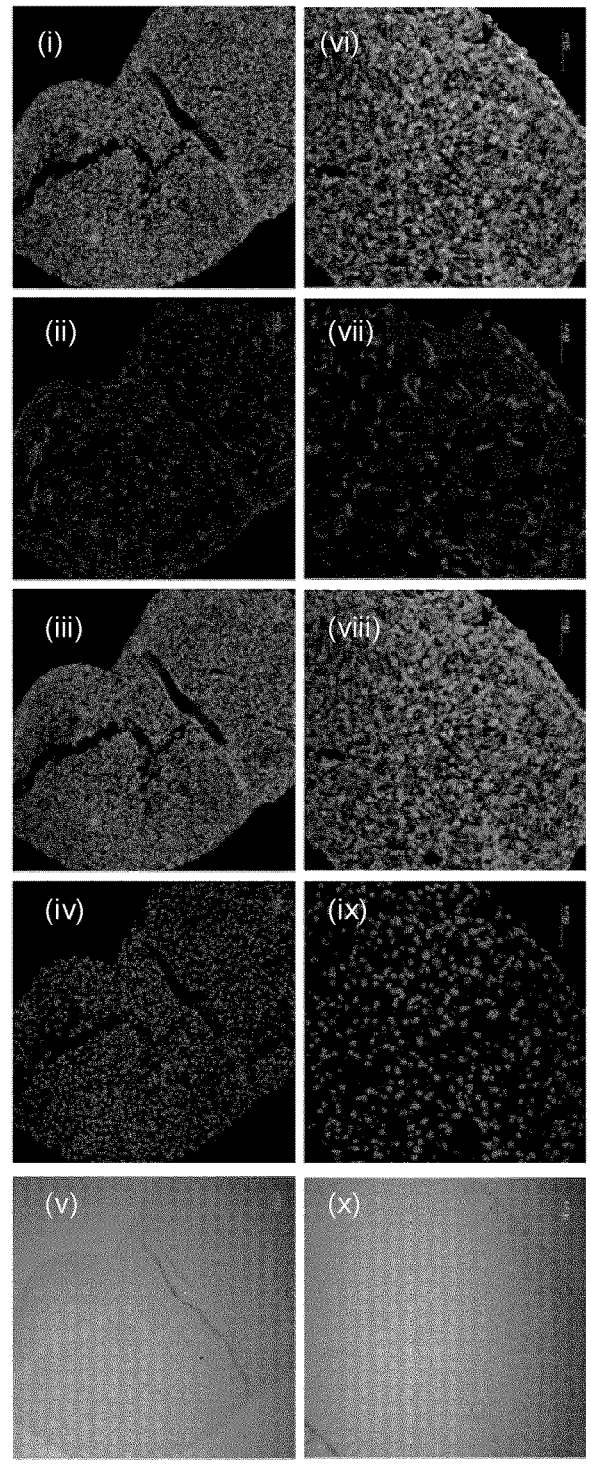
Figure 3F:
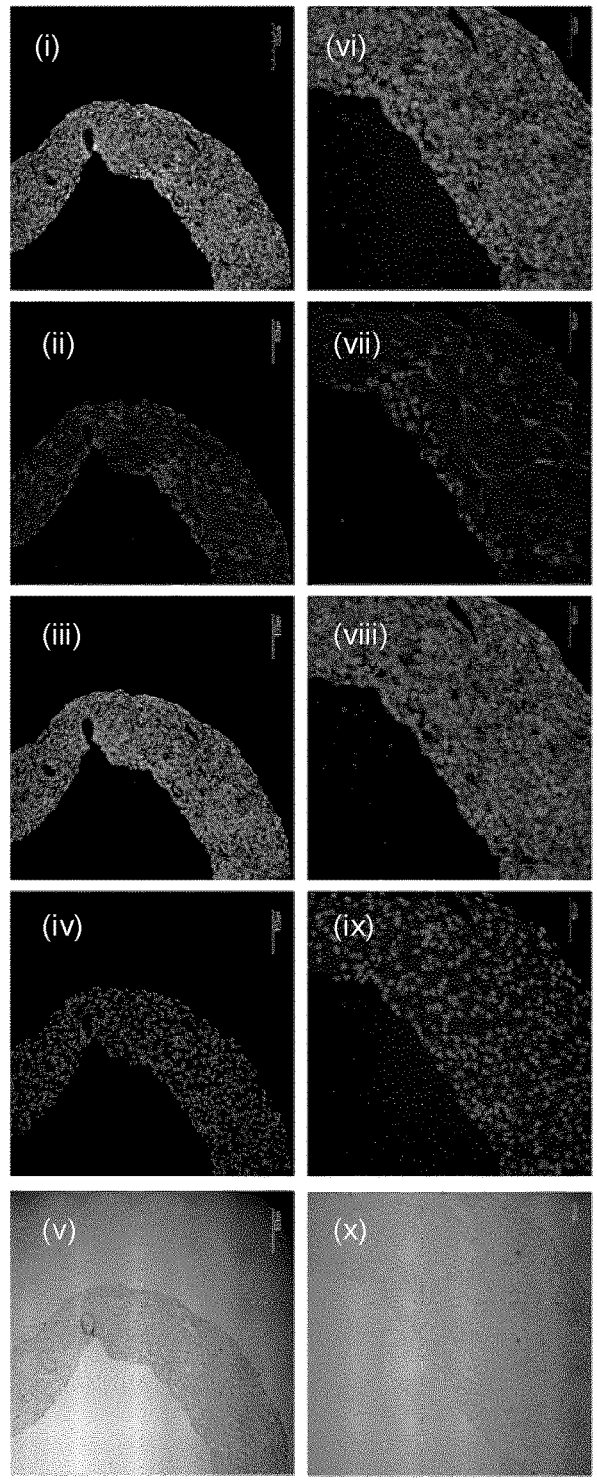

FIGS. 3(a)-3(f) relate to compositions obtained with different input populations of NKX2-5+ and CD90+ cells, which self-organize to determine tissue morphogenesis. FIG. 3(a) shows how NKX2-5-GFP+ cells (cardiomyocytes) and CD90+ cells (FB) were sorted from hESC-cardiomyocytes, and mixed at specific ratios in cardiac microwire (CMW) and aggregates (Agg). The percentages shown indicate the percentage of a given cell type, relative to the total number of cells forming the construct or aggregate. Non-dissociated and non-sorted controls were also used. FIG. 3(b) shows a cardiac microwire composed of pure NKX2-5-GFP+ cells (condition 'A'), which formed a globular morphology with non-integrating colonies of cardiomyocytes. FIGS. 3(b)(i)-(iii) show bright field images of NKX2-5-GFP+ while corresponding immunofluorescent images are shown in FIGS. 3(b)(iv)-(vi). Gradually higher magnifications are shown moving from left (images 3(b)(i) and 3(b)(iv)) to right (images 3(b)(iii) and 3(b)(vi)). FIG. 3(c) shows a cardiac microwire composed of 75% NKX2-5-GFP+ cells and 25% CD90+ cells (condition 'B'), which produced well-integrated tissue with robust architecture. NKX2-5-GFP+ cells appear white in immunofluorescent images (FIGS. 3(c)(iv)-(vi)). FIGS. 3(c)(i)-(iii) show bright field images of cells while FIGS. 3(c)(iv)-(vi) show corresponding immunofluorescent images of NKX2-5-GFP+. Gradually higher magnifications are shown moving from left (images 3(c)(i) and 3(c)(iv)) to right (images 3(c)(iii) and 3(c)(vi)). FIGS. 3(d)-3(f) show immunofluorescence micrographs of (d) non-dissociated aggregates, (e) aggregates of condition 'B', and (f) cardiac microwire of condition 'B' (DAPI-stained nuclei appear as round white dots (iv and ix), NKX2-5-GFP+ cells shown in white (iii and viii), and Vimentin expression shown in white (ii and vii)). Corresponding bright field images are provided in FIGS. 3(d) (v) and (x), 3(e) (v) and (x), and 3(f) (v) and (x).

Figure 4A:
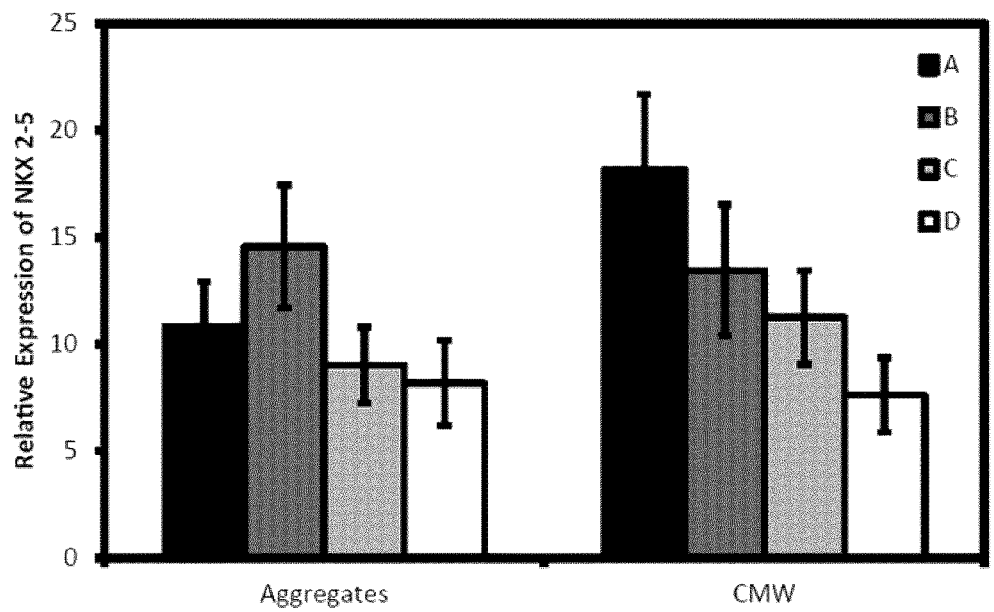
Figure 4B:
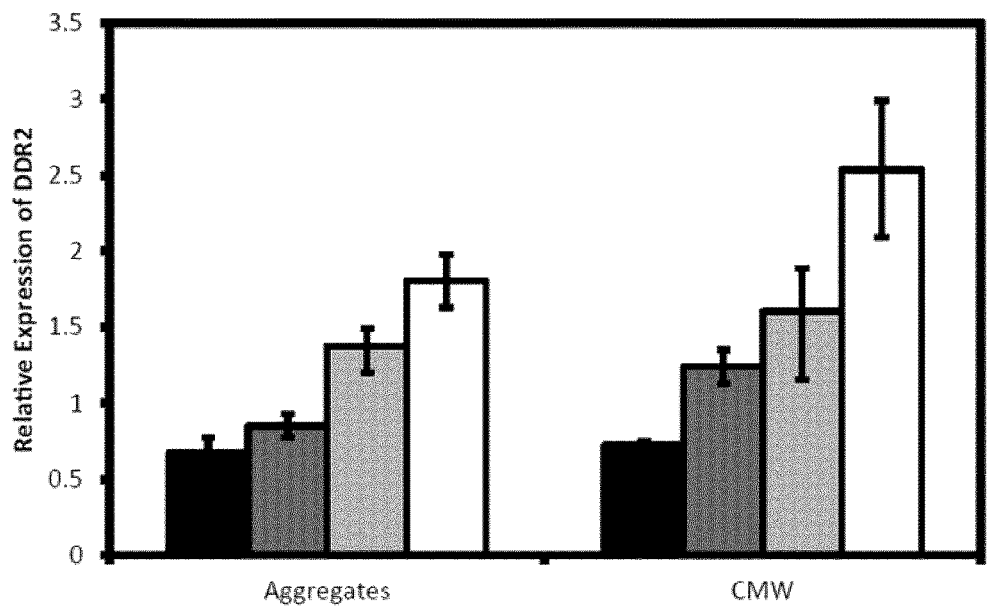
Figure 4C:
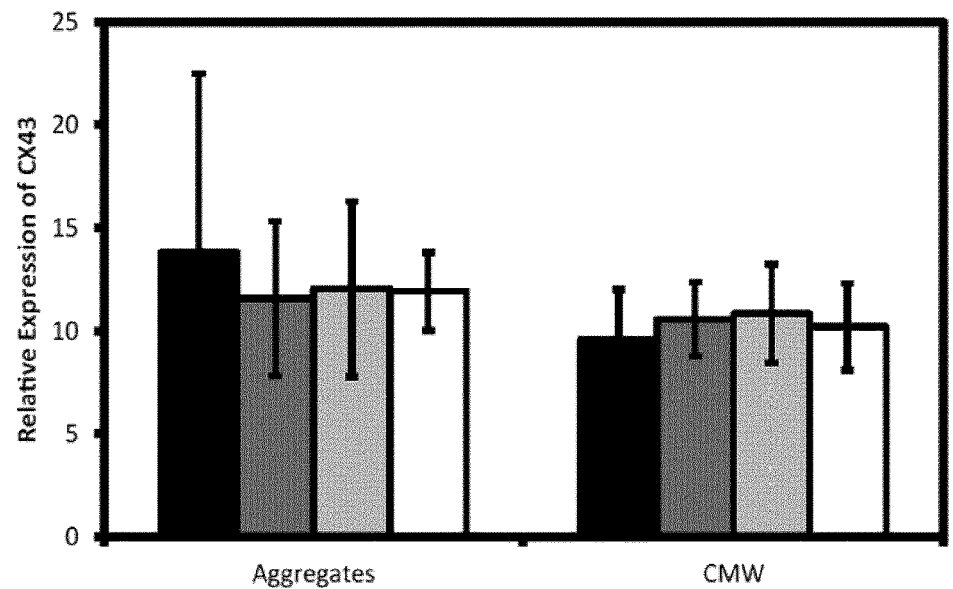
Figure 4D:
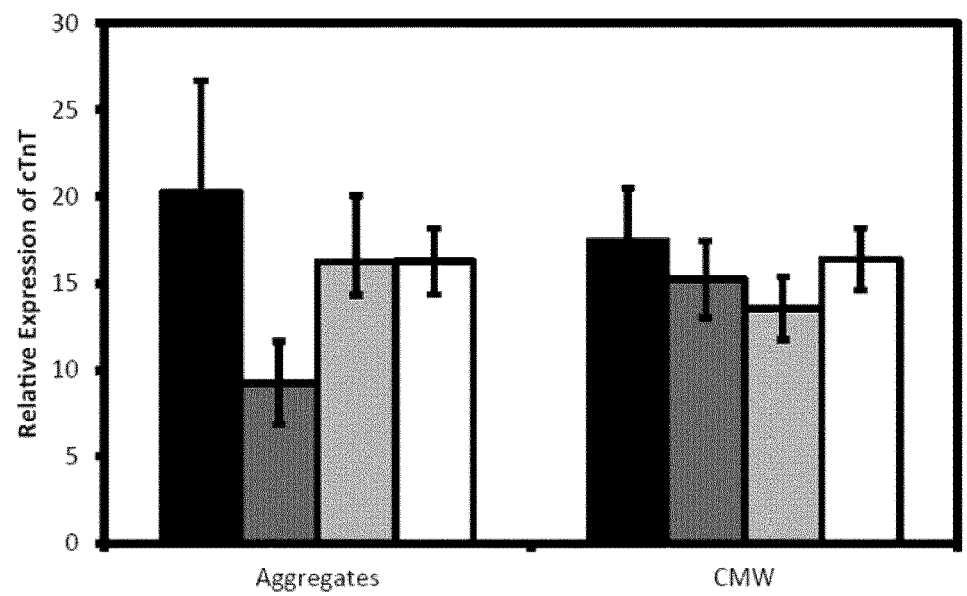
Figure 4E:
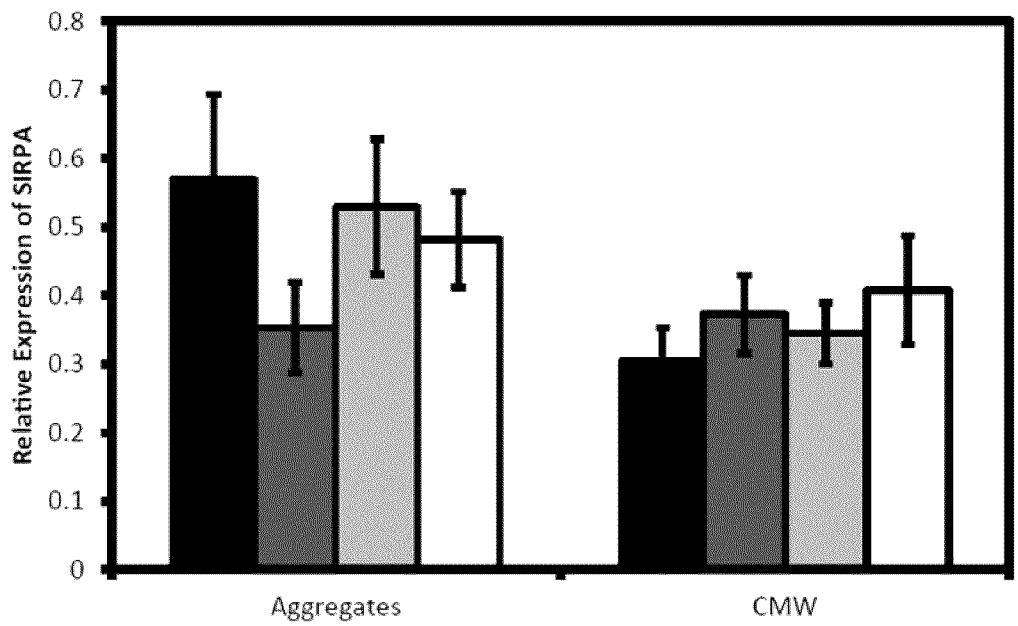
Figure 4F:
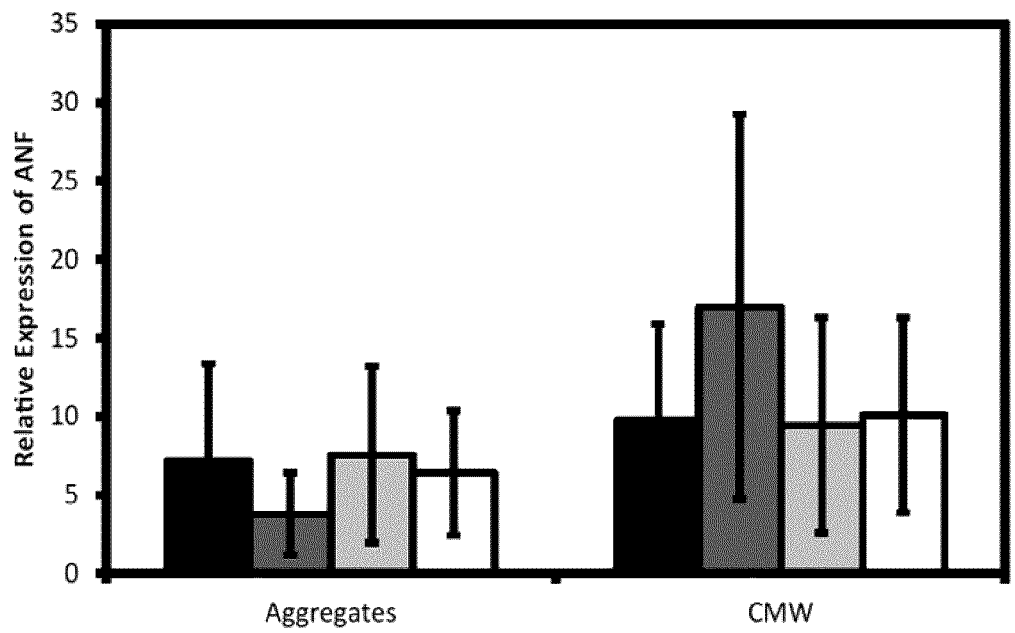
Figure 4G:
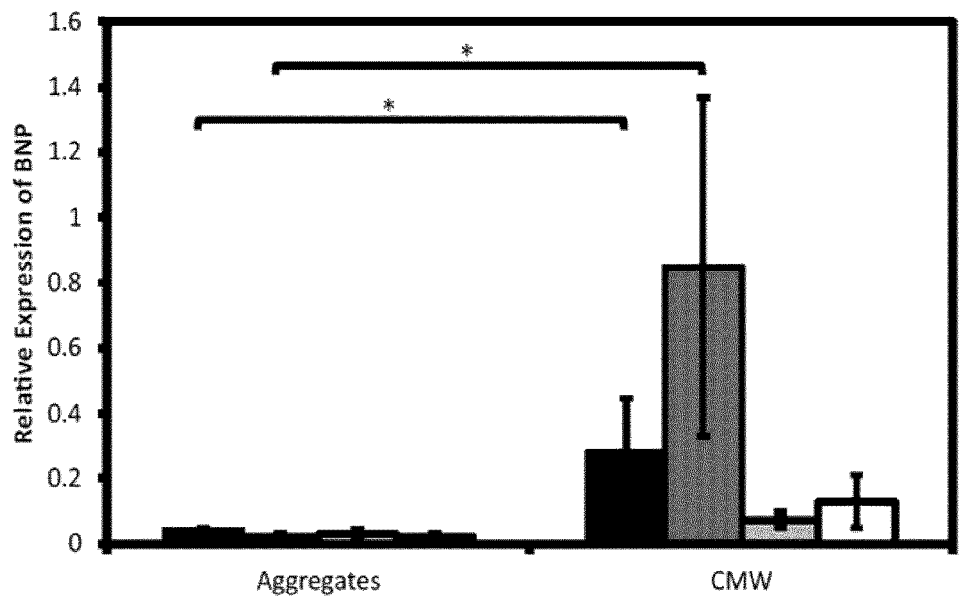
Figure 4H:
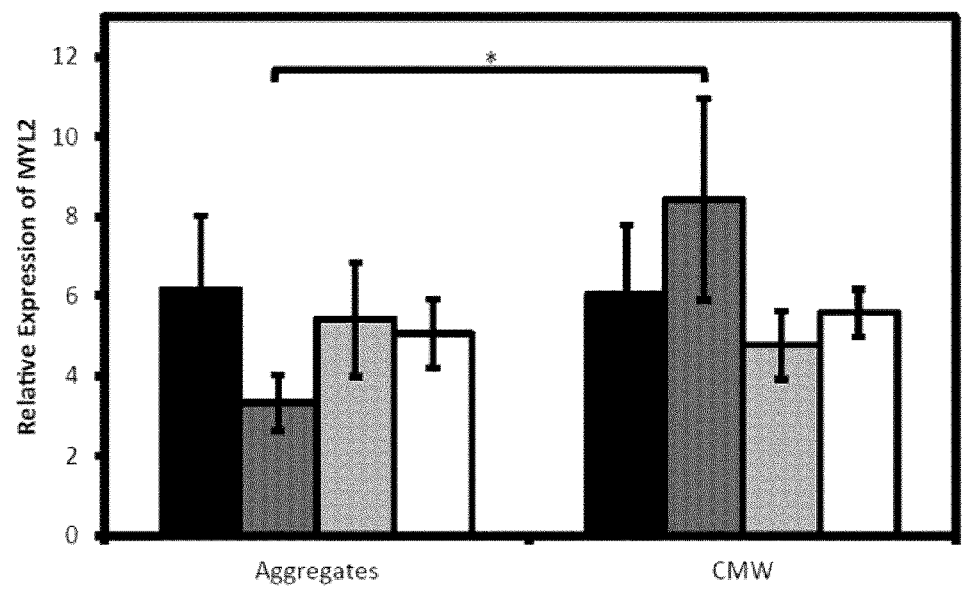
Figure 4I:
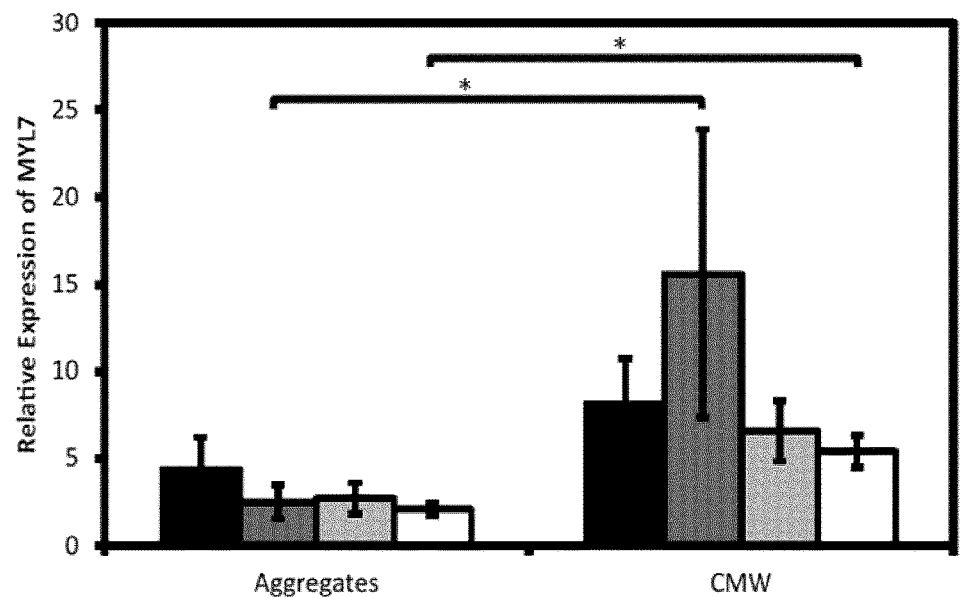
Figure 4J:
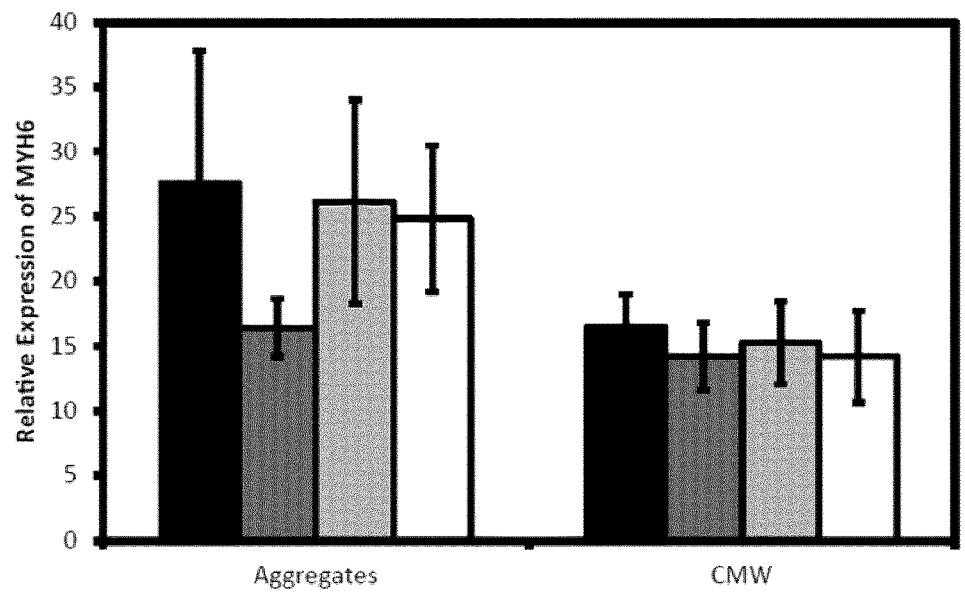
Figure 4K:
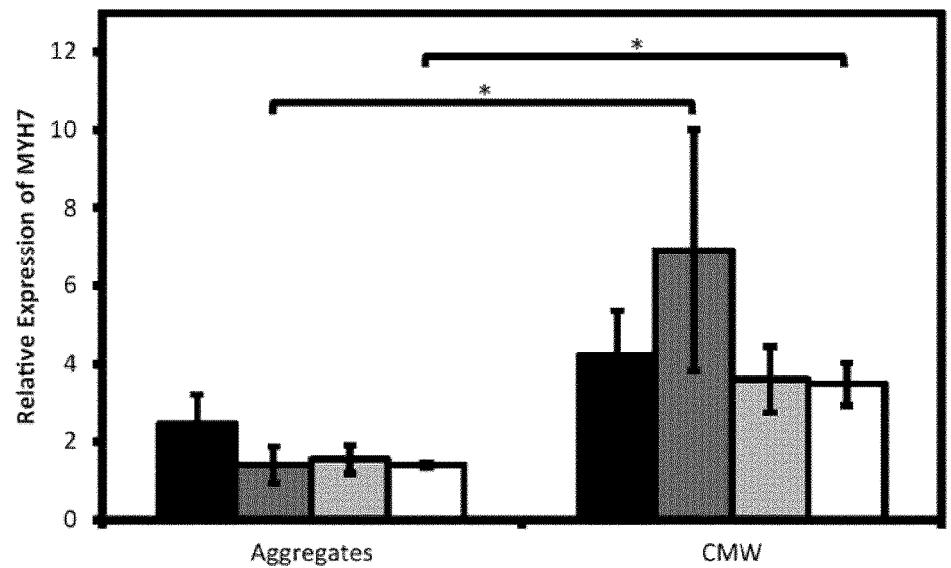
Figure 4L:
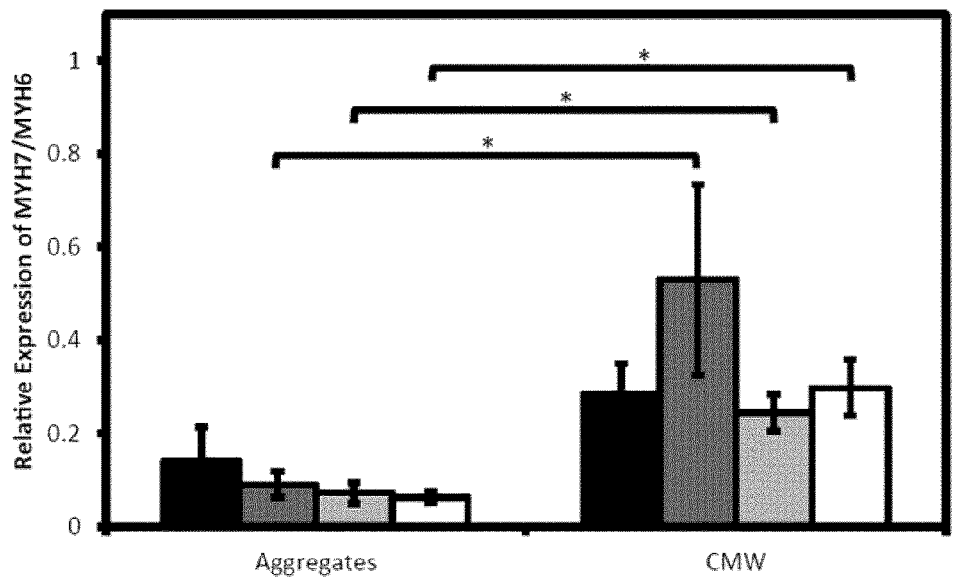

FIGS. 4(a)-(l) provide results in which gene expression analyses of cardiomyocyte control and maturation markers show dilution consistency of input cell composition and maturation effects in cardiac microwire. A, B, C, D correspond respectively to 100, 75, 50, and 25 percent NKX2-5-GFP+ cells with the remainder percentage consisting of CD90+ cells. Relative expression of NKX2.5 (FIG. 4(a)) and DDR2 (FIG. 4(b)) served as control markers of bulk tissue population. FIG. 4(c) shows relative expression of Cx43 expressed in both cardiomyocytes and FB. In FIGS. 4(d)-(l), all cardiac-specific markers (cTnT, SIRPA, ANF, BNP, MYL2, MYL7, MYH6, MYH7) are normalized to NKX2.5 expression levels to account for cardiomyocyte numbers in the mixed population of tissue. Data are reported as the mean±SEM., P<0.05 (Mann-Whitney U test).

FIG. 5 is a table showing a comparison of conduction velocities of native human heart tissue and the cardiac microwire system. Values of normal and pathophysiological conduction velocities of the human heart obtained from literature are shown. Values for cardiac microwire were measured from three separate experiments via optical mapping techniques. Microengineered cardiac microwires were found to exhibit conduction velocities on par with the epicardium of a healthy human heart. Data are reported as the mean±SEM.

FIGS. 6 (a)-(e) show microtissue formation in microfabricated platforms. FIG. 6(a) shows images (1-6) illustrating the process of tissue formation, in which cells are seeded and centrifuged into recessions and allowed to remodel to form microtissues based on node geometries. FIG. 6(b) is an image showing platforms with deflecting posts, which can be used to measure forces exerted by tissue and to also constrain tissue remodeling at various degrees. FIG. 6(c) shows an image demonstrating how microtissues can be arrayed on a common surface to increase samples per well. FIGS. 6(d) (bright field) and (e) (co-immunofluorescence for Phalloidin-stained actin filaments and cTnT) show images illustrating how microtissues can be fixed, permeabilized, stained, and imaged in situ within the microtissue seeding substrate. Areas of brighter contrast indicate co-localization of actin and cTnT in cells.

Figure 6A:
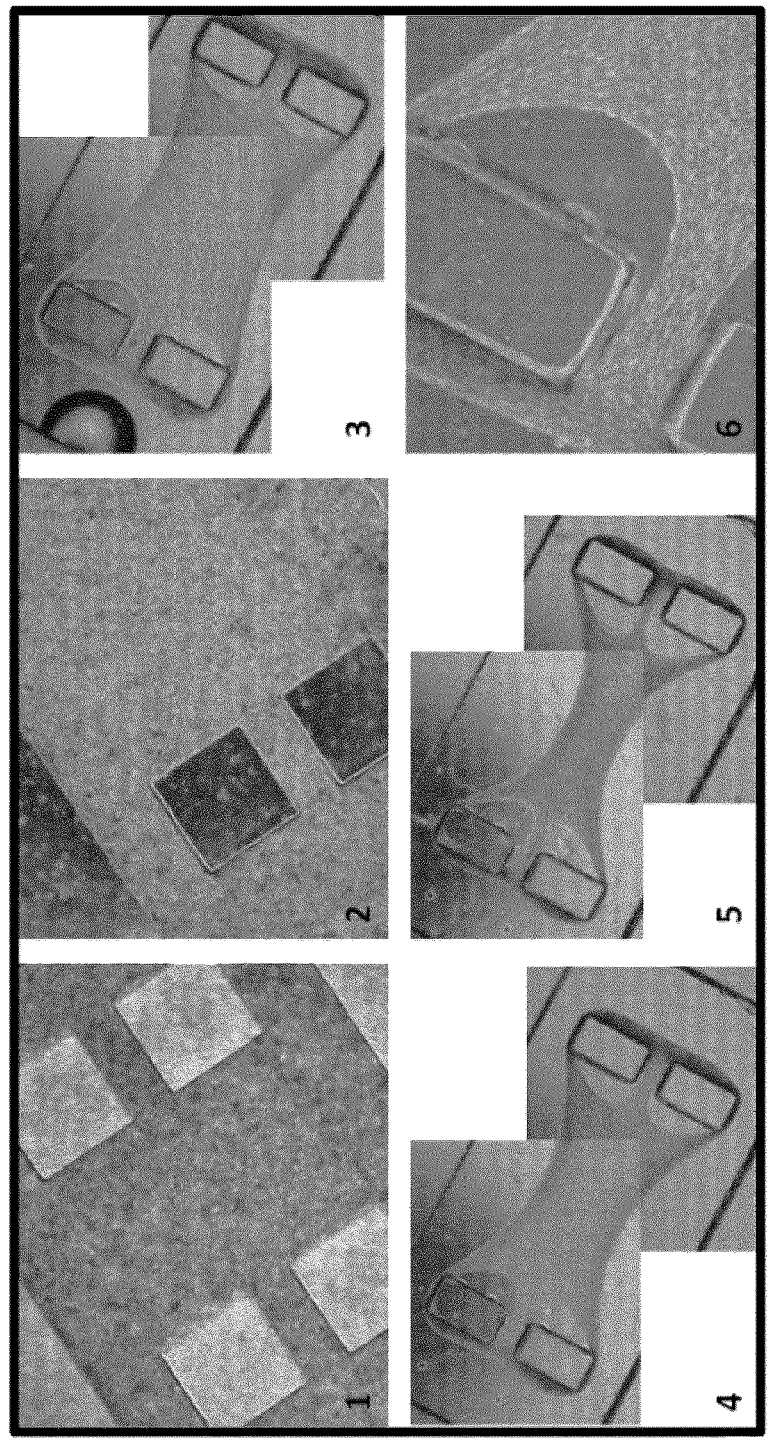
Figure 6B:
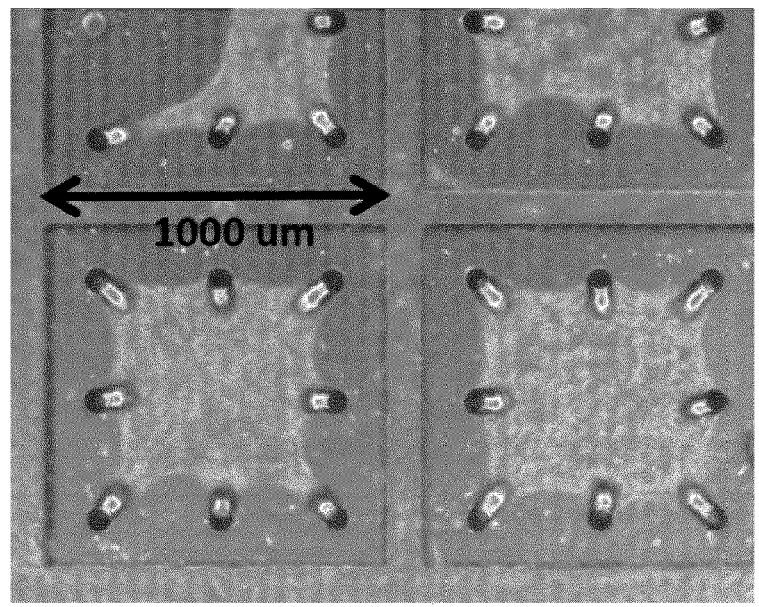
Figure 6C:
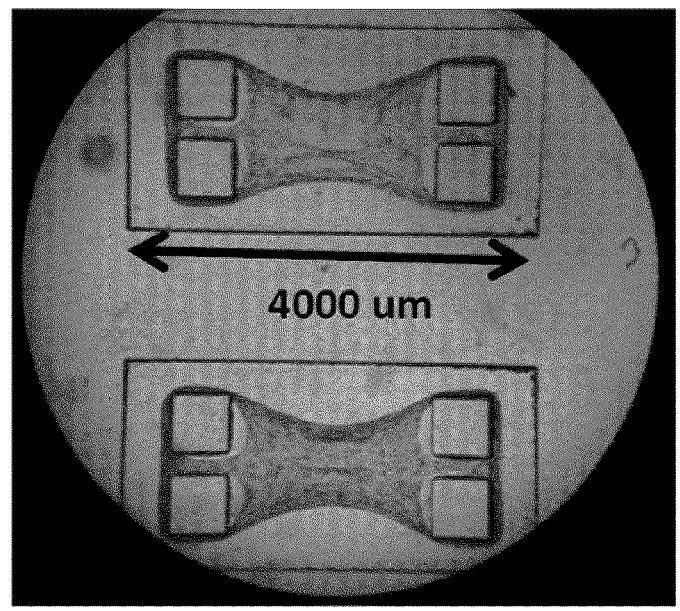
Figure 6F:
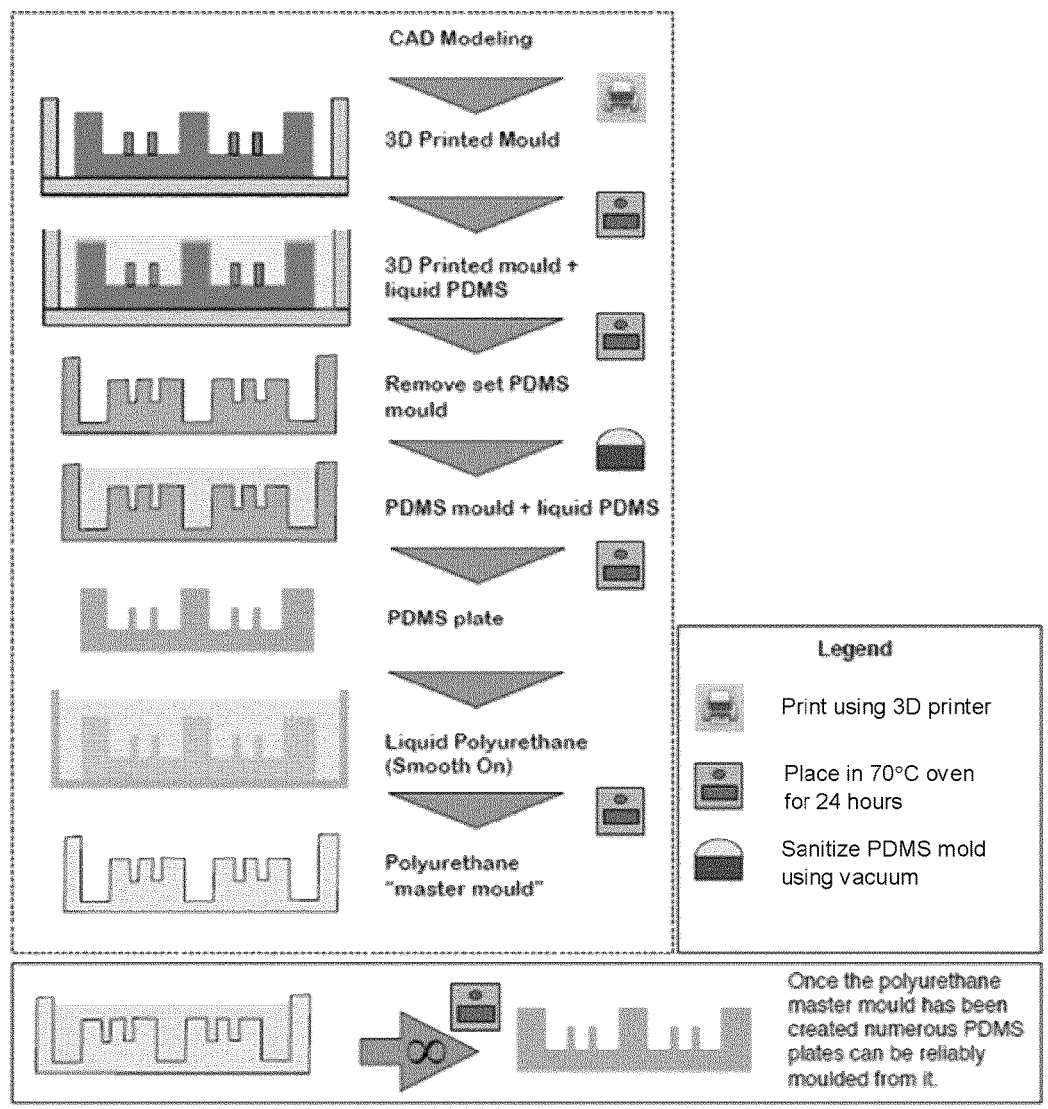

FIG. 6(f) illustrates an example 3D printing method for the microfabrication of a microplate having microwells with tissue microfabrication platforms integrally formed therein.

Figure 6G:
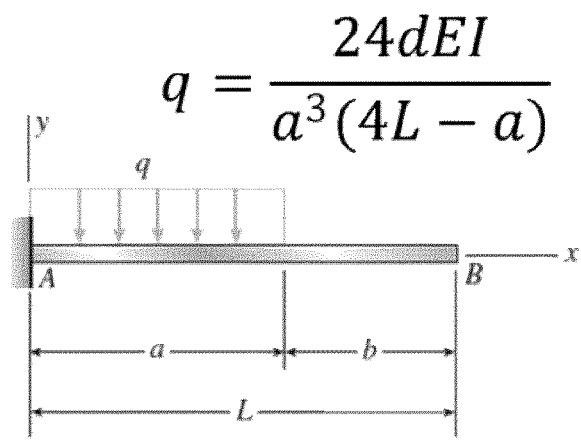

FIG. 6(g) depicts the equation used to determine the force per unit length in example microfabrication platforms disclosed herein.

Figure 6H:
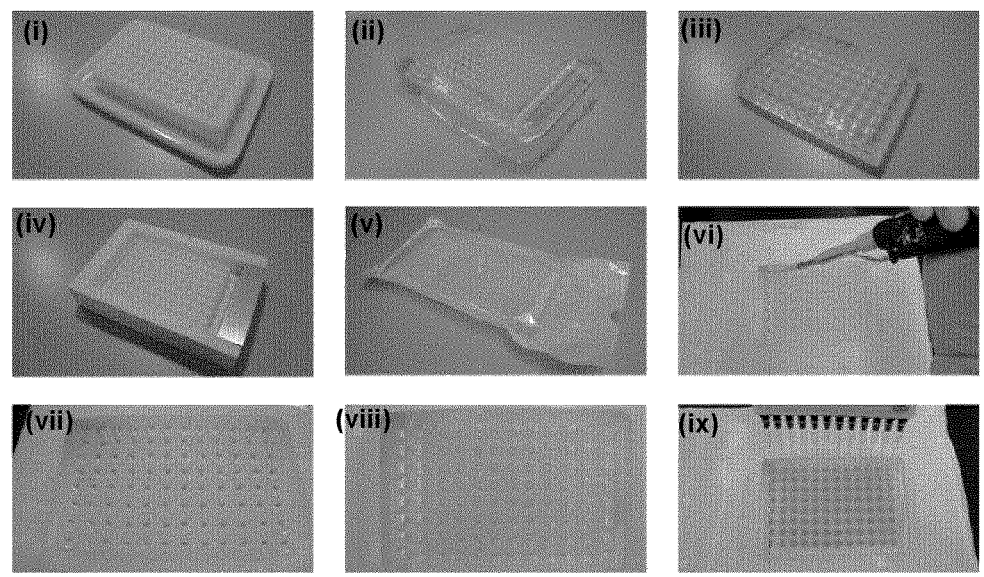

FIG. 6(h) illustrates an example method of producing a replica microplate based on a master microplate mold formed via 3D printing.

Figure 6I:
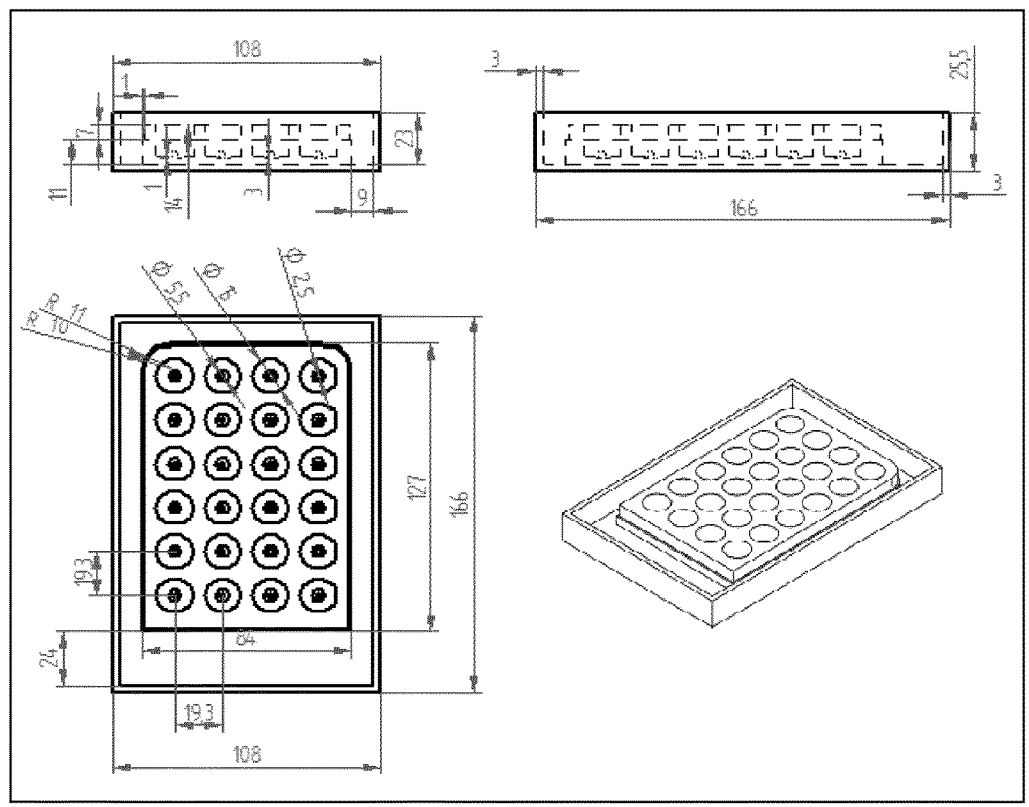
Figure 6J:
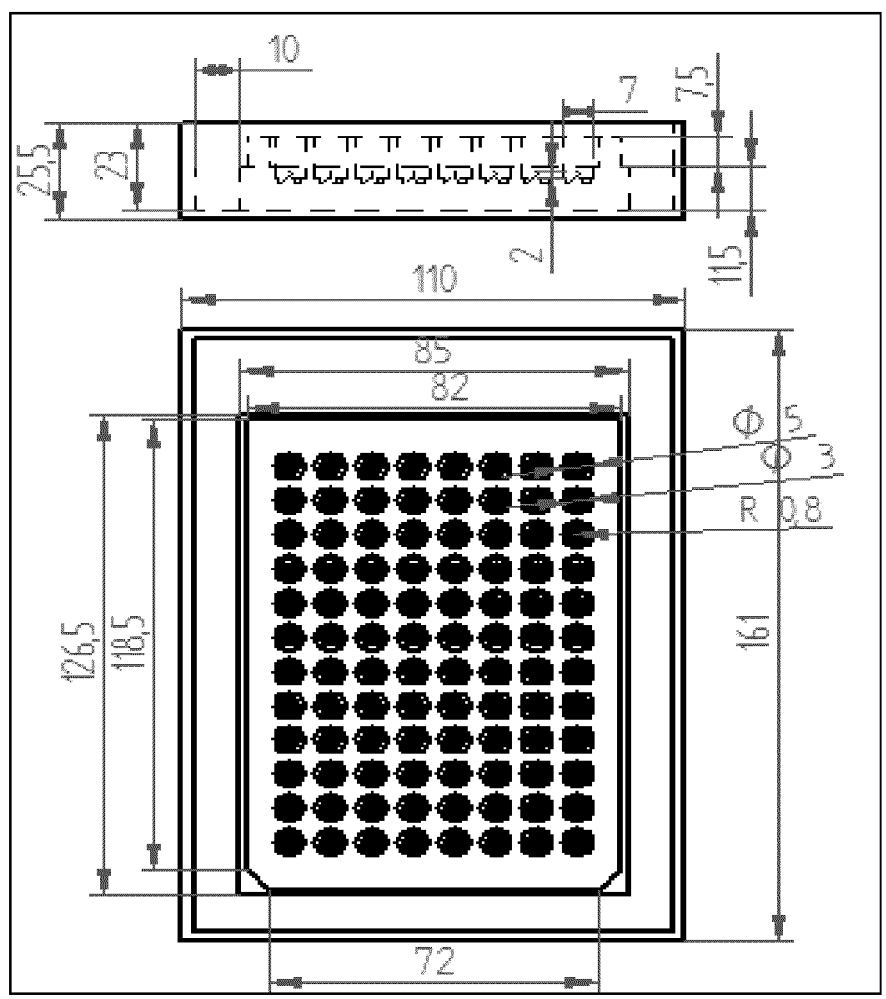
Figure 7A:
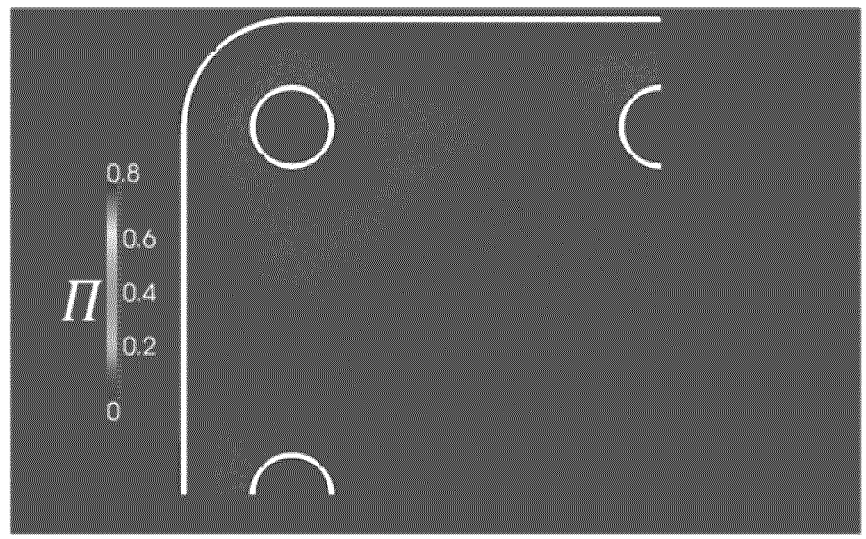
Figure 7B:
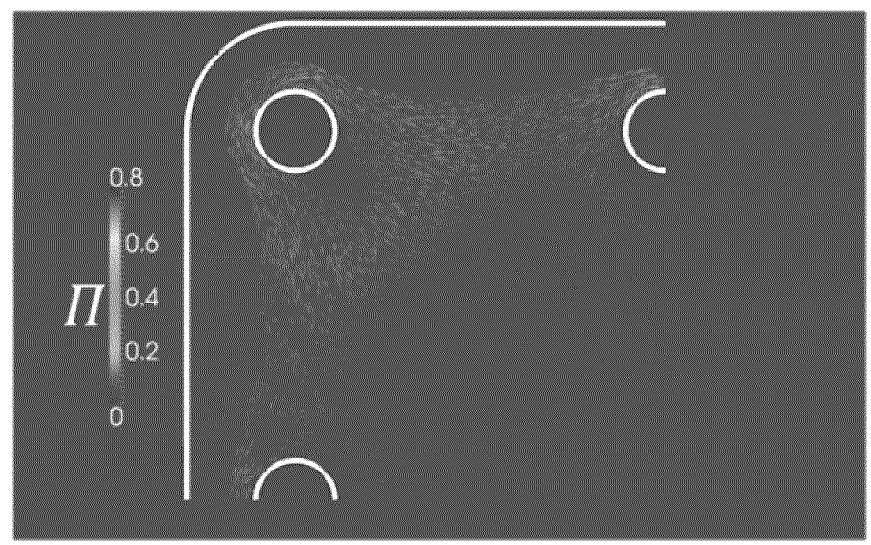
Figure 7C:
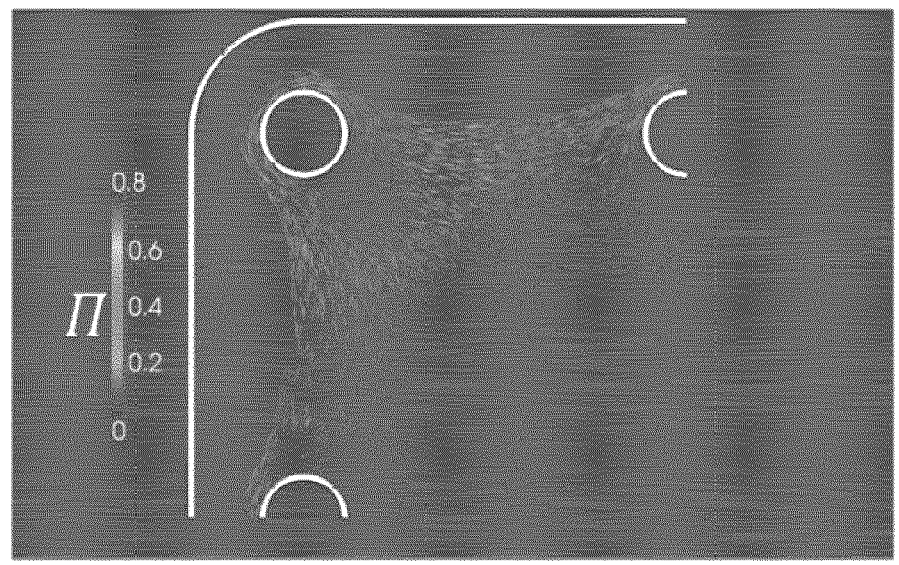
Figure 7D:
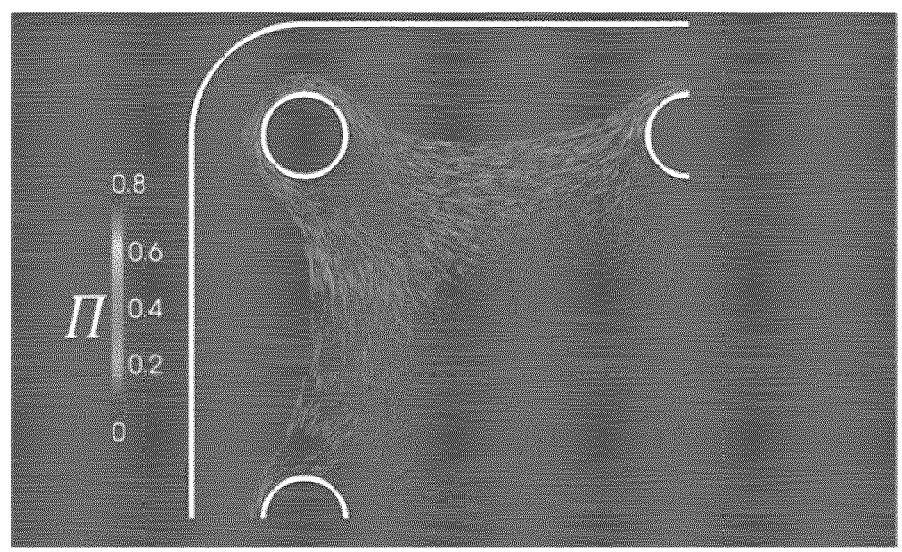
Figure 7E:
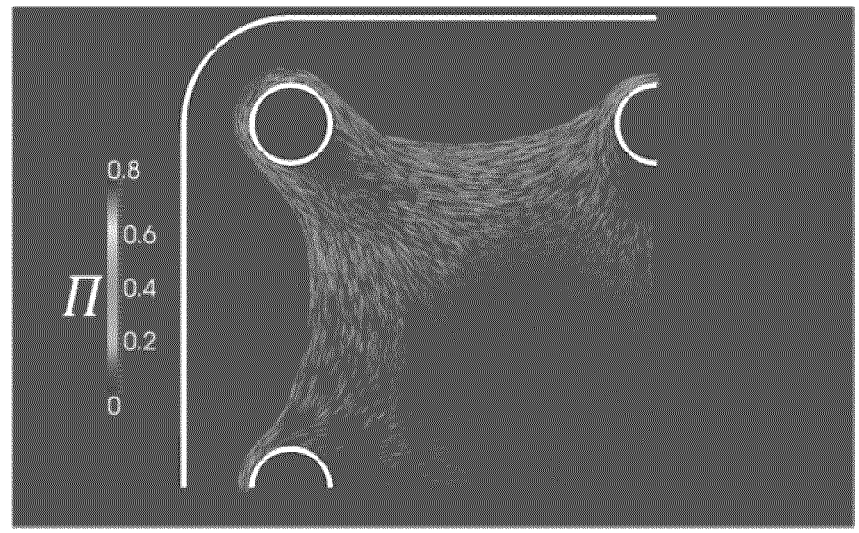
Figure 7F:
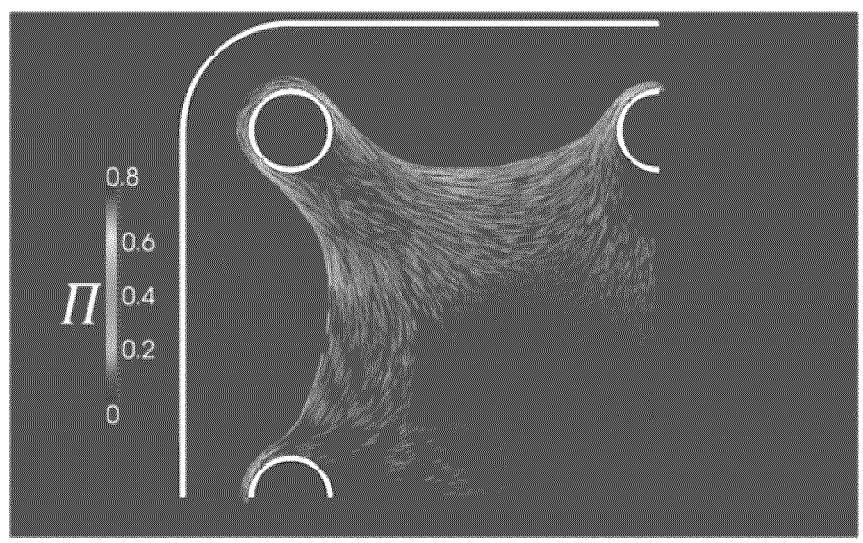
Figure 7G:
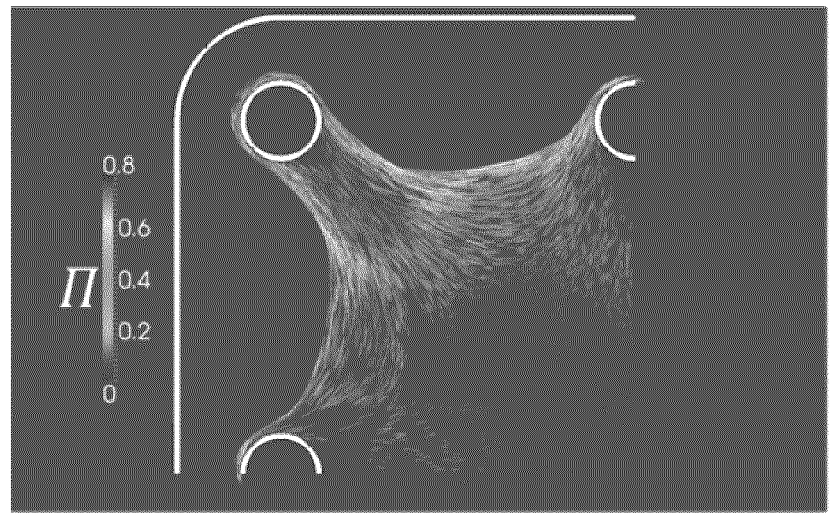
Figure 7H:
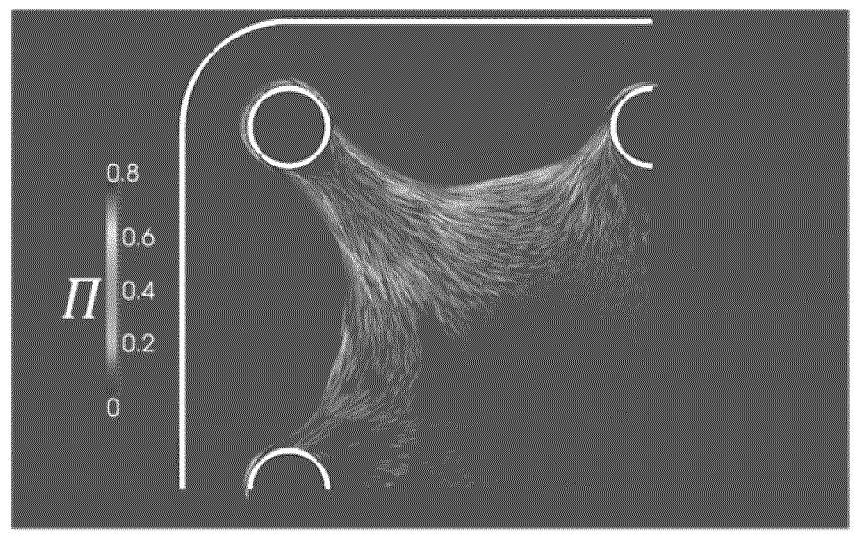
Figure 8A:
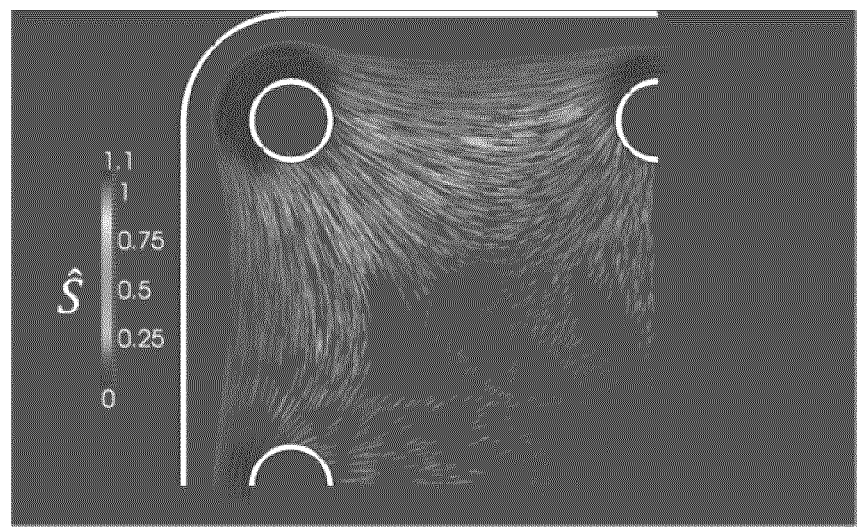
Figure 8B:
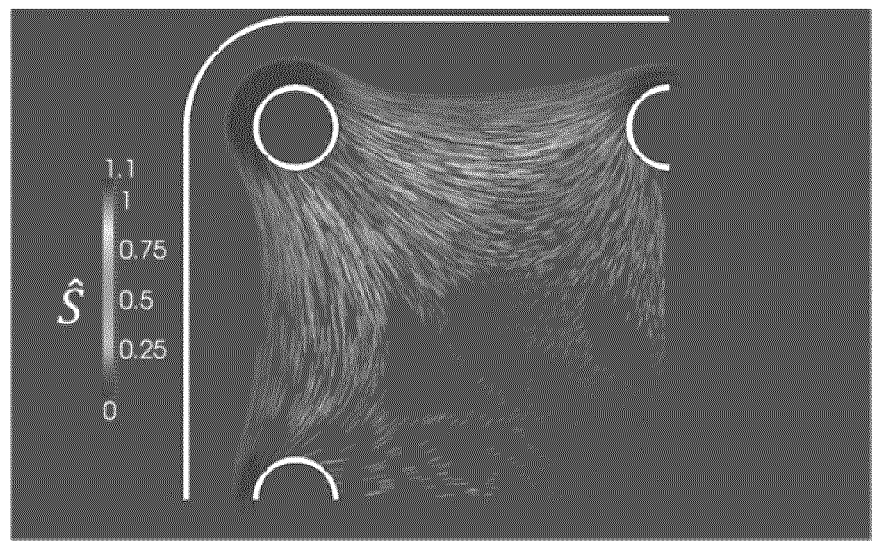
Figure 8C:
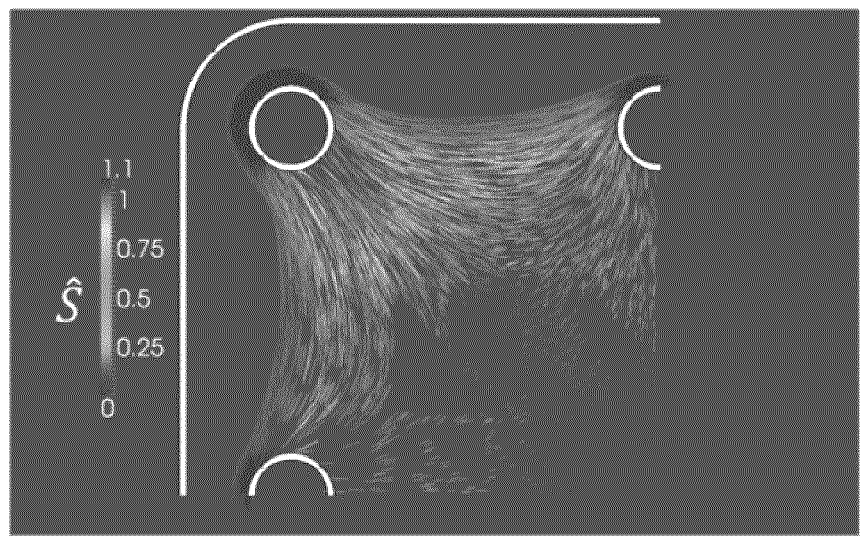
Figure 8D:
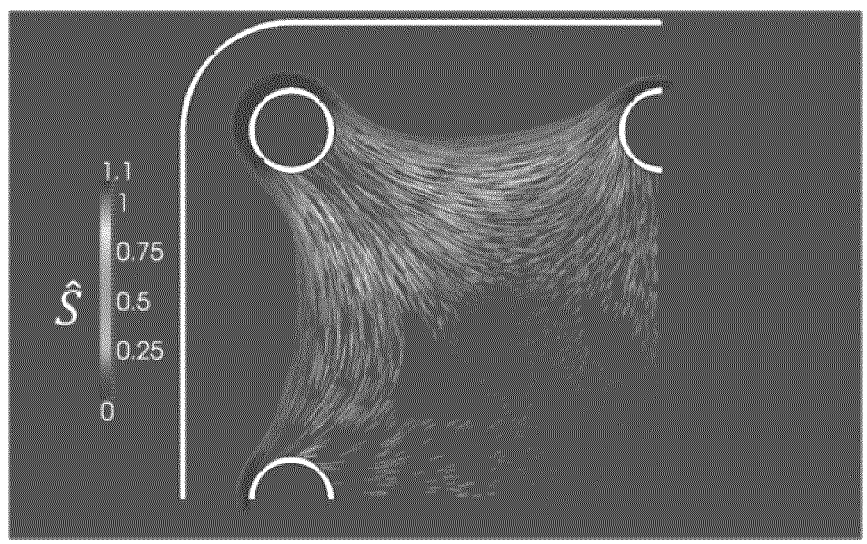
Figure 8E:
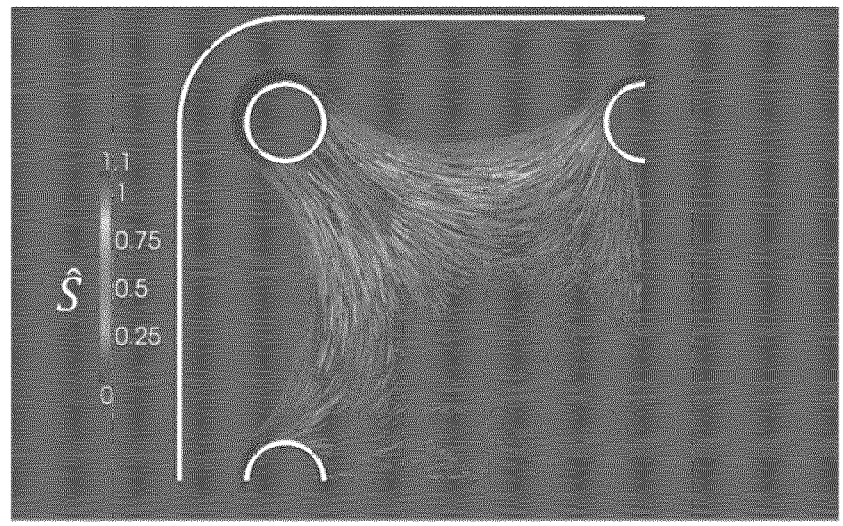
Figure 8F:
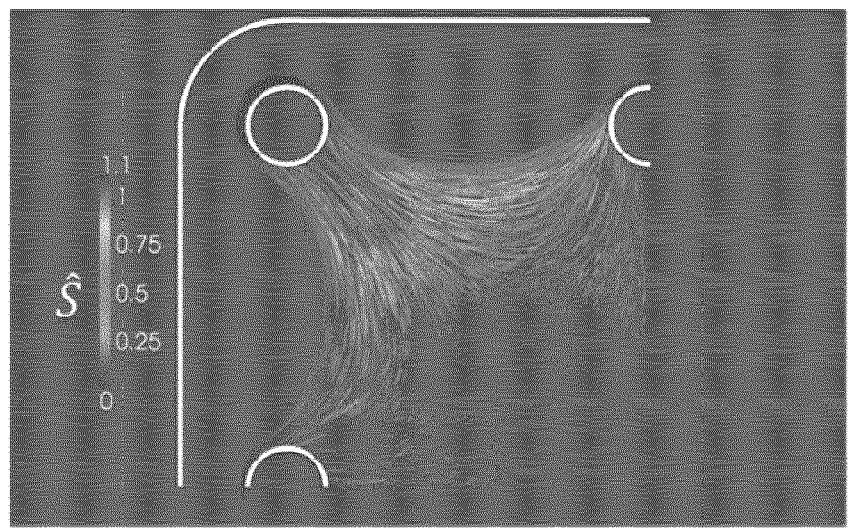
Figure 8G:
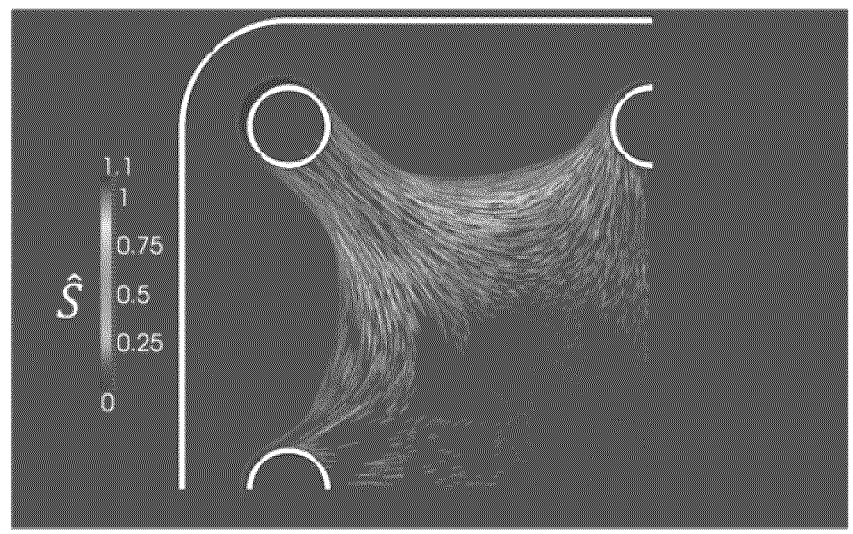
Figure 8H:
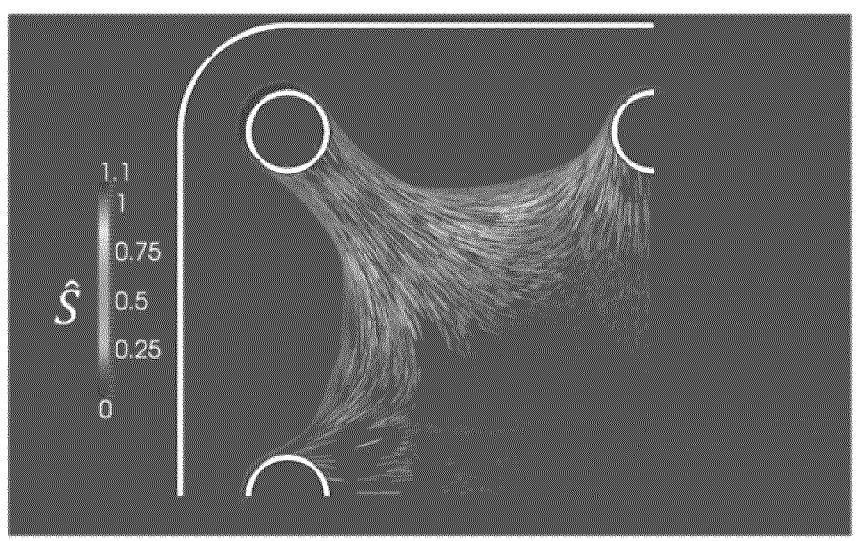
Figure 9A:
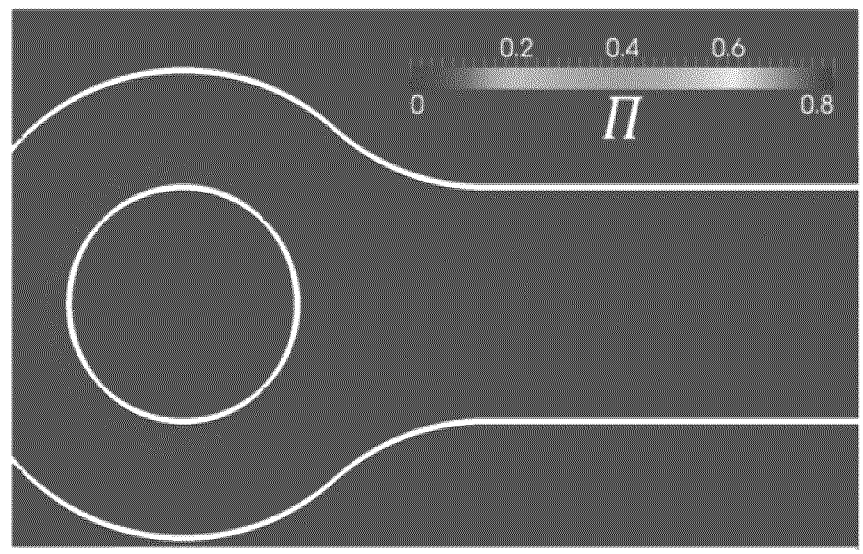
Figure 9B:
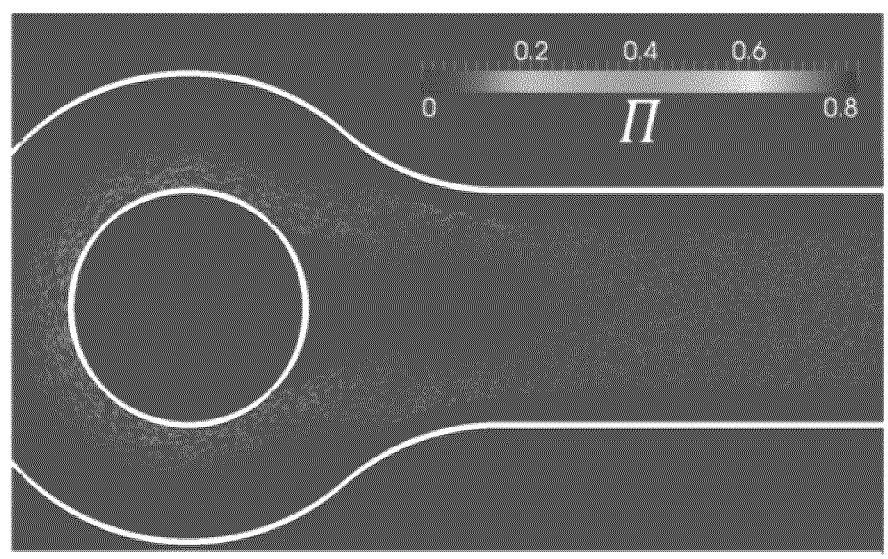
Figure 9C:
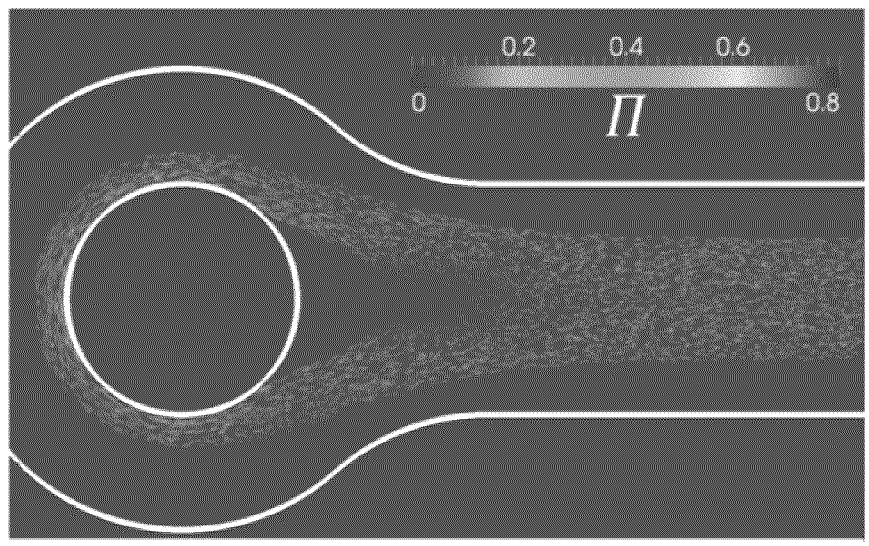
Figure 9D:
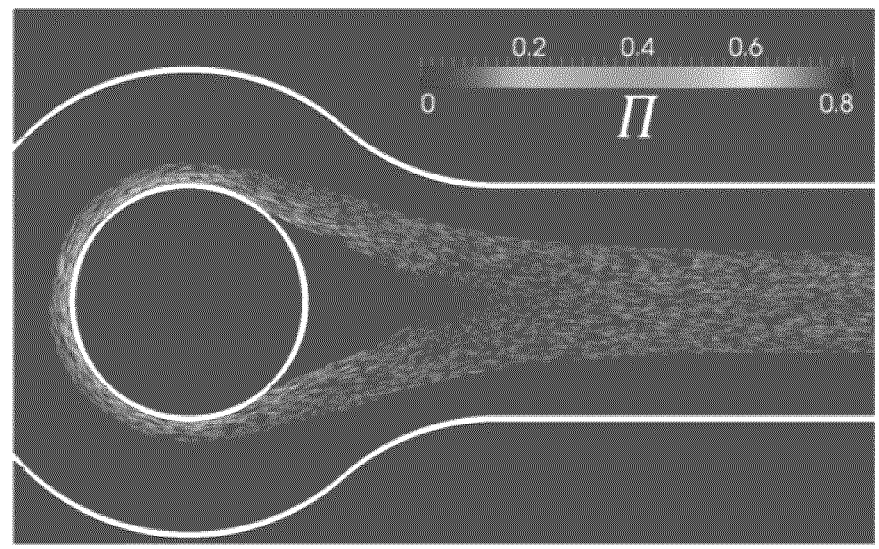
Figure 9E:
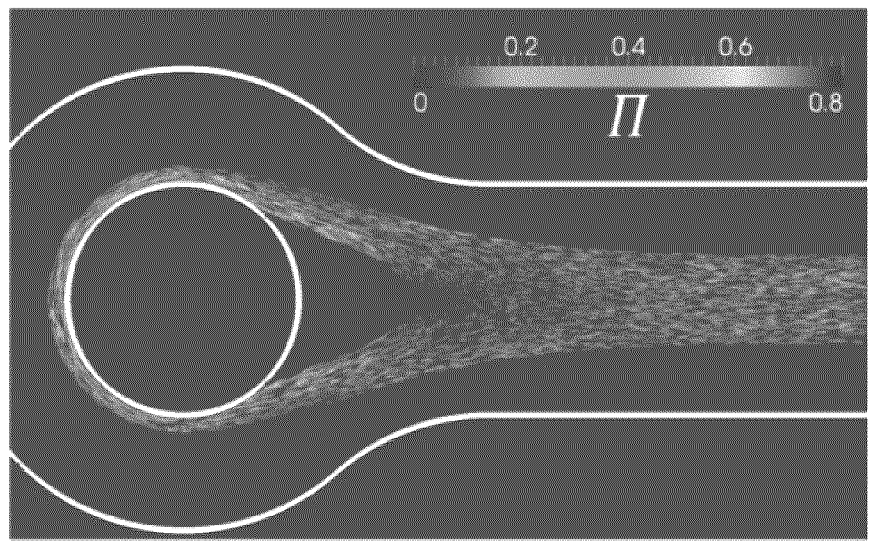
Figure 9F:
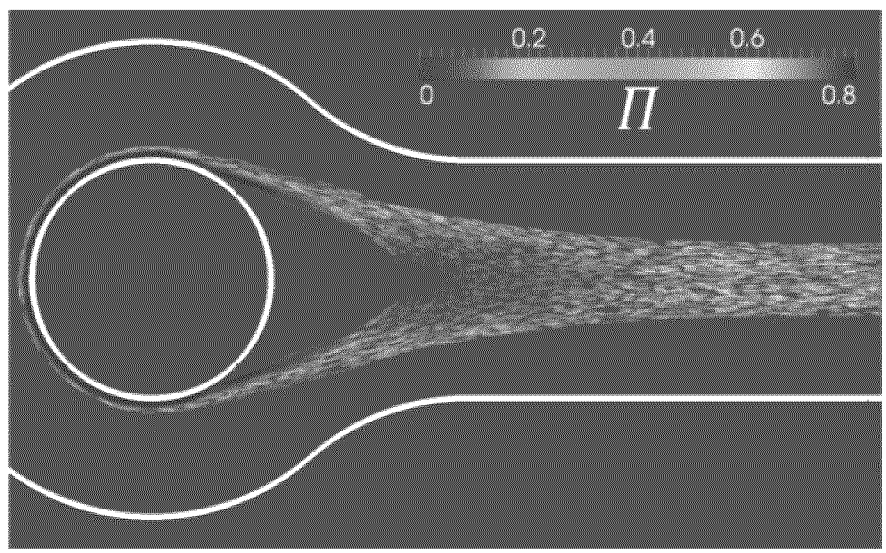
Figure 10A:
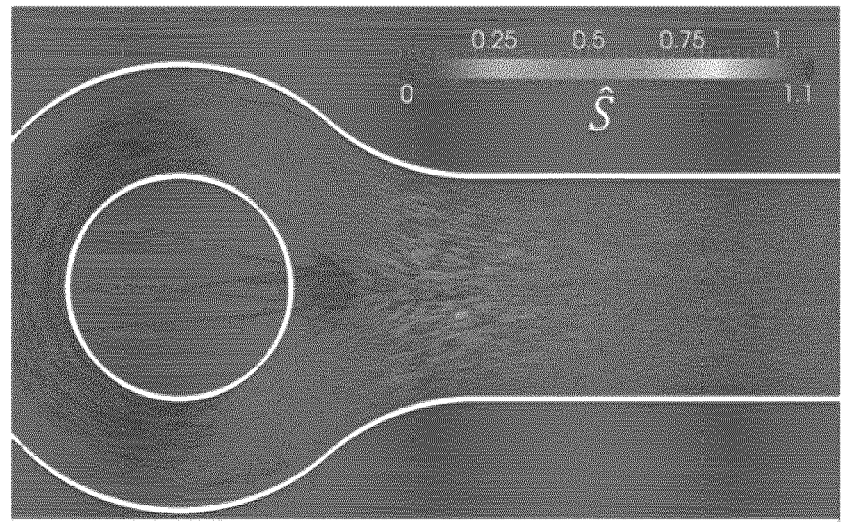
Figure 10B:
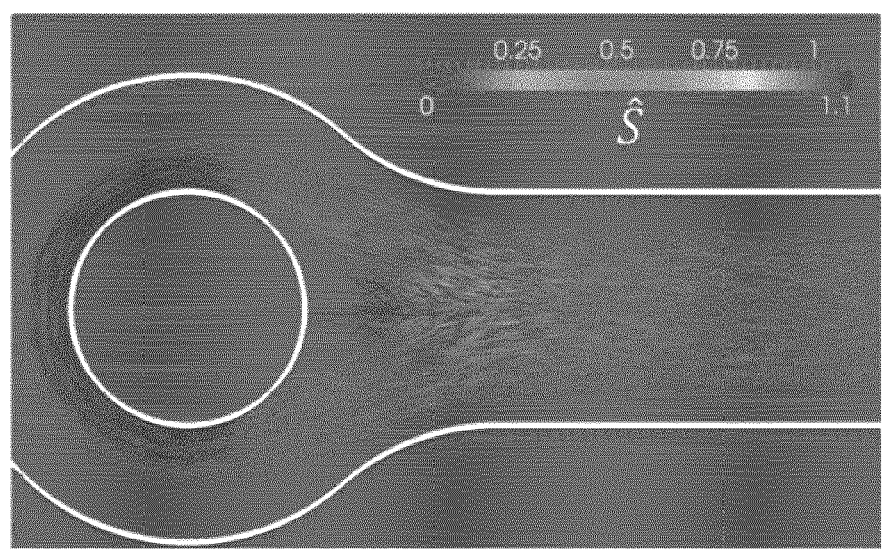
Figure 10C:
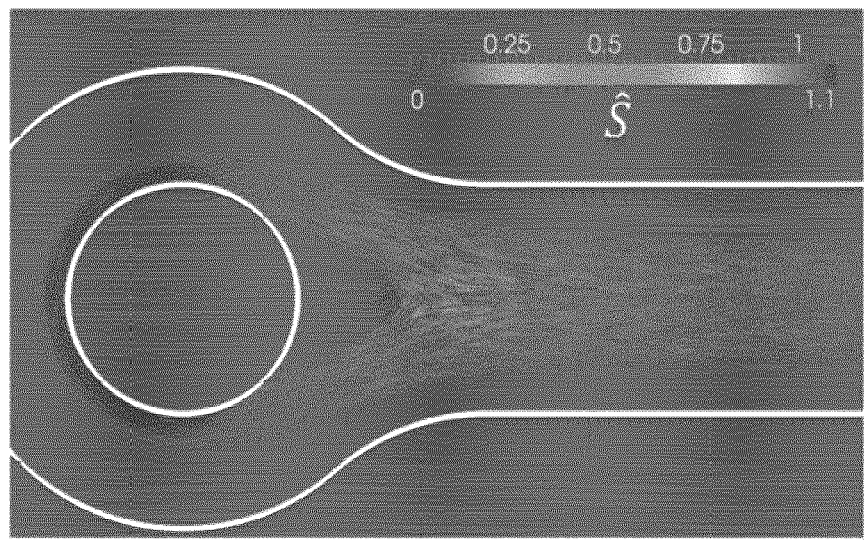
Figure 10D:
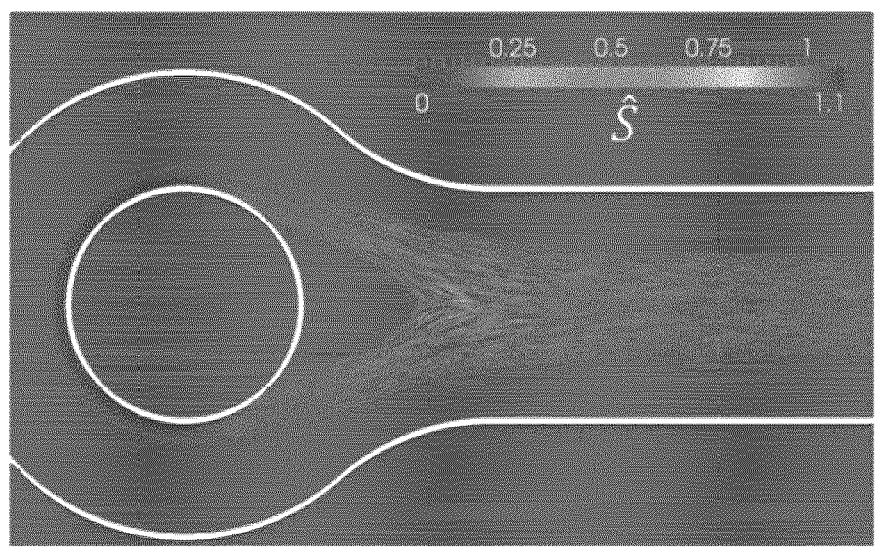
Figure 10E:
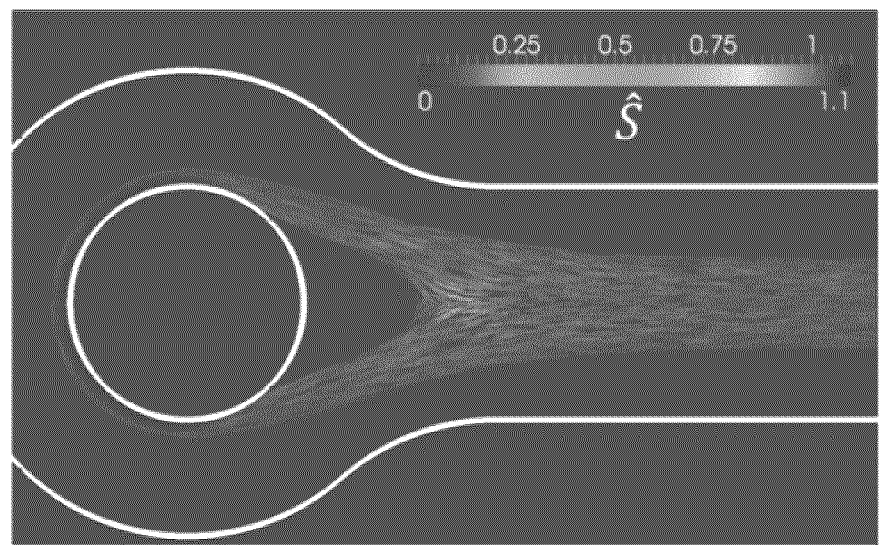
Figure 10F:
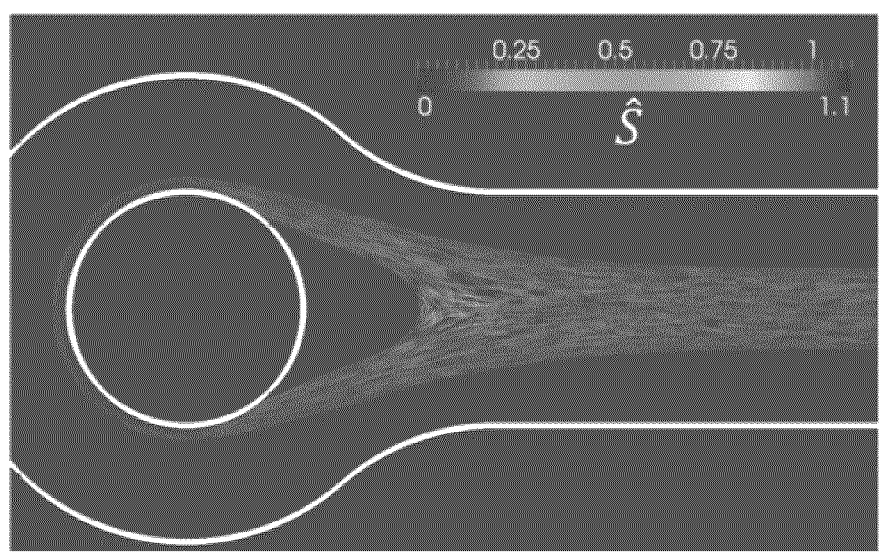

FIGS. 6(i) and 6(j) show example designs of a 24-microwell and a 96-microwell microplate.

FIGS. 7 (a)-(h) show the calculated distribution and alignment of sarcomeres in the biaxial tissue at a number of time-points following signal initiation, at times t/θ=0: (a) t/θ=0.8; (b) t/θ=1.4; (c) t/θ=1.9; (d) t/θ=2.5; (e) t/θ=3.1; (f) t/θ=4.2; (g) t/θ=5.9; (h) t/θ=10.0. The quantity $\Pi=(\eta_{max}-\eta)$ is indicated by the vector shade and vector length. The vector orientation indicates the orientation of $\eta_{max}$, (the direction of the dominant sarcomere formation) at all points in the tissue. The solid white outline in the top plot indicates the initial non-deformed tissue geometry.

FIGS. 8 (a)-(h) show the calculated distribution of the non-dimensional effective stress $\hat{S}$ in the biaxial tissue at a number of time-points following signal initiation at time $t/\theta=0$: (a) $t/\theta=0.8$; (b) $t/\theta=1.4$; (c) $t/\theta=1.9$; (d) $t/\theta=2.5$; (e) $t/\theta=3.1$; (f) $t/\theta=4.2$; (g) $t/\theta=5.9$; (h) $t/\theta=10.0$. $\hat{S}=(\sigma_{max}^P-\sigma_{min}^P)/\sigma_{max}^P$, where $\sigma_{max}^P$ and $\sigma_{min}^P$ are the maximum and minimum principal stresses, respectively. The magnitude of $\hat{S}$ is indicated by the vector shade and vector length. The vector orientation indicates the maximum principal direction, i.e. the orientation of $\sigma_{max}^P$. The solid white outline in the top plot indicates the initial non-deformed tissue geometry.

FIGS. 9 (a)-(f) show the calculated distribution and alignment of sarcomeres in the uniaxial tissue at a number of time-points following signal initiation at time $t/\theta=0$: (a) $t/\theta=0.6$; (b) $t/\theta=1.2$; (c) $t/\theta=2.9$; (d) $t/\theta=4.6$; (e) $t/\theta=5.8$; (f) $t/\theta=10.0$. The quantity $\Pi=(\eta_{max}-\overline{\eta})$ is indicated by the vector shade and vector length. The vector orientation indicates the orientation of $\eta_{max}$, (the direction of the dominant sarcomere formation) at all points in the tissue. The solid white outline in the top plot indicates the initial non-deformed tissue geometry.

FIGS. 10 (a)-(f) show the calculated distribution of the non-dimensional effective stress $\hat{S}$ in the biaxial tissue at a number of time-points following signal initiation at time $t/\theta=0$: (a) $t/\theta=0.6$; (b) $t/\theta=1.2$; (c) $t/\theta=2.9$; (d) $t/\theta=4.6$; (e) $t/\theta=5.8$; (f) $t/\theta=10.0$. $\hat{S}=(\sigma_{max}^P-\sigma_{min}^P)/\sigma_{max}^P$, where $\sigma_{max}^P$ and $\sigma_{min}^P$ are the maximum and minimum principal stresses, respectively. The magnitude of $\hat{S}$ is indicated by the vector shade and vector length. The vector orientation indicates the maximum principal direction, i.e. the orientation of $\sigma_{max}^P$. The solid white outline in the top plot indicates the initial non-deformed tissue geometry.

Figure 11A:
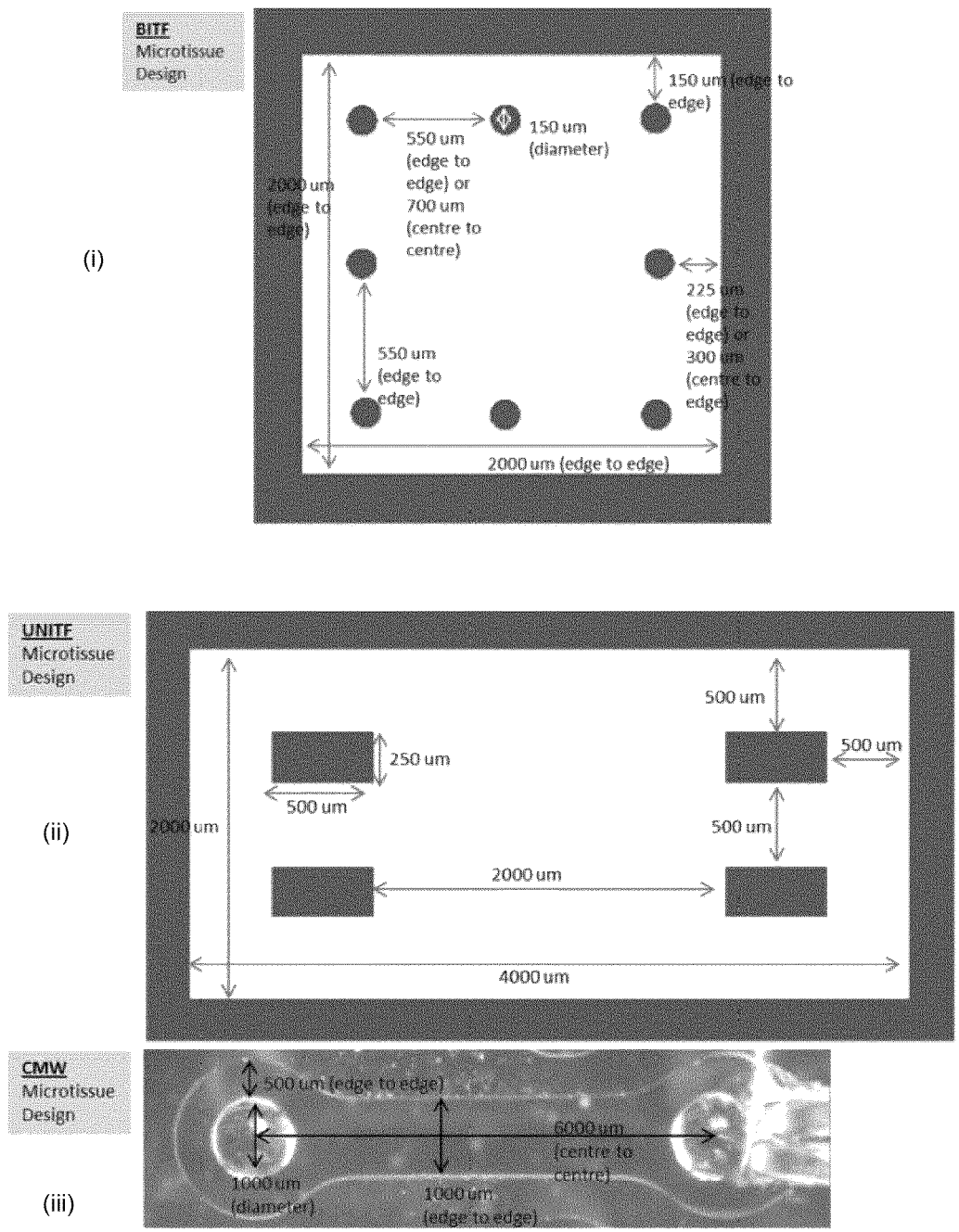
Figure 11B:
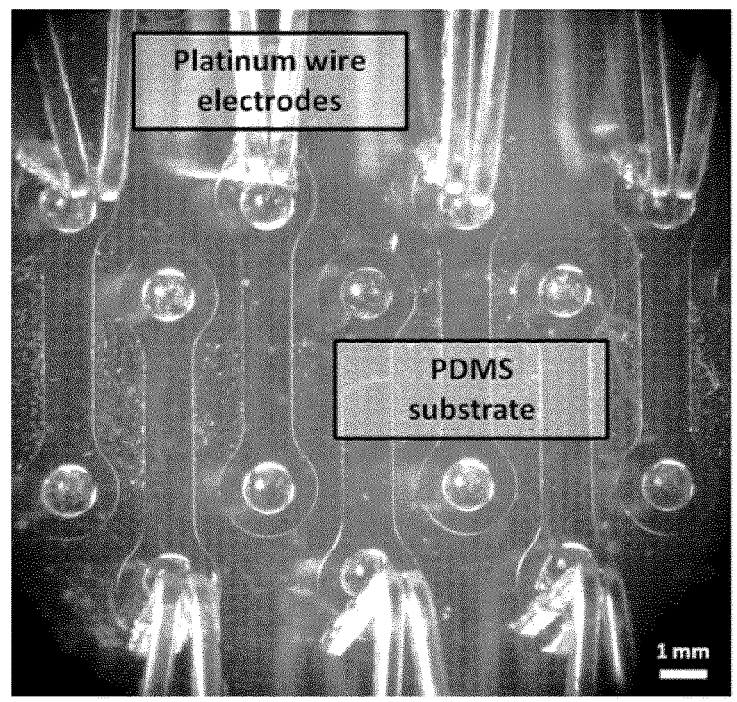
Figure 11C:

FIGS. 11 (a)-(c) show designs of microfabricated platforms for generating, cultivating, and assaying microtissues. FIG. 11(a) shows substrate dimensions for microtissue seeding platforms, where uniaxial tension force microtissues (UNITF) exhibit increased cell elongation and cell alignment compared to biaxial tension force microtissues (BITF) (i) and CMW (iii). FIGS. 11(b) (close-up of single well) and (c) (partial 24-well plate image) show a 24-well cardiac bioreactor platform composed of platinum wire electrodes embedded in a microfabricated substrate is used to contain cardiac microwire from the point of seeding to cultivation to assaying.

Figures 12A, 12B:
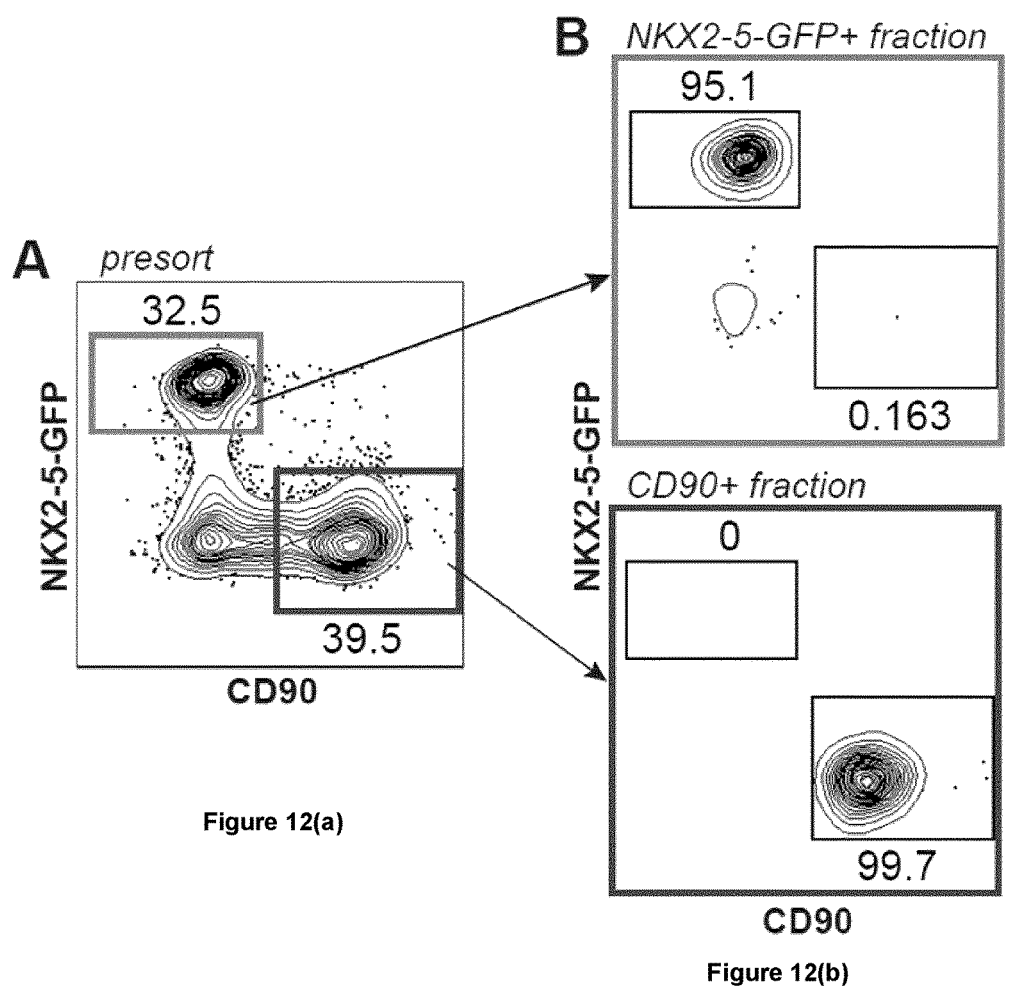

FIGS. 12 (a) and (b) show flow cytometry cell sorting plots of NKX2-5 and CD90 mixing experiments, where (a) shows fluorescent-activated cell sorting of day 20 embryonic stem cell-derived embryoid bodies (EBs; EBs were dissociated and sorted for NKX2-5-GFP+ and CD90+ fractions), and where (b) shows purity control of NKX2-5-GFP+ and CD90+ sorted fractions.

Figure 13:
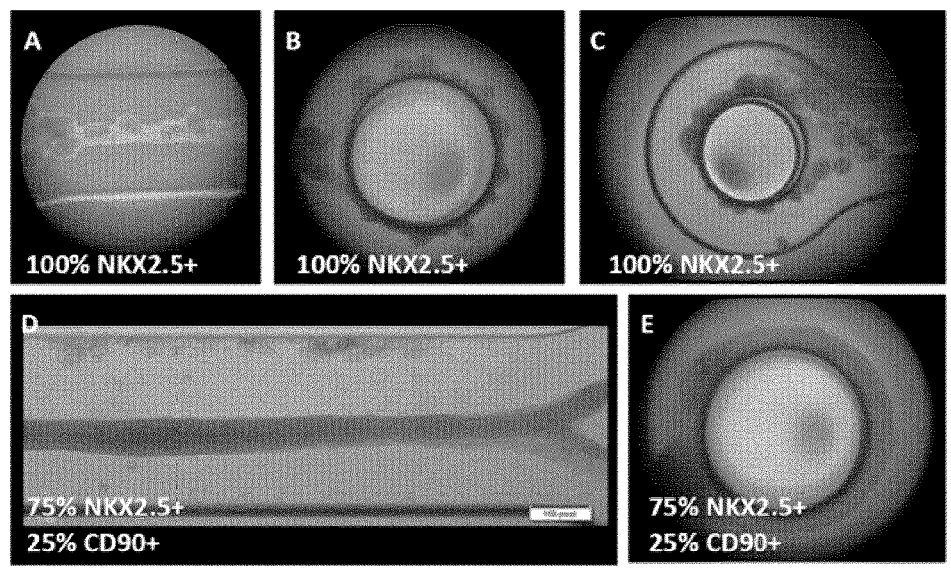

FIGS. 13 (a)-(e) shows morphology of cardiac microwire (at day 14) composed of [100% NKX2-5+] cells (a-c) and [75% NKX2-5 and 25% CD90+] cells (d-e).

Figure 14A:
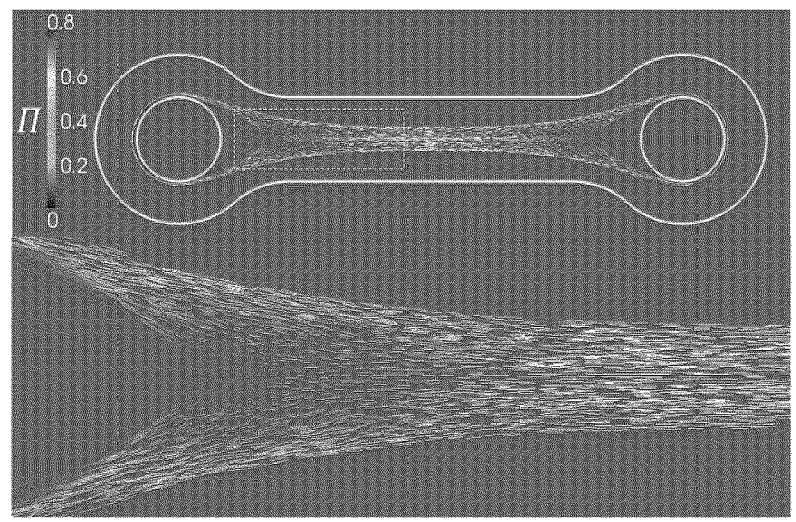

FIG. 14(a) shows the distribution and alignment of sarcomeres (a) in the uniaxial tissue at steady state ($t/\theta=10.0$). The quantity $\Pi=(\eta_{max}-\overline{\eta})$ is indicated by the vector shade and vector length. The vector orientation indicates the orientation of $\eta_{max}$, (the direction of the dominant sarcomere formation) at all points in the tissue. [Note that short vectors indicate a low value of $\Pi$, signifying that significant formation of aligned sarcomeres occurs. On the other hand, long vectors signify that significant formation of aligned sarcomeres occurs in dominant directions that are indicated by the vector orientations]. The solid white outline in the top plot indicates the initial underformed tissue geometry. The hatched line indicates the region that is magnified for clarity in the bottom plot. The model was based on typical neonatal rat CM isolation populations which consist of ~75-80% cardiomyocytes and ~20-25% fibroblasts.

Figure 14B:
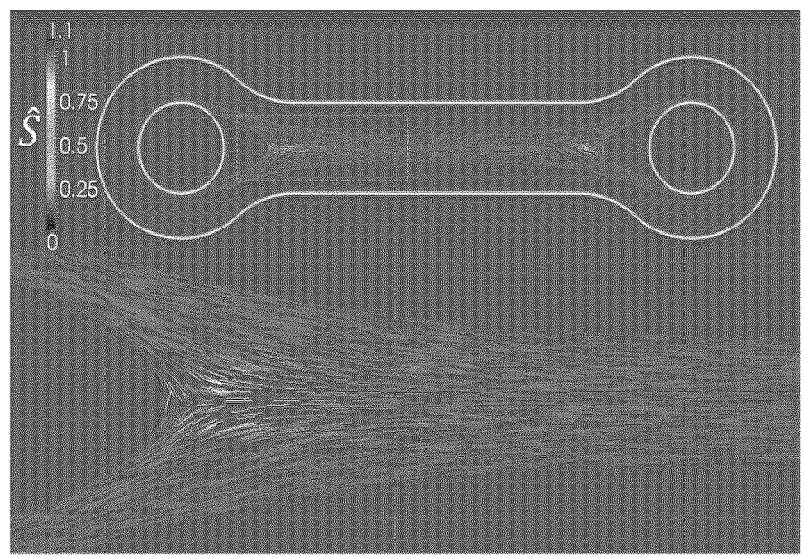

FIG. 14(b) shows the distribution of the non-dimensional effective stress $\hat{S}$ in the uniaxial tissue at steady state ($t/\theta=10.0$). $\hat{S}=(\sigma_{max}^P-\sigma_{min}^P)/\sigma_{max}^P$, where $\sigma_{max}^P$ and $\sigma_{min}^P$ are the maximum and minimum principal stresses, respectively. The magnitude of $\hat{S}$ is indicated by the vector shade and vector length. The vector orientation indicates the maximum principal direction, i.e. the orientation of $\sigma_{max}^P$. [Note that short vectors indicate a low value of $\hat{S}$, signifying that the stress state is largely biaxial in nature (for a perfectly bi-axial stress state $\sigma_{max}^P=\sigma_{min}^P$ so that $\hat{S}=0$). On the other hand, long vectors signify a high value of $\hat{S}$, signifying that the stress state is not at all biaxial in nature, rather it is tending towards a uniaxial stress state. If $\hat{S}=1$ the stress state is perfectly uniaxial, with $\sigma_{min}^P=0$. Note that the minimum principal stress can become negative due to the passive compressive deformation of the ECM. Hence, values of $\hat{S}>1$ can be computed. However, such passive compressive stresses are small compared to the active stresses generated by the cells, so the highest value of $\hat{S}$ computed in the tissue does not significantly exceed unity (~1.2)]. The solid white outline in the top plot indicates the initial undeformed tissue geometry. The hatched line indicates the region that is magnified for clarity in the bottom plot.

Figure 15A:
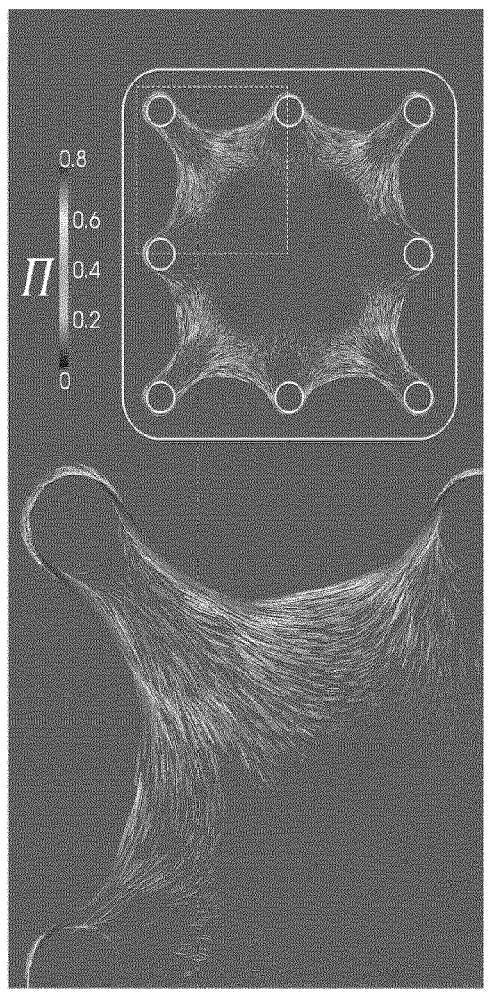

FIG. 15(a) shows the distribution and alignment of sarcomeres in the biaxial tissue at steady state ($t/\theta=10.0$). The quantity $\Pi=(\eta_{max}-\overline{\eta})$ is indicated by the vector shade and vector length. The vector orientation indicates the orientation of $\eta_{max}$, (the direction of the dominant sarcomere formation) at all points in the tissue. [Note that short vectors indicate a low value of $\Pi$, signifying that significant formation of aligned sarcomeres occurs. On the other hand, long vectors signify that significant formation of aligned sarcomeres occurs in dominant directions that are indicated by the vector orientations]. The solid white outline in the top plot indicates the initial underformed tissue geometry. The hatched line indicates the region that is magnified for clarity in the bottom plot.

Figure 15B:
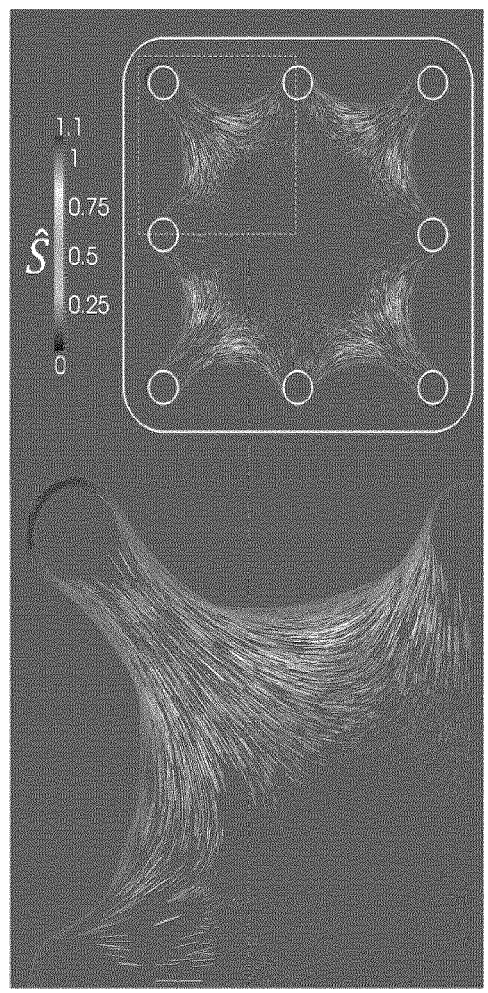

FIG. 15(b) shows the distribution of the non-dimensional effective stress $\hat{S}$ in the biaxial tissue at steady state ($t/\theta=10.0$). $\hat{S}=(\sigma_{max}^P-\sigma_{min}^P)/\sigma_{max}^P$, where $\sigma_{max}^P$ and $\sigma_{min}^P$ are the maximum and minimum principal stresses, respectively. The magnitude of $\hat{S}$ is indicated by the vector shade and vector length. The vector orientation indicates the maximum principal direction, i.e. the orientation of $\sigma_{max}^P$. [Note that short vectors indicate a low value of $\hat{S}$, signifying that the stress state is largely biaxial in nature (for a perfectly bi-axial stress state $\sigma_{max}^P=\sigma_{min}^P$ so that $\hat{S}=0$). On the other hand, long vectors signify a high value of $\hat{S}$, signifying that the stress state is not at all biaxial in nature, rather it is tending towards a uniaxial stress state. If $\hat{S}=1$ the stress state is perfectly uniaxial, with $\sigma_{min}^P=0$. Note that the minimum principal stress can become negative due to the passive compressive deformation of the ECM. Hence, values of $\hat{S}>1$ can be computed. However, such passive compressive stresses are small compared to the active stresses generated by the cells, so the highest value of $\hat{S}$ computed in the tissue does not significantly exceed unity (~1.2)]. The solid white outline in the top plot indicates the initial undeformed tissue geometry. The hatched line indicates the region that is magnified for clarity in the bottom plot.

FIGS. 16(a)-(g) show various example cantilever designs having a general layout of dual posts within a well.

FIGS. 17(a)-(f) show embodiments of microtissue formation using various post geometries.

FIGS. 18 (a) to (d) shows post deflection as captured in still images from a video file, where (a) shows a field view of cardiac tissue attached to posts, pre-deflection; (b) shows the same field view as in (a) post-deflection; (c) and (d) show close-ups of the posts in (a) and (b), respectively. The arrow is in the same position in the field image in both (c) and (d).

Figure 19:
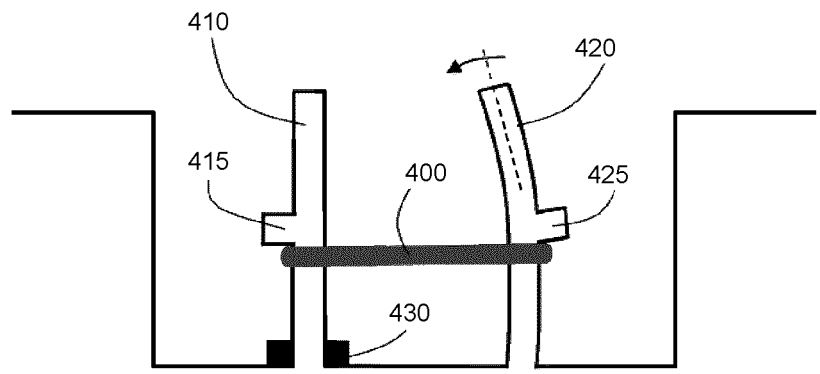

FIG. 19 is an illustration of an example cantilever dual-post embodiment where both posts have protuberances. One post having integrated electrodes is rigidly maintained while the second post is capable of flexing.

Figure 20:
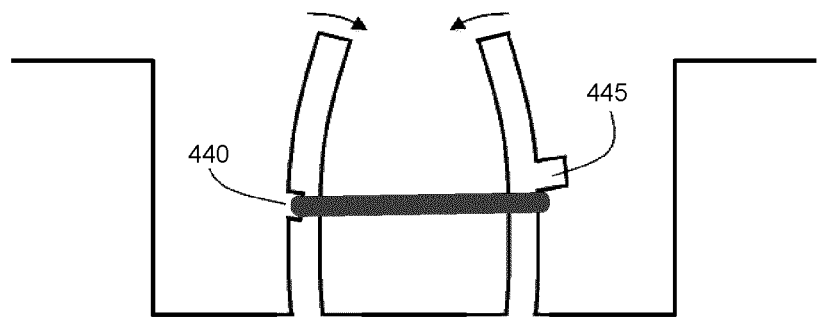

FIG. 20 is an illustration of an example cantilever dual-post embodiment where one post has a protuberance and the second post a groove. Both posts are capable of flexing.

Figure 21:
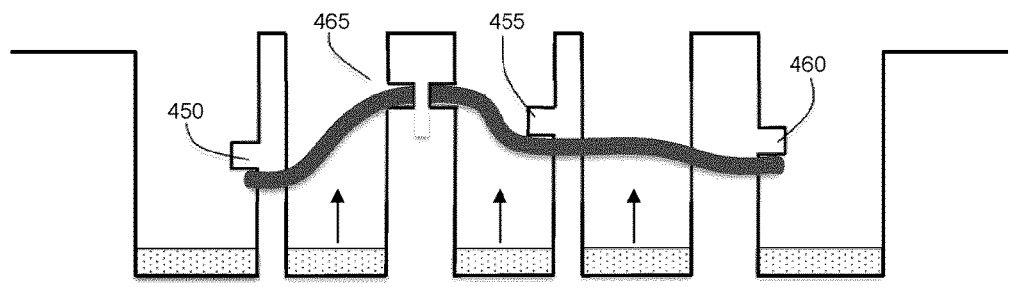

FIG. 21 is an illustration of an example cantilever multi-post embodiment combining protuberance-containing and groove-containing features. The combination of retaining features is used to control tissue formation.

Figure 22A:
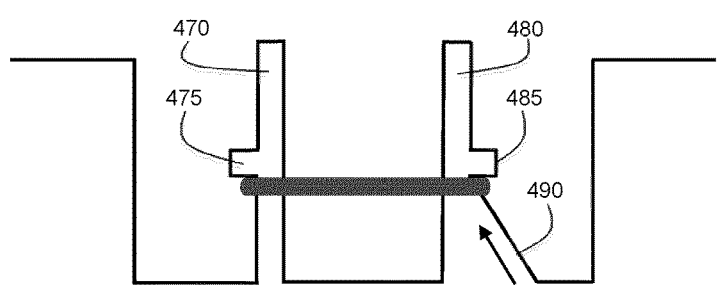

FIG. 22(a) is an illustration of an example cantilever dual-post embodiment in which both posts have protuberances but one post is straight while the second post is ramped.

Figure 22B:
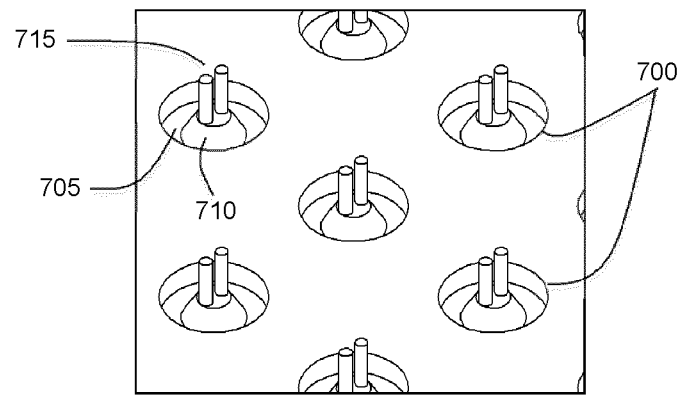

FIGS. 22(b) and (c) are illustrations of an array of microwells having microfabrication platforms including a ramped support structure supporting two retaining structures.

Figure 22C:
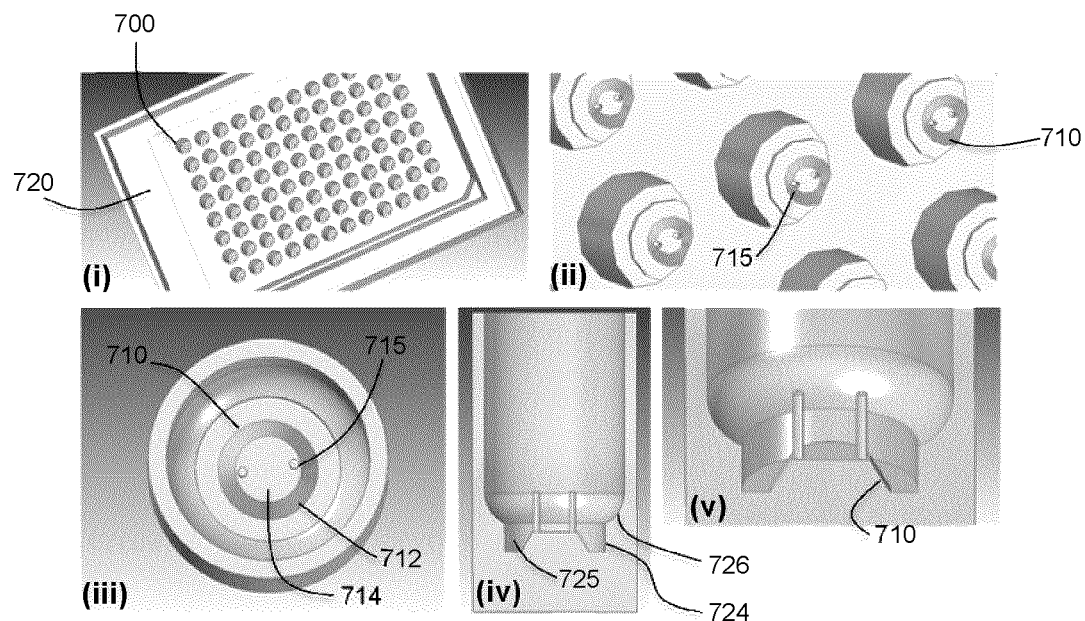
Figure 22D:
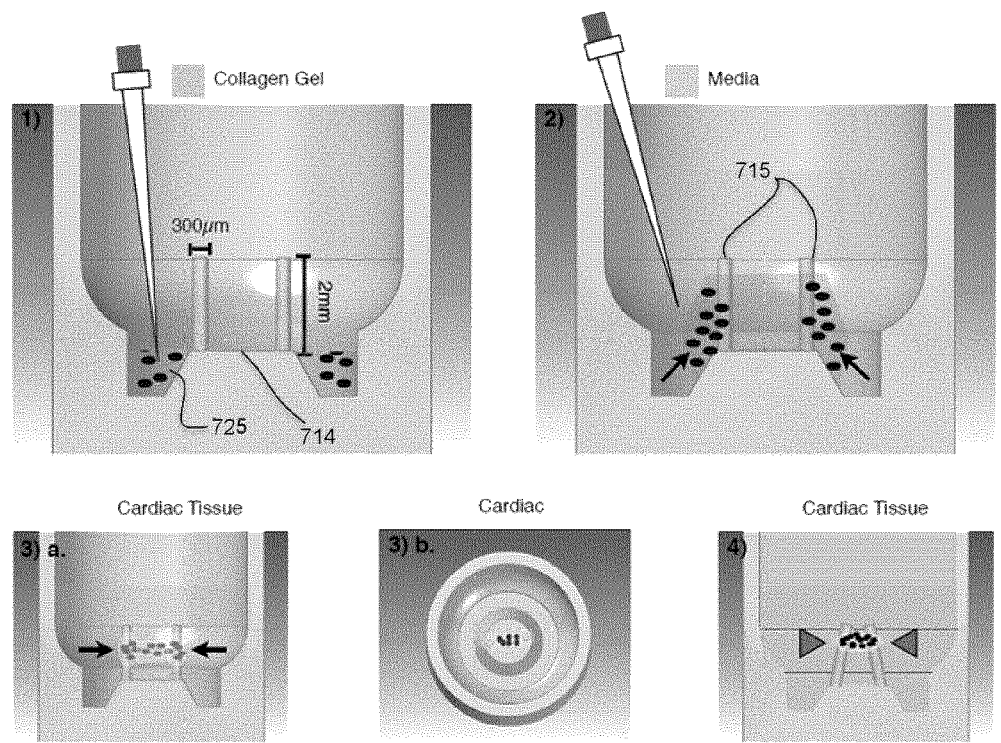

FIG. 22(d) illustrates an example method of forming a tissue construct within a microwell having a microfabrication platform including a ramped support structure supporting two retaining structures.

Figure 22E:
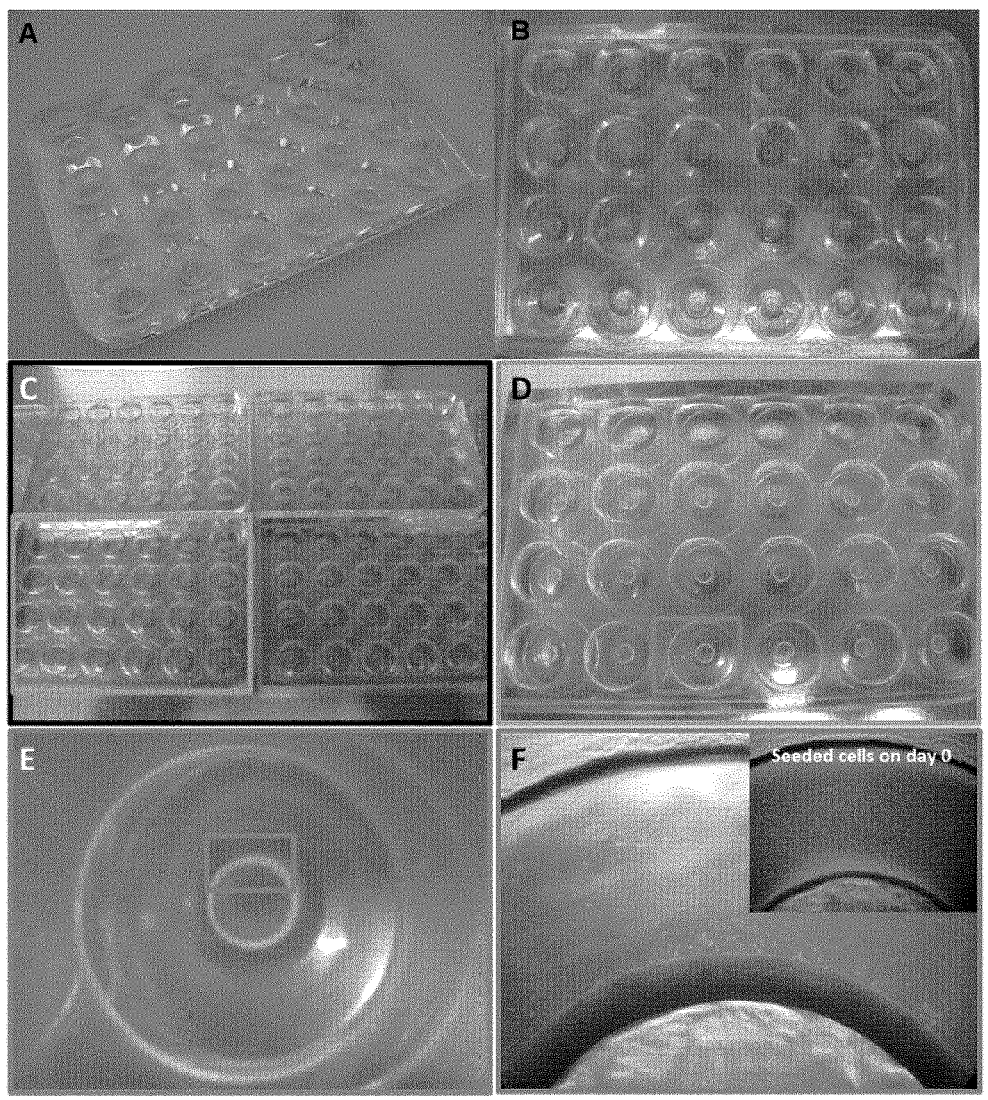

FIG. 22(e) is a series of photographs demonstrating an example process flow of tissue micro-ring generation (A-F).

Figure 22F:
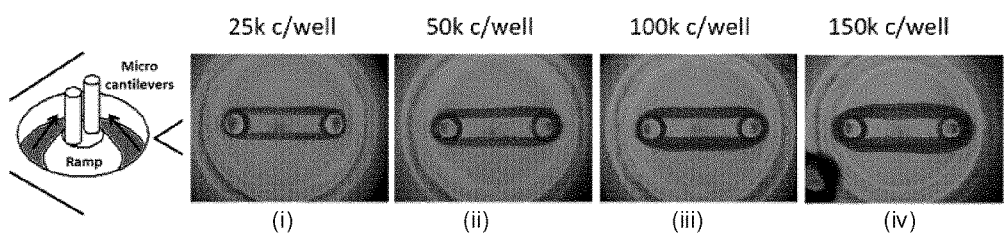

FIGS. 22(f)(i)-(iv) includes a series of photographs and microscopy images illustrating the effect of the number of cells employed in cell seeding.

Figure 22G:
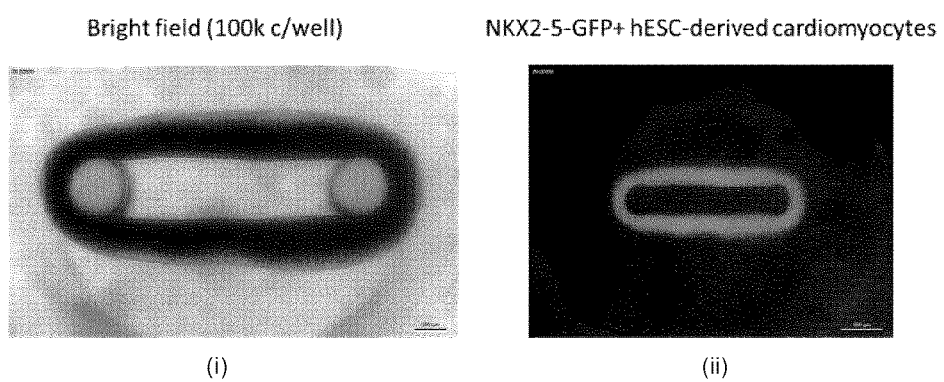

FIGS. 22(g)(i)-(ii) depict micrographs of spontaneously contracting cardiac microtissues within the system, where (i) shows 100,000 cells per well under brightfield, and (ii) shows the same microtissue under 488 nm light depicting GFP-expressing hPSC-derived CM.

Figure 22H:
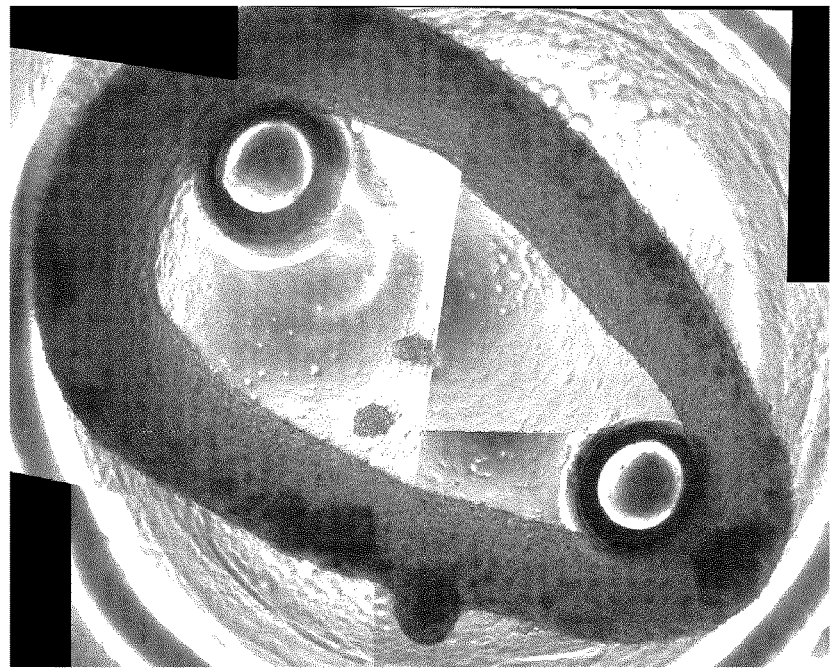

FIG. 22(h) is an image showing microtissue composed of Human umbilical vein endothelial cells (HUVECs) and hPSC-cell derived hepatocytes. Aggregates of hPSC-derived hepatocytes and single cells of HUVECs were mixed together at 100,000 cells per tissue. Tissues remodel within 1-2 days.

Figure 22I:
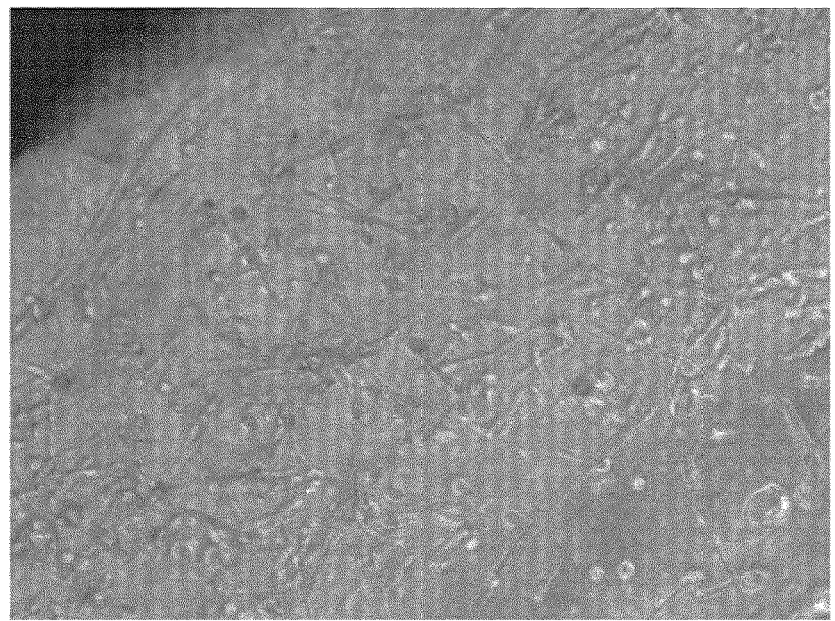

FIG. 22(i) is an image showing microtissue composed of mouse myoblasts differentiated into myotubes. Muscle cells were seeded at 100,000 cells per tissue. Tissues remodel within 3-4 days. Tissues were observed to be contracting spontaneously (after differentiation) within 3-4 days.

Figure 23A:
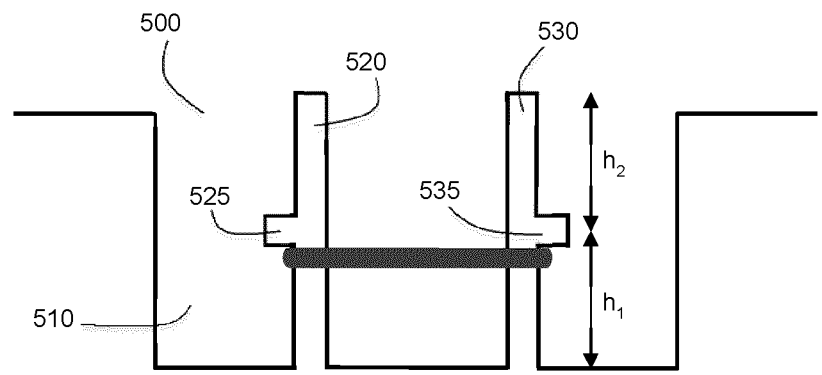
Figure 23B:
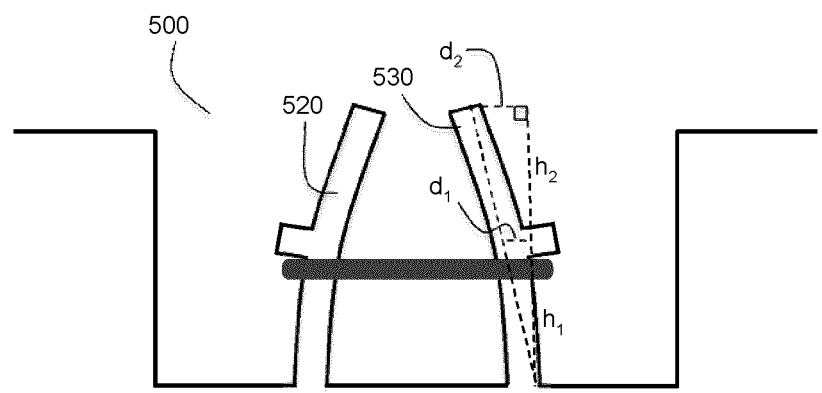

FIG. 23(a) is an illustration of an example cantilever dual-post embodiment where both posts have protuberances. The schematic shows both posts pre-deflection. FIG. 23(b) shows both posts deflected.

Figure 24:
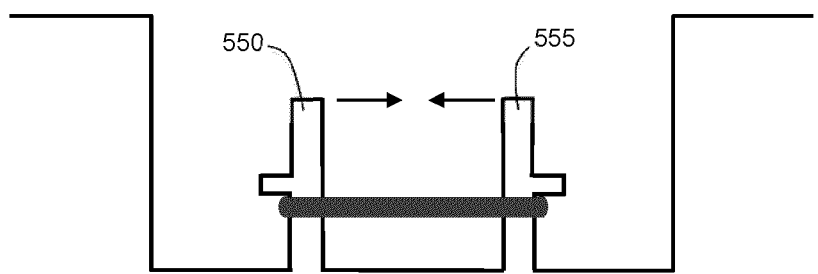

FIG. 24 is an illustration of an example cantilever dual-post embodiment where both posts have protuberances. The schematic shows both posts pre-deflection.

Figure 25:
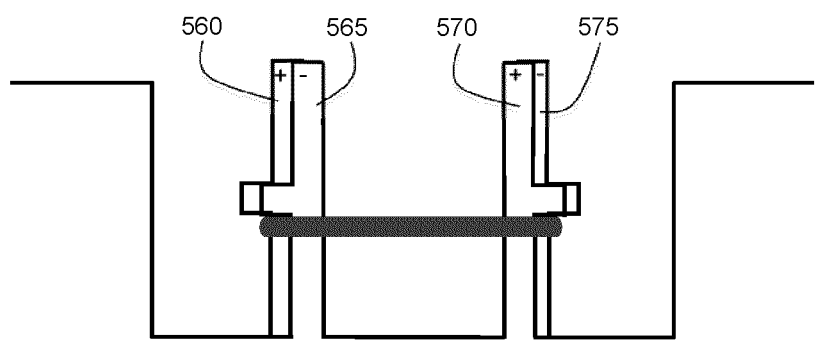

FIG. 25 is an illustration of an example adjacent cantilever dual-post embodiment which act as point stimulation electrodes.

FIGS. 26 (a)-(d) are illustrations of an example cantilever dual-post embodiment where both posts have protuberances; (a) cells are seeded into the well below the level of the protuberance; (b) tissue remodeling occurs and a band of tissue is formed around the protuberances; (c) a second cell type is added to the well; (d) further tissue remodeling occurs in the presence of the second tissue type.

Figure 27A:
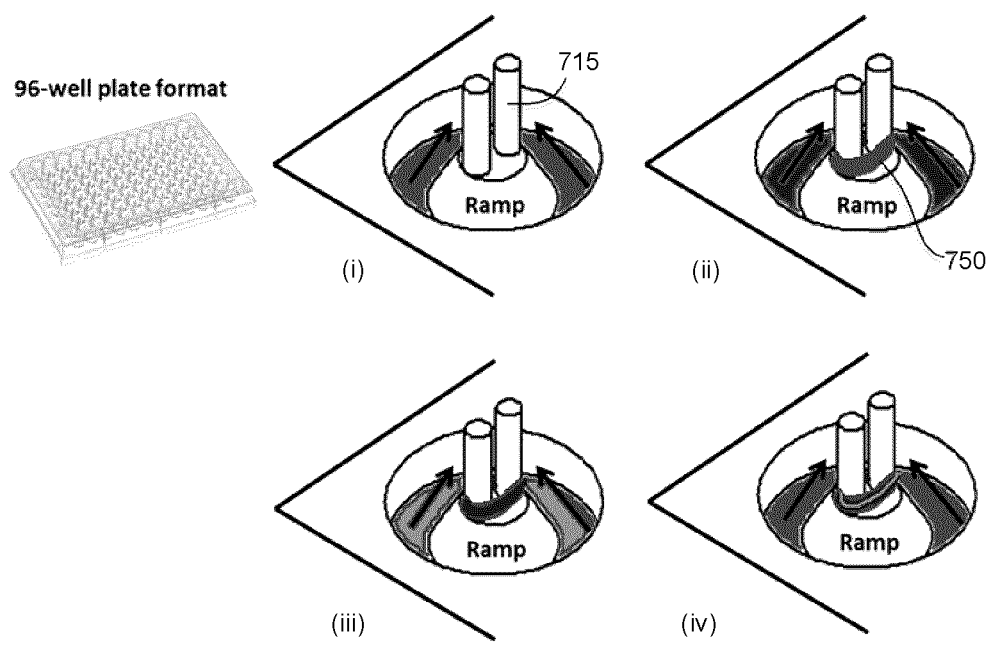

FIG. 27(a) shows an illustration of an example method of forming a composite tissue structure formed using a microfabrication platform having a ramped support within a microwell.

Figure 27B:
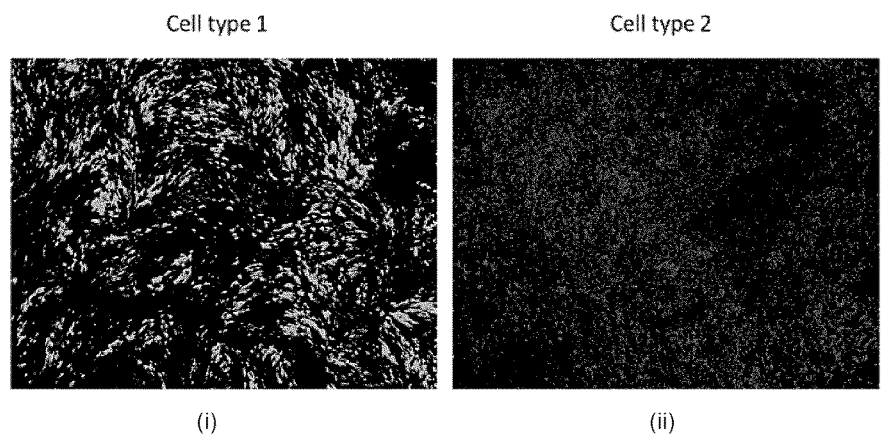

FIG. 27(b) shows fluorescence microscopy images of two cell types (GFP-tagged) and Cell tracker dye Red employed to form a composite tissue construct via a two-stage remodeling process.

Figure 27C:
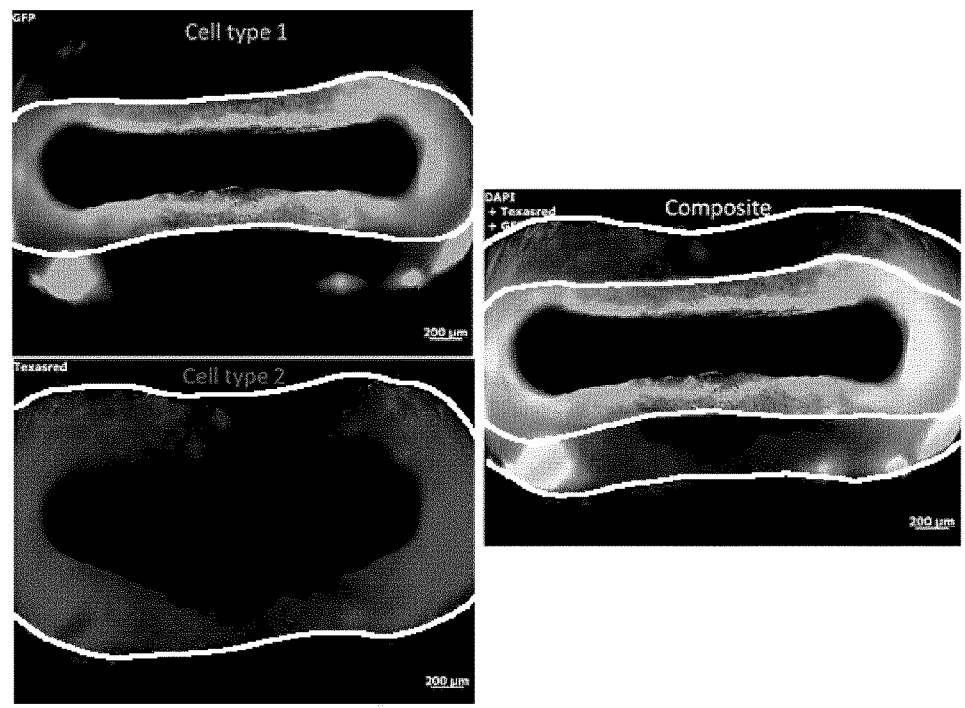

FIGS. 27(c)(i)-(ii) show fluorescence microscopy images of the composite tissue construct at a lower magnification, showing (i) fluorescence from cell type 1, (ii) fluorescence from cell type 2, and (iii) fluorescence from both cell types. In each figure, the regions associated with each cell type are highlighted with in an external white perimeter.

Figure 28:
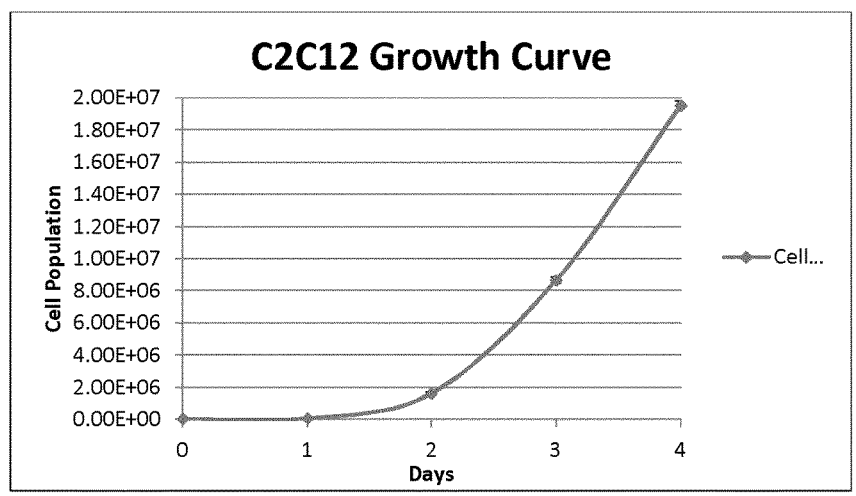

FIG. 28 plots cell population of the C2C12 cell line over four days showing an exponential relationship.

Figures 29, 30, 31:
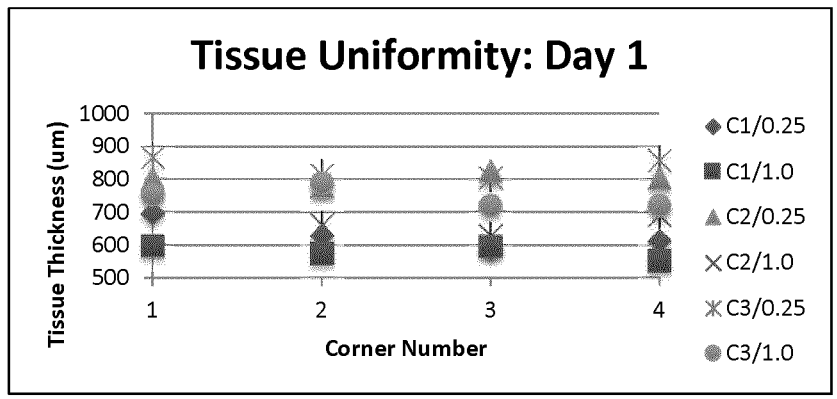

FIG. 29 is a table showing cell/collagen-matrix conditions employed during studies of the characteristics of the tissue constructs.

FIG. 30 is a table present the results of tissue uniformity studies.

FIG. 31 is a plot showing the uniformity of tissue thickness for the four corners of each tissue ring for each of the six conditions for the first day of the experiment.

Figure 32:
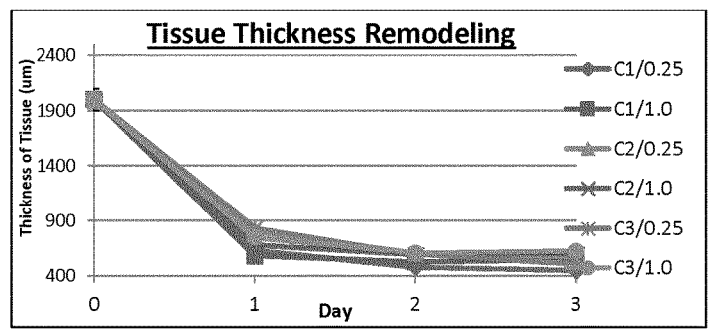

FIG. 32 plots tissue thickness as a function of time over three days for all six conditions.

Figure 33A:
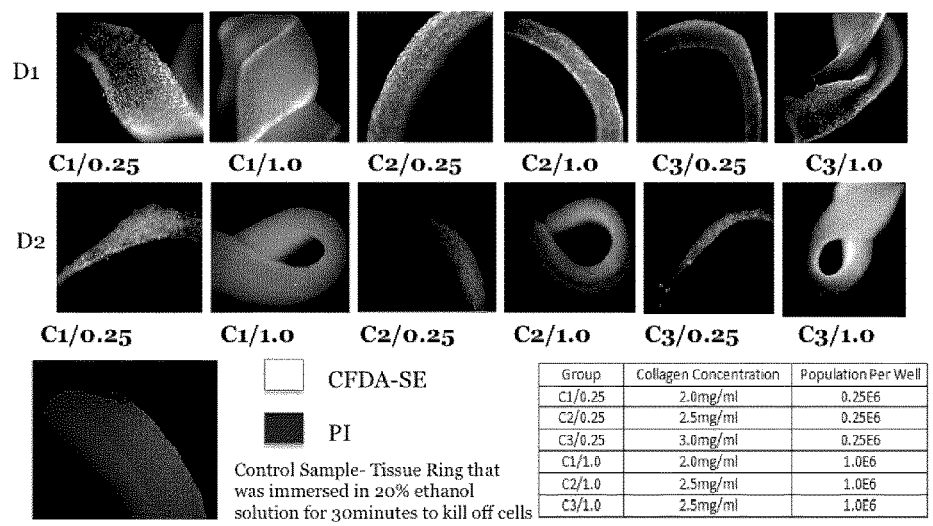

FIGS. 33(a) and (b) present images from (a) live and (b) dead staining of C2C12 tissues from each of the six conditions at day 1 and day 2.

Figures 33B, 34:
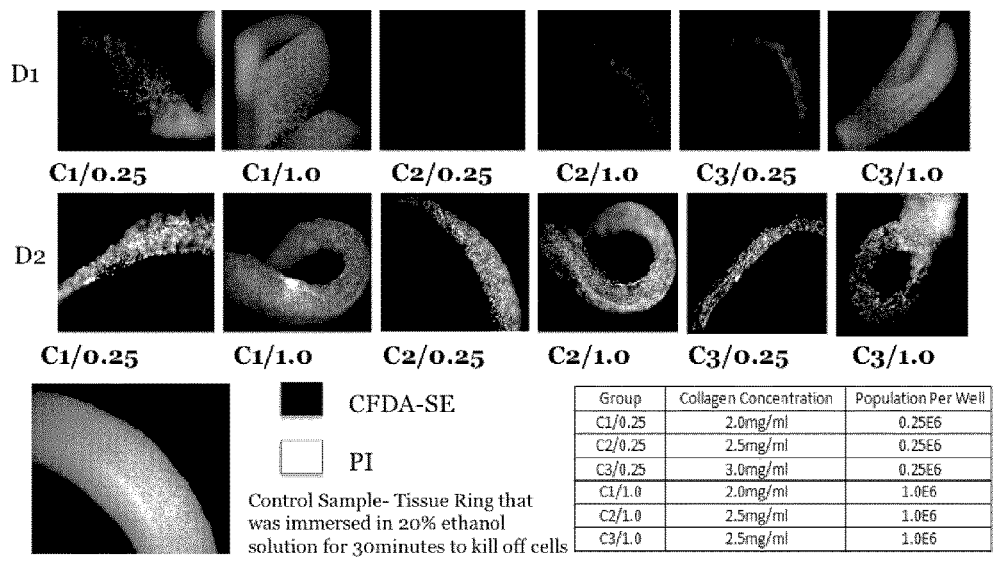

FIG. 34 is a table listing growth factors used at specific concentrations in a preliminary screen.

Figure 35A:
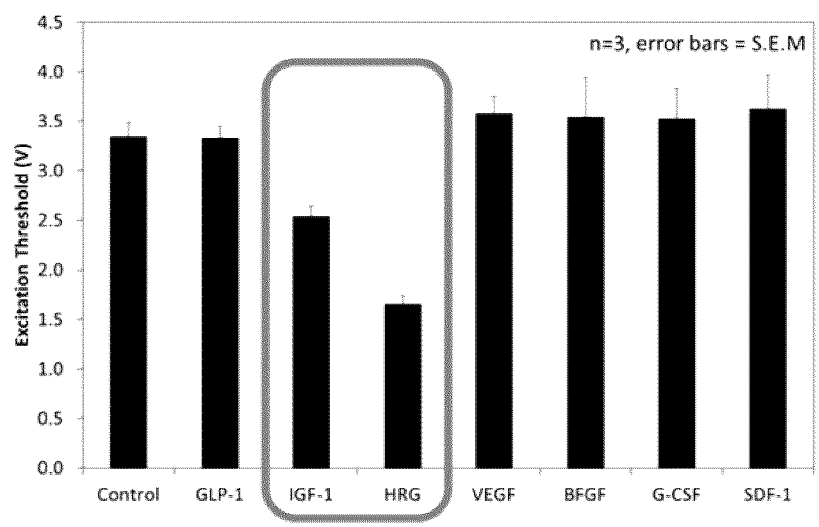

FIGS. 35(a) and (b) plot functional readouts in response to growth factors, where excitation threshold is shown on the left, and maximum capture rate is shown on the right.

Figure 36A:
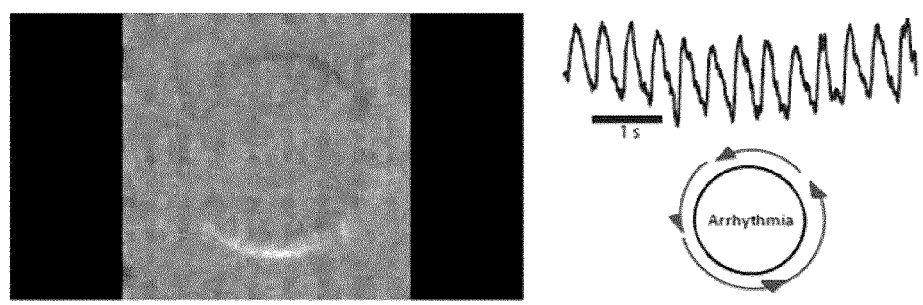
Figure 36B:
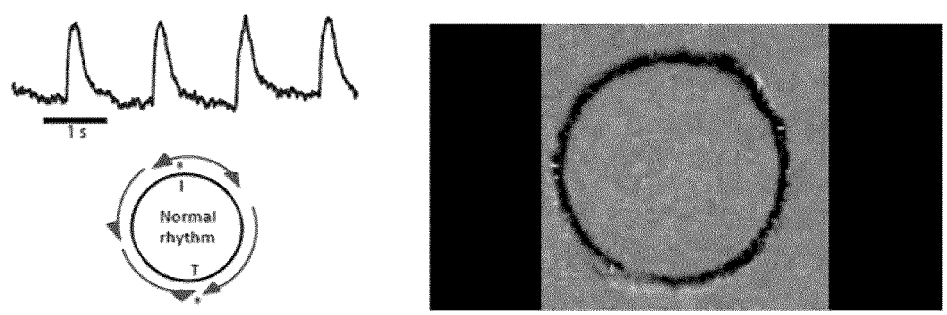

FIGS. 36(a) and (b) show signal tracings of cardiac tissue constructs generated using a circular substrate designed to create a ring of tissue mimicking a re-entrant wave during arrhythmia, where (a) shows an arrhythmia and (b) shows a normal rhythm.

Figure 37:
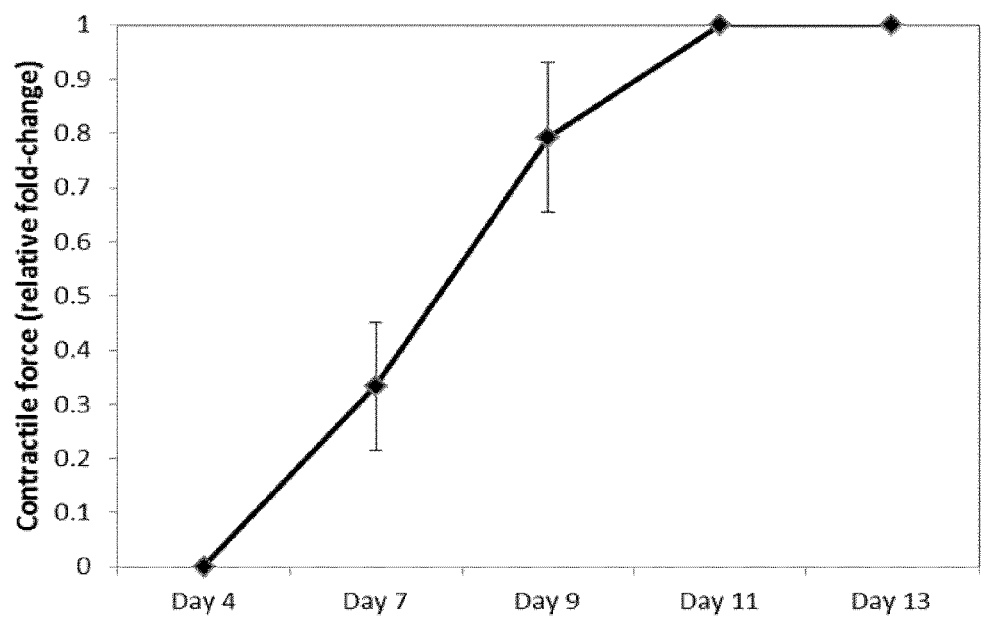

FIG. 37 plots changes in relative contractile force over 2 weeks.

Figure 38:
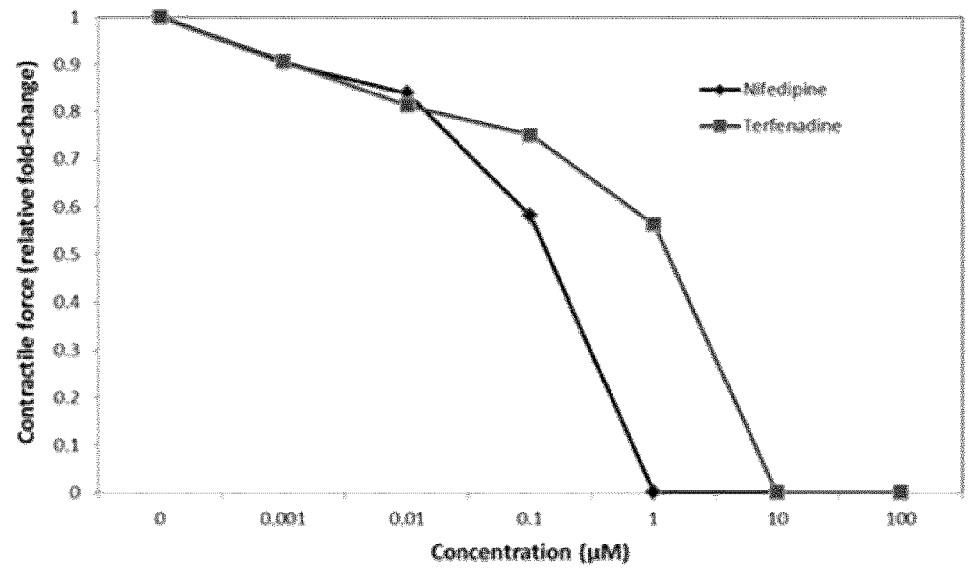

FIG. 38 is a plot demonstrating the effect of selected drugs on the measured contractile force of cardiac tissue constructs.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure. It should be understood that the order of the steps of the methods disclosed herein is immaterial so long as the methods remain operable. Moreover, two or more steps may be conducted simultaneously or in a different order than recited herein unless otherwise specified.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

The formation of cardiac muscle is a complex process that requires a controlled environment to achieve suitable function. In the developing embryo heart, gradients of molecules drive differentiation along the mesoderm and cardiovascular lineages to generate the cell types found in the native heart. Cardiac cells mature by binding to proteins in the highly structured extracellular matrix (ECM), reception of soluble factors, and also in response to electromechanical cues which all together orchestrate self-assembly of excitation-contraction-coupled functional tissue. Later, the adult heart is capable of dynamically maintaining a balanced composition of cardiomyocytes, cardiac fibroblasts, smooth muscle cells and endothelial cells within a highly ordered ECM. It is through complex cell-cell and cell-ECM interactions that the heart maintains homeostasis and, to a limited extent, repairs in response to ischemic injury [10].

In contrast with this native microenvironment, conventional in vitro model platforms for drug screening and toxicity testing use tissue culture-treated polystyrene surfaces coated with a basal membrane. These two-dimensional substrates lack topographical cues and often have an elastic modulus that is orders of magnitude greater than the native substrate of the targeted cell type. Additionally, cardiomyocytes in these assays are cultured either on their own, with conditioned media from stromal cells, or with a physiologically inaccurate proportion of supporting cell types. Supporting cells, such as cardiac fibroblasts, provide paracrine factors that influence cardiomyocyte survival and proliferation and, thus, models lacking this component likely provide inaccurate responses to test compounds.

In addition, gradients of electrical [11] and dynamic mechanical forces [12] provide critical electro- and mechano-transduction signaling throughout development and maturation and following disease, injury and repair. Cell morphology [13], rate of proliferation, migration [14], differentiation potential [15], drug responsiveness [16], and juxtracrine signaling [17] are all influenced by ECM-mediated mechanotransduction. To accurately determine the influence of test compounds, the niche of target cell populations should be strictly recapitulated and controlled. Although some systems have been developed to include mechanical supports and/or sensors for applying a tensile force during the contraction and formation of a cardiac tissue construct, none of the systems reported to date have been successful in producing engineered cardiac tissue that mimics the properties of healthy adult cardiac tissue.

Embodiments disclosed herein provide cardiac constructs that integrate key components of the cardiac niche, and thus represent a physiologically relevant system that may be employed for applications such as high content screening. Selected embodiments of the present disclosure provide artificial cardiac tissue constructs, henceforth termed "cardiac microwire" structures, which include cardiomyocytes, non-myocytes, and extracellular matrix, and may be formed to support the transmission of dynamic electromechanical forces, such that the cardiac microwire may be formed mimicking the basic microenvironment found in the heart. Numerous methods of forming cardiac microwire structures are disclosed below. In some embodiments, an integrated computational and fabrication method is provided for the design and formation of a cardiac microwire, for example, with a suitable or pre-selected geometry and/or sarcomeric expression spatial profile. In some embodiments, one or more cardiac microwires may be microfabricated for high-content screening, for example, within microwells of a microplate.

In some example embodiments, methods are provided for forming cardiac microwires in a morphologically reproducible form, such that high cardiac sarcomeric protein expression is maintained in a dense, aligned, and suspended 3-D extracellular matrix, which may be adapted to exhibit normal electrophysiological responsiveness. Cardiac microwires may be formed by integrating and further maturing dense and aligned cardiomyocytes, and non-myocytes, in a freely suspended collagen-based matrix, under electromechanical forces, thus assembling important aspects of the cardiac niche for measuring physiologically accurate responses in high content screens.

For example, as described in detail below, a cardiac microwire composed of human Pluripotent Stem Cell-derived cardiomyocytes, formed under a rapid (7-day) maturation regimen, yielded a cardiac microwire, in the absence of a scaffold, with a conduction velocity of 47.4±12.4 cm/s, on par with healthy human heart tissue. Additionally, as described below, gene expression studies of cardiac microwire (composed of 75% NKX2-5-GFP+ and 25% CD90+ cells) revealed significant increases in key cardiac markers of maturation including MYL2, MYL7, and MYH7. These results demonstrate the suitability of the cardiac microwire platform a tool for the maturation of hPSC-derived cardiomyocytes and screening of small molecules toward heart regeneration therapies.

Engineered myocardial tissues can be used to both elucidate fundamental features of myocardial biology and develop organotypic in vitro model systems. The cardiac microwires disclosed herein may, in selected embodiments, provide significant advantages over current approaches. Some potential benefits of the embodiments provided herein may include 1) recapitulation of the myocardial niche; 2) the ability to report multiple functional parameters; 3) miniaturization; 4) capacity for bulk manufacturing; and 5) maturation of the cardiomyocyte component. As shown in the examples below, example implementations of the embodiments taught herein have been shown to fulfill these criteria, and have been experimentally validated through phenotypic and functional characterization. For example, the role of ECM topography was first confirmed as being important for promoting aligned cell morphology and function.

Furthermore, in order to identify appropriate microtissue geometries, a computational simulation of microtissue contractility may be employed to predict and evaluate areas of high stress and cardiac protein expression. By linking areas of high stress with high cardiac protein expression and cell alignment, predictions of increased cardiac protein expression were experimentally confirmed in areas of increased uniaxial stress and chose a microtissue configuration consisting primarily of uniaxial intra-tissue tension forces.

Miniaturization of the cardiac microwire platform eliminates the need for vascularization, as microtissue has a cross-section characterized by a radius that is below the diffusion limitation threshold of 150 μm. The lack of a diffusion barrier also allows for the exploitation of traditional immunofluorescence and imaging techniques in situ. Additionally, the input cell population needed for assaying is minimal compared to conventional three-dimensional in vitro models.

The ability to integrate electromechanical stimuli in the system may be provided via pacing with point stimulation electrodes and passive mechanical stretching. This form factor provides, unlike others, the ability to engineer various structures of cardiac tissue, control the mixing of the input population of cells to induce self-organization, and measure conduction velocity and gene expression via qPCR of single microtissues. The examples below also demonstrate the effect of input cell population ratios on tissue morphology and gene expression in the context of cardiac maturation, which is an important area of focus for the development of adult-like in vitro models.

The forthcoming sections of the disclosure illustrate some example implementations of cardiac microwire tissue structures and methods of their fabrication. These example implementations are also described in further detail below, in the Examples section.

Cardiac Microwire Formation Using Microtissue Platforms

In one embodiment, in order to engineer an accurate heart cell niche, a 3-D cell-encapsulating ECM geometry is provided. To achieve this, the cells' ability to remodel pliant ECM during phases of growth and proliferation is exploited. Through gel compaction due to cell traction forces, dissociated heart cells encapsulated in a gel undergo changes through several phases, including:

1) recovery of actin filaments and extension of filopodia;
2) accumulation and assembly of cell adhesion molecules, gap junctional and contractile proteins; and
3) excitation-contraction coupling which permits the cardiac tissue to propagate action potentials and contract in unison [18].

In some embodiments, a three-dimensional tissue construct may be formed according to the preceding steps using a microfabrication platform that includes two or more retaining structures for retaining the tissue construct during the remodeling process and for applying a suitable distribution of tension within the construct for achieving formation and alignment of sarcomeres. Such a microfabrication platform generally includes a microwell (e.g. having dimensions on the millimeter or sub-millimeter scale) for receiving cells and a collagen mastermix and at least two retaining structures within the well for constraining the tissue construct into a pre-selected geometry during the remodeling process. In some embodiments, the retaining structures may extend vertically from the base of the microwell.

In some embodiments below, the retaining structures are referred to as "nodes" and/or "posts". For example, one or more of the retaining structures may be a substantially cylindrical post, although it is to be understood that the retaining structures may take on other geometrical shapes, so long as they are suitable for retaining the tissue construct during its contraction, and such that the retaining structures are provided such that tension is applied within the tissue construct during the remodeling process. In some embodiments, the structural features may be provided such that the tension forces generated within the tissue construct, during and after remodeling, are substantially uniaxial. In other embodiments, as discussed in further detail below, the retaining structures may have elastic properties such that an auxotonic load is applied to the tissue construct during its formation through remodeling. In other embodiments, electrodes may be integrated within the microtissue platform for providing point stimulation, as further described below.

In some embodiments, the retaining structures may provide the dual role of physically constraining the tissue construct during remodeling, and acting as a force transducer due to a tension-dependent displacement of the structural features. In such embodiments, the retaining structures may be referred to as microcantilevers. It is to be understood that numerous variations of these aforementioned embodiments are envisioned according to the present disclosure. For example, the number of cantilevers within the microwells can be varied depending on the "biaxiality" required of the tissue construct. In some embodiments, it may be desirable to produce a tissue construct with uniaxial forces, in order to allow for cell and tissue alignment (e.g. cardiac, skeletal muscle, vasculature). In other embodiments, some tissue constructs may not require alignment (e.g. the liver or gut).

In some embodiments, the microtissues are maintained within the microwells in a manner that prevents tissue adherence to the posts. The surface of the microwells and the retaining structures may be treated with a coating that prevents adhesion of cells/ECM/proteins. Suitable coating materials include Pluronic™ acid (or another suitable poloxamer) and BSA, which may be provided with a sufficient concentration and/or quantity such that it is non-adherent to the microtissue during remodeling of the construct. In one example implementation, the coating material may be approximately 5% Pluronic™ acid. In some cases, however, it may be desirable to provide varying degrees of adhesion among different constructs. In cases where there are extensive amounts of remodeling, lower concentrations of Pluronic™ can be used (such as approximately 0.5-2%), while in cases of very little remodeling, higher percentages (such as approximately 4-6%) can be used. For example, in cultures of pure fibroblasts, approximately 0.5-2% Pluronic™ can be used, and for cardiomyocyte tissues, approximately 4-6% Pluronic™ can be used (as long as the retaining features are effective in both cases).

The continuous contractions of cardiomyocytes within the tissues may also prevent the cells from developing adhesion onto any exposed surface. As a result, the tissue tends to slip and slide along the round edges of the rigid posts. This flexibility of the tissue allows for more stretching without risk of tearing or total tissue snapping.

For example, in the case of the uniaxial or biaxial tissue construct formation, a suitable concentration of Pluronic™ Acid F-127 is approximately 2-8% in order to obtain sliding and separation of the tissue from the retaining structures, depending on the tissue composition (more contractility, which may occur, for example, due to more fibroblasts, would require lower concentrations). At lower concentrations, the microtissue may become bonded to the retaining structures, although in some tissue engineering applications, this may be desirable.

It is to be understood that many different adherent cell types may be combined with suitable ECM compositions to generate tissue types of interest. For examples, tissues that can be generated include (but are not limited to) cardiac microtissue, skeletal muscle tissue, vascular tissue, liver tissue, gut tissue, neuronal tissue, adipose tissue, and cartilage tissue.

Figure 1A:
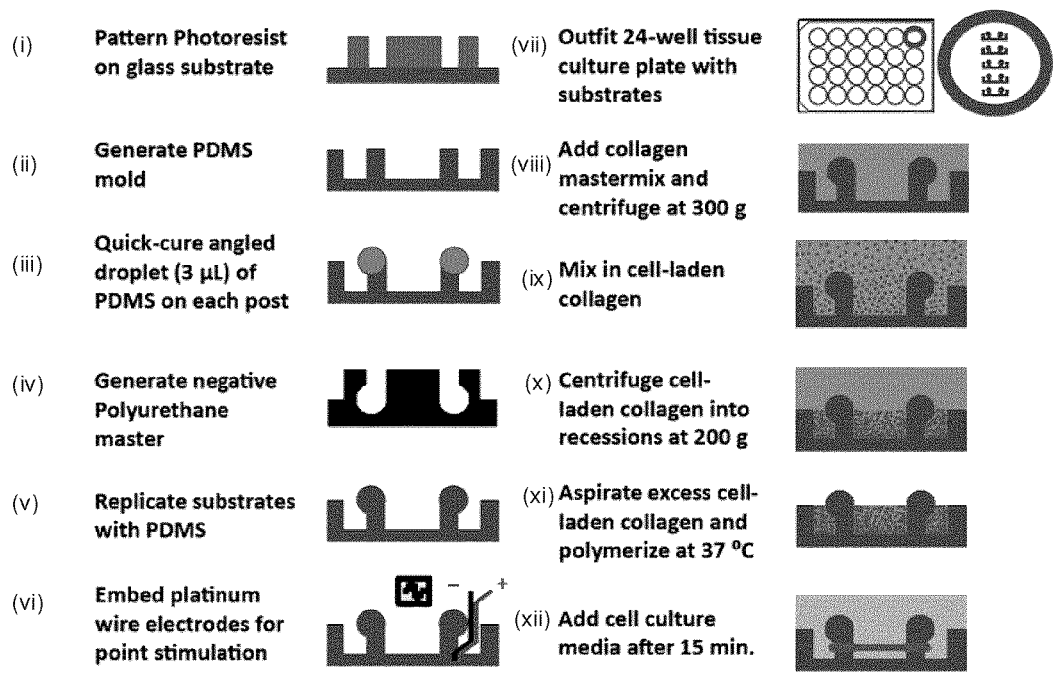
FIG. 1(a) illustrates the steps in which a PDMS substrate is replicated from a microfabricated master, and then modified with tapered heads. A negative polyurethane-based master is generated and used as the final master. Substrates are then prepared in 24-well plates and sterilized. Cell laden collagen is centrifuged into recessions of microwells and allowed to remodel into densely packed tissue.

In some embodiments, a microfabrication technique may be employed to create an array of isolated microwells of various sizes, containing specific node geometries, to restrain the remodeling of localized pockets of cell laden collagen within the microwell recessions, as shown in FIG. 1(a).

According to one example implementation, a microfabrication platform may be provided as follows. Photoresist is first patterned onto a glass substrate as in FIG. 1(a) (i). Briefly, piranha-washed 3×5" clean glass slides (Corning Inc., Corning, N.Y., USA) are given a brief wash in acetone and blow dried under a clean stream of nitrogen gas. A seed layer of SU-8-5 (Microchem, Newton, Mass., USA) (7 um high) is spin-coated on the surface to allow for feature layer bonding. Following a dehydration bake at 20 min on a 100 degrees Celsius hot plate, the slides are cooled to 65 degrees Celsius and then removed from the hot plate to return to room temperature. The seed layer is exposed with UV and post-bake was initiated as before. Slides with seed layers are then obtained and 2 spin coat layers SU-8-50 (Microchem) are applied sequentially (including pre- and post-bakes) to reach a feature layer height of 300 um. A UV exposure step with a designed mask onto a master with 300 um high feature layer is then performed. Post-baking was performed to allow sufficient time to cool. Additional layers can be added (including protuberances and grooves by modifying the mask design and applying sequential layers of SU-8) building the structure from the bottom up.

The slides are then immersed in Developer (Microchem) on a sonicator or orbital shaker for a sufficient amount of time to wash away uncross-linked SU-8. Masters are oven-baked for 3 days at 75 degrees Celsius to allow proper bonding of feature layer to glass slide. Masters are then silanized in a desiccator overnight.

Primary replicates are manufactured by molding poly (dimethylsiloxane) (PDMS, Dow Corning) on SU-8 masters at 65 degrees Celsius overnight, as shown in FIG. 1a (ii). Replicated molds are modified under a stereomicroscope by quick-curing angled droplets of PDMS on each post, as shown in FIG. 1a (iii), and a negative master is molded using polyurethane (SmoothCast), as shown in FIG. 1a (iv). Final substrates are then PDMS molded from these negative masters and outfitted into a 24-well tissue culture plate, as shown in FIG. 1a (v-vii).

These substrates are sterilized using ethanol and then coated with Pluronic™ Acid for 24 hours. The 24-well containing substrates are then washed. Collagen is then added to the substrates, which are then centrifuged at 300 g, as shown in FIG. 1a (viii). Cell-laden collagen mastermix (cell mix containing cardiomyocytes and fibroblasts suspended in collagen mastermix) is then mixed in, such that the formation of bubbles is avoided, as shown in FIG. 1a (ix). The entire plate is then centrifuged at 200 g to force the cell-laden collagen in into recessed wells, as shown in FIG. 1a (x). Excess cell-laden collagen is aspirated from the substrates and the entire plate was placed inside an incubator at 37 degrees Celsius for 15 minutes to allow the collagen to polymerize, as shown in FIG. 1a (xi). Finally, after the 15 minutes of polymerization, cell culture media is slowly added to the corner of each well (such that the collagen was not disturbed) and the cell laden collagen is allowed to remodel, as shown in FIG. 1a (xii). It is to be understood that the preceding method is but one example implementation for producing a microfabrication platform. Furthermore other materials may be employed when forming the tissue construct. For example, other polymerizable hydrogels may alternatively be employed with the system including, but not limited to, fibrin, PEG-based hydrogels, and Matrigel™. In alternative examples, a combination of basement membranes/ECM components can also be combined to mimic that of the native tissue ECM, for example, including laminin, vitronectin, and fibronectin.

In other embodiments, the concentration of the hydrogel, which is correlated to the substrate stiffness, may also be varied. For example, the hydrogel concentration may be selected from the range that falls within the elastic modulus found in native muscle tissue. In the example case of cardiac microtissues, this elastic modulus is on the order of 10 kPa (ranging from 1 kPa up to 20 kPa). The cell density also is a factor which can be varied in order to obtain a tissue construct with suitable properties, although the properties of the tissue construct depend on the ability of the cells to contract and to supply appropriate paracrine signaling.

For example, in some embodiments, the cell concentration may be between approximately 25,000-100,000 cells per tissue for an example microfabrication platform geometry which holds a volume of approximately 5 uL (cell density of $5*10^6$ cells/mL-$20*10^6$ cells/mL). It is to be understood that the amount of cells plated will be dependent on the tissue type. In some instances, approximately 25,000 cells provide the optimal number of cells and required cell spacing to maintain function. If too few cells are plated, there will not be sufficient numbers to achieve collagen remodeling. Conversely, if there are too many cells, cells will be too closely packed, compromising cell function and viability.

The relative proportions of cell types employed to form the tissue construct may also be selected in order to control or vary properties of the tissue construct. For example, variations in the relative proportions of the cell types may result in a large difference in the outcome of the tissue construct, both structurally and functionally. As disclosed herein, in some embodiments, it is important to control the relative proportion of fibroblasts and cardiomyocytes in order to generate structurally and functionally sound tissue.

In one non-limiting example, it has been found that a composition of approximately 25% CD90+ cells (fibroblasts) and approximately 75% NKX-2-5-GFP+ cells (cardiomyocytes) was found to be suitable for producing cardiac tissue constructs with properties approximately mimicking a human health heart. Indeed, in the native heart, fibroblasts work to provide structural integrity and paracrine signaling, two factors that are important in recapitulating tissue in the present cardiac microwire platform.

The embodiments and examples disclosed herein highlight the importance of tissue composition in by showing improved functional assembly and superior mature gene expression in the 75% NKX2-5 and 25% CD90+ cardiac microwire. As described below, increased gene expression levels of key cardiac maturation markers is observed, including genes implicated in sarcomere structure, as well as ANF and BNP which increase during the fetal heart gene programme when organogenesis commences. Without intending to be limited by theory, it is believed that there may exist a certain degree of paracrine signaling provided by the CD90+ cells that promotes maturation. Putatively fibroblasts, these CD90+ cells may secrete growth factors such as bFGF and VEGF. Additionally, the CD90+ cells contribute to the majority of the ECM remodeling, and as a direct result, promote cell-cell contact which may facilitate maturation-promoting signaling. Additionally, the remodeling may provide mechanotransductive cues including higher tension and in turn, CM elongation and alignment.

It is to be understood that the compositional ranges of the cardiac microwires are not limited to those provided above. For example, while a composition involving a cellular content of approximately 75% CM and 25% non-CM has been found to be suitable for achieving cardiac constructs with properties (such as conduction velocity) characteristic of a healthy human heart, other compositions are possible. In some embodiments, a cardiac microtissue construct has a composition including at least a small percentage of non-myocytes (such as primarily CD90+ FB), in order to allow for structural integrity, and maturation of structure and function. For example, in some embodiments, the cardiac tissue construct may have a relative cellular content of approximately 70-80% CMs and approximately 20-30% non-myocytes (such as CD90+ FB). In other embodiments, the cardiac tissue construct may have a relative cellular content of approximately 65-85% CMs and approximately 15-35% non-myocytes. In other embodiments, the cardiac tissue construct may have a relative cellular content of approximately 60-90% CMs and approximately 10-40% non-myocytes. In other embodiments, the cardiac tissue construct may have a relative cellular content of approximately 55-95% CMs and approximately 5-45% non-myocytes.

Alternatives for the microtissue platform include, but are not limited to, polystyrene, agarose, and polyethylene glycol (PEG) (in place of PDMS). Other moldable materials suitable for cell culture may be substituted for PDMS. Also useful are 3-D printer materials that can be used to directly print the substrates without the need for molding. Additionally, more than one type of material can be printed at once, including conductive, elastic, and transparent materials.

In many embodiments, a general layout for the microtissue platform consists of arrayed wells containing dual posts. Variations of these arrangements can be made, however, that will result in tissue microwire formation. Specifically, the arrangement of the posts can be altered to generate desired tissue geometries. FIG. 11(a) illustrates various example geometries and dimensions for forming biaxial (i) and uniaxial (ii) and (iii) tissue configurations.

In the examples below, an additional criterion that was applied was that the microtissues needed to be large enough to be harvested for qPCR analyses and in situ electrophysiological analyses (including directional impulse propagation, electrical point stimulation, and conduction velocity). However, this is to be understood to be a non-limiting criterion that would not be relevant in other applications, depending on the nature of any testing, analysis, or other post-processing to be performed on the tissue construct.

Auxotonic Load

Auxotonic load can be simulated in vitro by providing non-static elastic resistance to microtissues during the contraction phase to simulate the elastic border regions which are composed of elastic ECM which stretches along with the contracting CM. The effect of auxotonic load results in the structural and functional improvement of the microtissue. In embodiments described herein, tissues can be engineered to experience ranges of auxotonic load (depending on the resistance provided by the anchoring posts).

Auxotonic load can be simulated (at various degrees) by changing the resistance provided by the cantilevers (posts). This can be done, for example, by changing the diameters of the cantilevers along their axial extent. As the tissue contracts, the resistance provided by the cantilevers will non-linearly increase (due to the elastic properties of the cantilever material, such as PMDS). In one embodiment, the cantilevers are formed such that their elastic resistance is matched or approximately equal to the elastic properties of a selected tissue, such as heart ECM. This can be achieved to various degrees, in order to mimic healthy (mature and immature) and diseased tissue. PDMS is a suitable material to use for this case. In one embodiment, the diameter of the cantilever can range from approximately 50 µm to 300 µm, as mentioned previously.

Microtissue Platform with Stabilizing Features

It can be important or useful, in some cases, to stabilize or localize the tissue construct during (and after) the contraction/remodeling process. Accordingly, in some embodiments, at least one of the retaining structures includes a stabilizing feature for stabilizing the position of the tissue construct during its formation. Such stabilizing features may be employed, for example, for applications where it is important or useful to form the tissue construct at a pre-selected location relative to the base of the microwell, in a reproducible manner.

For example, when measuring the force of contraction in a set of tissue constructs (e.g. mounted within a multi-microwell carrier such as a microplate) using microcantilevers, it may be important to localize or stabilize the location of each tissue construct on a given microcantilever relative the each associated microwell base in order to provide a measure of the force exerted due to contraction that is consistent for all tissue constructs.

In another example, the stabilization of the location of the tissue construct at a pre-selected location may be useful in applications in which optical imaging is employed for the assessment of a tissue construct during and/or after its formation. Specifically, it may be beneficial to stabilize the formation of the tissue construct within or near (i.e. proximal to) a focal plane of an optical imaging system. Such an embodiment may be useful in applications involving multiple microwells that are serially optically imaged by relative translation of the microwells and an optical system (such as in a microplate reader).

In some embodiments, the stabilizing feature may be formed as a cap or other structure located at a distal end of a given retaining structure. In other embodiments, the stabilizing feature may be provided at an intermediate location between the base of the microwell and the distal end of the retaining structure.

FIG. 16(a) generally shows a microwell 200 having two posts 210. FIGS. 16(b)-(e) illustrate several non-limiting examples of retaining structures having a stabilizing feature located at an intermediate location between the base of the microwell and the distal end of the retaining structure.

In FIG. 16(b), retaining structure 220 is shown including local protuberance 225 that is provided at a location between base 230 of the microwell and the distal end 235 of retaining structure 220. During its formation, the tissue construct is prevented from moving vertically beyond the location of protuberance 225.

FIG. 16(c) illustrates another embodiment in which retaining structure 240 includes groove (or notch) 245, such that during the contraction process, the vertical position of the tissue construct is fixed by groove 245. Although protuberance 225 of FIG. 16(b) and groove 245 of FIG. 16(c) are shown as having straight side edges, it is to be understood that any one or more edges or other surfaces of protuberance 225 and/or groove 245 may have curved surfaces.

FIGS. 16(d) and (e) illustrate two example embodiments of intermediate stabilizing features in which a ramped or tapered profile is employed to induce the tissue construct to equilibrate at a given position during its formation. For example, in FIG. 16(d), retaining structure 250 is provided such that the presence of ramp 255 and the tension in the tissue construct causes a vertical force to be applied to the construct when it contacts ramp 255, thereby inducing upward motion of the tissue construct until it contacts, and is stabilized in position, by protuberance 260.

Similarly, in FIG. 16(e), retaining structure 270 is shown where the intermediate stabilizing feature includes a double ramp structure, having lower ramp segment 275, upper ramp segment 280 (extending outwards and in an upwards direction), and a minimum position 285. During formation and contraction, the tissue construct moves upwards on lower ramp segment 275 until it reaches minimum position 285, and where motion beyond minimum position 285 is prevented by upper ramp segment 280. It is to be understood that the geometry and/or curvature of the ramped features need not be exactly as shown in FIGS. 16(d) and (e). For example, the ramped feature need not terminate in a vertex, but may instead terminate in a smooth curve. For example, in FIG. 16(e), minimum position 285 may take the form of a U-shaped feature, instead of a V-shaped feature (i.e. a vertex). Furthermore, upper ramp segment 280 and lower ramp segment 275 need not be symmetric. For example, it may be beneficial for upper ramp segment 280 to have a higher curvature or slope relative to lower ramp segment 275, in order to further assist in stabilizing the position of the tissue construct at minimum position 285.

In another embodiment shown in FIG. 16(f), retaining structure 300 may be provided with ramp segment 305 that extends towards a distal portion 310 of the retaining structure, and where distal portion 310 includes a stabilizing feature such as a cap 315 or globule. Ramp segment 305 assists in biasing the position of the tissue construct towards the distal portion 310 of the retaining structure 300, such that the tissue construct is then stabilized in position by cap 315.

FIG. 16(g) shows retaining structure 320 having a protuberance 325 as well as a post-deflection amplification extension 330, for amplifying the deflection of the retaining structure.

The tissue microwire dimensions will depend upon the starting conditions. Higher ECM concentrations and higher cells densities will generally result in larger diameter microtissues, whereas lower ECM concentrations and lower cell densities will result in smaller diameter tissues. On average, microtissues have been found to remodel to a diameter of 80-250 µm. The length may vary based upon the spacing of the posts. In one example dual post design, the length may vary between approximately 0.5 and 5 mm.

FIGS. 17(a)-(f) show example embodiments of microtissue formation using various post geometries in which posts are positioned to apply tension to a tissue construct during its formation. (a) shows variations of the base dual post design; where the distance between posts is, for example: (i) approximately 0.5-2.5 mm, (ii) approximately 2.5-5 mm, (iii) approximately 5-10 mm, (iv) approximately 2.5-5 mm, and (v) approximately 2.5-5 mm. FIG. 17(b) shows a grid pattern for connecting the designs together; where the distance between posts is approximately 2.5-5 mm. FIG. 17(c) shows a radial pattern layout; where the distance between posts is approximately 2.5-5 mm. FIG. 17(d) shows a circumferential pattern layout, where the distance between posts is approximately 2.5-5 mm.

FIG. 17(e) shows the same basic dual post (retaining structure) layout, but, with tissues that form rings rather than strips. This may be accomplished, for example, by providing a ramp that may extend from the sides of the retaining structures, or provided below the retaining structures (as described further below). In another embodiment, a blocking or connecting structure may be provided between the posts, along at least a portion of the length of the retaining structures, to prevent tissue formation therebetween. In some embodiments, a blocking structure may be provided in the lower portion of the retaining structures, in order to avoid the interconnection of tissue between the retaining structures during the initial remodeling phase. Example blocking structures include a connecting feature extending between the retaining structures, such as a longitudinal or elliptical structure. The distance between posts may be, for example: (i) approximately 0.5-2.5 mm, (ii) approximately 2.5-5 mm, (iii) approximately 5-10 mm, and (iv) approximately 2.5-5 mm.

FIG. 17(f) shows a large circumferential tissue design. One large post of approximately 1-4 mm in diameter for tissue to remodel around is shown.

It is to be understood that the dimensions of shown and described above can be further scaled up or down and that the ranges provided are merely examples. Additionally, posts can be replaced with electrodes or conductive materials to allow electrical stimulation/recording. In some embodiments, the well depths may range from approximately 200 µm to 1 mm.

In some embodiments, cantilever post diameters range from 50 µm to 300 µm, depending on the extent of deflection desired. The embodiments shown can be arrayed in a multiwell plate (e.g. 6-well, 12-well, 24-well, 48-well, 96-well, etc.) for tissue culture. Additionally, posts can be replaced with electrodes or conductive materials to allow electrical stimulation/recording.

FIGS. 18 (a)-(d) show post deflection as captured in still images from a video file, where (a) shows a field view of cardiac tissue attached to posts pre-deflection, and (b) shows the same field view as in (a) post-deflection. FIGS. 18(c) and (d) show close-ups of the posts in (a) and (b), respectively. The arrow is in the same position in the field image in both (c) and (d).

FIG. 19 shows an example embodiment of a cantilever dual post design where posts 410 and 420 each have protuberances 415 and 425, respectively, for retaining microtissue construct 400. First post 410 has integrated electrodes 430, and is rigidly maintained while the second post 420 is capable of flexing.

It is also to be understood that the different retaining structures within a given microfabrication platform need not have identical stabilizing features. For example, as shown in FIG. 20, two retaining structures of a given microfabrication platform may have different configurations of their stabilizing features (such as one retaining structure having a groove 440, and another having a protuberance 445).

In another embodiment, a microfabrication platform may be provided in which one or more retaining structures includes a stabilizing feature, and one or more other retaining structures does not include a stabilizing feature. Such an embodiment may be useful in providing a microtissue platform having retaining structures that are customized for different purposes. For example, one or more retaining structures may be provided with stabilizing features for stabilizing the height of the tissue construct relative to the base of the microwell. Such a retaining structure may exhibit a lower deflection under applied tension, due to the presence of the stabilizing feature (e.g. the increased diameter of the retaining structure due to the presence of a ramped feature or protuberance). One or more other retaining structures may be provided without stabilizing features, such that a larger deflection is obtained under applied tension. Accordingly, one or more retaining structures may be configured for stabilizing the height of the tissue construct relative to the microwell base, and one or more other retaining structures may be configured for producing a measurable deflection due to the tension applied by the tissue construct during its formation.

Additionally, this concept can be used to create microtissues that experience a range of intratissue stresses due to the modulation of resistance provided by the posts. Additionally, 3D geometries that begin to vary microtissue positioning on the 'z' axis (vertically) can be engineered. This may be perhaps useful when trying to manipulate the distance a component of a tissue is from a soluble factor signaling source (for example a secondary cell type in a co-culture setup or diffusive factor sourced on the microwell floor). This type of design may help in recapitulating some of the gradient-based growth factor signaling occurring during early tissue morphogenesis in the embryo.

FIG. 21 shows a cantilever multiple post design combining protuberance-containing (450, 455, 460) and groove-containing (465) features. The combination of retaining features is used to control tissue formation.

Microtissue Platforms with Ramped Structures

According to some embodiments, the microfabrication platform may include one or more structural features that are configured to raise the tissue construct from the well base during the remolding process, and/or to induce the formation of the tissue construct in a ring geometry/topology.

Raising the tissue construct from the floor or base of the microwell may provide many benefits. For example, as described further below, the microfabrication platform may include a structural feature, such as a ramp or incline, that prevents the tissue construct from contacting the posts early during the remodeling process, such that contact with the posts is achieved after the remodeling process has already been initiated. This facilitates the formation of a tissue construct having a ring structure without the tissue connection taking place between the posts.

Another potential advantage of a ramped structure is that dead cells and debris, which have settled onto the well bottom, are separated from the tissue construct during the remodeling process, and therefore the dead cells and debris can be easily washed away during media changes. Additionally, there is increased access to media on all sides of the tissue when it is drawn away from the floor of the well under tensile forces during the remodeling process. Further to this point, when staining the tissues (e.g. after fixing/permeablizing) in situ with antibodies, tissues are more accessible when suspended above the floor of the well to allow antibodies to permeate into tissue. Furthermore, sensors/stimulants can be installed or fabricated on the base of the well (including electrodes).

Another benefit of a ramped configuration is that problems associated with prolonged contact of cells to a surface may be avoided. Such contact can eventually permit cells adhesion due to protein adhesion (despite coating the surfaces with a coating). As such, raising the tissue up and away from the floor will prevent this from happening. Furthermore, locating the tissues at an intermediate location, as described above, rather than the top of the posts, will still allow for imaging of the tissue from the bottom (rather than the top). If the tissue construct is permitted to rise too high up the posts, the working distance of the microscope may not allow for focusing of the tissue.

Accordingly, in one example implementation, a microfabrication platform may be provided with two retaining structures, where one retaining structure includes a groove, protuberance, and the other retaining structure includes a ramped feature. The ramped feature may extend in an upward direction such that it ends at a height that is approximately equal to the height of the protuberance of the other retaining structure, as shown in FIG. 22(*a*). Alternatively, the ramped feature may end below this height. The retaining structure having the ramped feature may also include a stabilizing protuberance, as shown in FIG. 22(*a*). It will be understood that one or both retaining structures may include ramped features and/or stabilizing features. In the example embodiment shown in FIG. 22(*a*), retaining structure 470 includes protuberance 475, while retaining structure 480 includes both protuberance 485 and ramp 490.

The groove or protuberance may be useful for stabilizing the position of the tissue construct at a pre-selected height, while the ramped feature allows for the subsequent removal of the tissue construct without risking local damage to the tissue construct. This may be achieved by first removing the tissue construct from retaining structure having the ramped feature (optionally by bending the retaining structure inward), thereby releasing the tension in the tissue construct, after which the tissue construct may be easily removed from the retaining feature having the protuberance or groove.

In other embodiments, the microwell of the microfabrication platform may include a ramped base structure, such as a truncated conical structure, extending upwardly and inwardly from the microwell base to form an upper platform supporting the retaining structures. Such an embodiment is shown in FIG. 22(*b*), which shows an array of microwells 700, each including a well bottom (base) 705, on which is provided a truncated conical support 710 that supports retaining structures 715. Although retaining structures 715 are shown absent of stabilizing features, it is to be understood that any of the stabilizing features disclosed herein may be included on, or incorporated into, retaining structures 715. As described further below, such a ramped base support can be employed to form tissue structures having a ring geometry, even when the retaining structures are dual posts that would, in the absence of a ramped support, produce a tissue structure that is attached between the dual posts.

FIGS. 22(*c*)(*i*)-(*v*) illustrate an example implementation of an array of microwells including ramped support structures (conical supports), where the microwells are provided in the form of a 96 well microplate. The microplate includes wells 700, having a truncated conical supports 710 and retaining structures 715 integrally formed therein. Truncated conical support 710 includes conical/ramped surface 712 and upper platform 714. It is to be understood that although conical support 710 is formed as a recessed surface in the bottom of the microwell, conical support 710 may alternatively be provided as a solid material. Furthermore, although conical surface 712 is shown as a straight surface defined by a single conical angle, the profile of surface 712 may take on a variety of shapes, such as, for example, a curved profile (e.g. a parabolic curve) or a stepped profile. The straight profile shown may be beneficial in allowing the optical observation of the tissue construct during its formation with less optical distortion.

As shown in the Figure, example microwell 700 also includes a side wall that includes a lower wall portion 724 having a height (depth) that is suitable for containing the cell/collagen pre-polymerized mastermix, and an upper wall portion 726 having a diameter that decreases towards the lower portion. Upper wall portion 726 is thus configured such that the pre-polymerized mastermix or other reagents provided to well 700 are directed downwards towards the central portion of the well such that they are received within region 725 surrounding conical support 710. It will be understood that although upper wall portion 726 is shown in an example implementation as being curved, other shapes are possible, such as a straight profile (e.g. a downward truncated conical shape).

Referring now to FIG. 22(*d*)(1-4), the steps in an example seeding and remodeling process are shown. In panel 1 of the Figure, collagen gel is seeded with cardiomyocytes. The resulting unpolymerized mixture is received within region 725, such that upper platform 714 is not covered.

By filling the microwell such that upper platform 714 remains uncovered by the unpolymerized mixture, such that the retaining structures 715 are not contacted by the unpolymerized mixture, the tissue construct initially forms into a ring surrounding conical surface 712. Accordingly, the volume of the microwell surrounding the ramped support is sufficiently large to contain an amount of unpolymerized matrix that is suitable for forming the tissue construct, and the volume is also large enough so that the upper platform of the ramped support structure is not covered by unpolymerized matrix. This prevents the initial, and subsequent, formation of tissue between the retaining structures, leading to a ring-shaped tissue construct.

As the remodeling process continues, the ring-shaped tissue construct slides up conical surface 712, as shown in panel 2, and culture media is added to support further remodeling. The tissue construct is subsequently bound and retained by retaining structures 715, as shown in panels 3(*a*) and 3(*b*), and is optionally constrained by stabilizing features, as described above. As shown in panel 4, retaining structures 715 may be configured to flex under the tension produced by the tissue construct during the remodeling process, in order to provide a mechanical force transduction means.

For example, the present embodiment may be employed to perform a functional assay for contractive cell types, which can be used for applications such as drug screening applications. In one example implementation, cardiac tissue constructs were obtained by the following protocol: pipetting approximately 9 μl of cell-laden matrix into the trough of each well, as shown in the panel 1; polymerizing the matrix in an incubator for approximately 20 minutes; slowly adding 150-200 uL of cell culture media into each well over top of the polymerized collagen gel, as shown in the panel 2, and returning the microwell to the incubator; after which the cells remodel around the two posts as the cells start to form a tissue. When the cells form a 3D tissue around the two posts, which has been observed to occur approximately 2-5 days after seeding, depending on the cell type, the tissue remodeling plateaus as shown in panels 3 (*a*) and (*b*). When an electrical stimulus is applied to responsive tissue types (cardiomyocytes), the deflection of the posts can be measured which can be used to determine the contractive strength of the tissue.

The aforementioned multi-microwell microfabrication embodiment (which may be referred to as a tissue microring design) can be used to generate ring-shaped tissues of a wide variety of cell types and configurations, including multiple cell types in a unibody system, as further described below. This may be advantageous for several reasons, which include but are not limited to: ease of production and sterilization, lack of leakage, increased oxygen permeability, and increased seeding efficiency. As noted below, devices with arrays for microwells (e.g. in a microplate format) may be produced by casting PDMS (silicone elastomer) into a 3D-printed master mold. Once cured, the PDMS mold can be pried out of the mold and ready for use.

In some embodiments, the ramped structure need not support multiple posts, and may support, or terminate in the form of, a single retaining structure for retaining a ring-shaped tissue construct. An example implementation of such an embodiment is shown in FIG. 22(*e*), where a series of photographs illustrate the process flow of forming a ring-shaped tissue construct in a microwell format, in which each microwell contains an integrally-formed microfabrication platform having a ramped support in the form of a conical base, and a disc-shaped pillar (retaining structure) connected or integrally formed with the ramped support. The substrate was constructed using a 3D-printed mold and molded with PDMS. Once autoclaved and coated with Pluronic™ Acid overnight, 20 uL of cell-laden collagen was pipetted into the circular reservoirs. Tissues remodeled around the single pillar in the center of the well to form arrhythmia model cardiac microtissues.

In FIG. 22(*f*)(*i*)-(*iv*), the effect of the number of cells per well is illustrated. Each well (i)-(iv) depicts cardiac microtissues composed of increasing cell density. Increasing cell density results in tissues with larger cross-sectional area.

In FIG. 22(*g*)(*i*)-(*ii*), depict micrographs of cardiac microtissues within the system, where (i) shows 100,000 cells per well under brightfield and (ii) shows the same microtissue under 488 nm light depicting GFP-expressing hPSC-derived CM.

In FIG. 22(*h*), an image is provided showing microtissue composed of Human umbilical vein endothelial cells (HUVECs) and hPSC derived hepatocytes. Aggregates of hPSC-derived hepatocytes and single cells of HUVECs were mixed together at 100,000 cells per tissue. Tissues remodel within 1-2 days.

In FIG. 22(*i*), an image is provided showing microtissue composed of mouse myoblasts differentiated into myotubes. Muscle cells were seeded at 100,000 cells per tissue. Tissues remodel within 3-4 days. Tissues were observed to be contracting spontaneously (after differentiation) within 3-4 days.

Once cells have been isolated in a single cell suspension and mixed in with unpolymerized matrix, cell-laden unpolymerized matrix is pipetted into each well and the mixture may be slowly released as the pipette tip is traced along the outer-ring (for example, with dimensions 1.5 mm in thickness, with inner diameter of 2.5 mm and an outer diameter of 5.5 in one example implementation of the design). It is noted that this protocol can be implemented manually, or in an automated fashion, e.g. via a robotic pipetting (liquid dispensing) system. Several hours after cell seeding, the cells remodel into a tissue around a central post (2.5 mm in diameter and 3.0 mm in height in one iteration of the design). It is not necessary to centrifuge the plate during the seeding process as the curvature of the side walls guides the unpolymerized cell-laden collagen into the remodeling reservoir at the bottom of each well. Numerous cell lines can be used to generate tissues and can be imaged under a digital microscope. As shown elsewhere in the present disclosure, several experiments have been performed to test the viability of the tissues, uniformity of the tissue, and the remodeling time. The tissues exhibited very uniform (with deviations as low as ~12% from the mean) thicknesses and remodeled to their final thickness in under 2 days.

In some embodiments, the microfabrication platform is integrally formed in the microwell, e.g. via the 3D printing and molding methods described herein. Two distinct features/benefits of the such an integrated/monolithic embodiment are as follows: (i) since the microwell substrate/base is integrally formed with the microfabrication platform, there is no need to glue anything into the bottom of the microwell, thus eliminating any possibility of leakage; and (ii) there may be little or no cell loss during the cell seeding process—as all of the cells may be provided to the microwell such that they contribute to the formation of the generated tissues.

Microtissue Platform Having Force Sensor with Amplified Response Based on Height of Stabilizing Features It may be desirable or important to measure the force of contraction exerted by the microtissues during and/or after their formation. As described above, this may be achieved by employing retaining structures that are configured to deflect in response to the tension applied by the tissue construct.

The aforementioned embodiments, in which stabilizing features are provided the between the base of the microwell and the distal end of the retaining structure, may be employed to provide amplification of the deflection of a retaining structure in response to applied tension. Such an embodiment may be employed, for example, to increase the sensitivity of the force measurement, and/or increasing the dynamic range of the force measurement.

For example, in one embodiment, a force-amplified microfabrication platform may include at least two retaining structures, where at least one of the two retaining structures is a microcantilever that includes a stabilizing feature, and wherein the stabilizing feature is located between the base of the microwell and the distal end of the retaining structure. In such an embodiment, the local deflection of the retaining structure at the height of the tissue construct is amplified due to the extension of the retaining structure vertically beyond this height.

FIG. 23 illustrates an example implementation of such an embodiment, where FIG. 23($a$) shows a microfabrication platform 500 including microwell 510 and two microcantilever retaining structures 520 and 530, each having stabilizing features 525 and 535. Each stabilizing feature is configured to stabilize a tissue construct at height $h_1$ relative to the microwell base, and where the total cantilever extends for an additional height $h_2$ beyond height $h_1$, such that the total cantilever height is $h_T=h_1+h_2$.

In FIG. 23($b$), microfabrication platform 500 is shown in which microcantilevers 520 and 525 are deflected due to the contraction of tissue construct 400. As can be seen from the Figure, each microcantilever deflects due to the tension from the tissue construct, where the deflection is $d_1$ and $d_2$ at the point of stabilization of the tissue construct, and at the distal portion of the microcantilever, respectively. As a result, a measurement of the tension in the tissue construct based on displacement $d_2$ will result in an amplified displacement (signal) relative to a measurement based on $d_1$, where the amplification is given by approximately $(h_1+h_2)/h_1$ (based on similar triangles).

It is to be understood that the present embodiment is but one example of a microfabrication platform exhibiting force transduction amplification, and that other many other variations are possible. For example, it can be seen that FIG. 24 provides a degenerate force measurement (showing equal flexing of retaining features 550 and 555), and in alternative embodiments, only one of the two retaining structures need function as a microcantilever.

It is to be understood that according to various embodiments, retaining structures with intermediate stabilizing features can be arranged in biaxial fashion or a uniaxial fashion. In general, the more that cantilevers are present, the smaller the deflection of the retaining structures will be (with the largest deflections being in the uniaxial configurations). As such, it may be beneficial to incorporate the preceding amplification embodiments into configurations that will do not inherently produce large deflections, such as a multi-post biaxial configuration.

It is to be understood that the stabilizing feature should be able to stabilize the position of the microtissue, and accordingly, in implementations with weakly flexible retaining structures, it may be preferable to position the stabilizing features at position remote from the distal end of the retaining structure. On the other hand, if the stabilizing feature is provided too low on the retaining structure (e.g. proximal to the well bottom), and if the retaining structure is to function as a microcantilever, then then dynamic range of the deflection of the retaining structure may be reduced (depending on the stiffness of the retaining structure). Accordingly, in some example implementations, stabilizing features may be provided at a height ranging from approximately 250 µm to 500 µm from the base of the microwell.

Arrayed Format of Microtissue Platform

As noted above, in some embodiments, microwells having microfabrication platforms provided or formed therein may be provided in an arrayed format, such as in a microplate (e.g. a 24, 96, 384 or 1536 well microplate). Examples of such layouts are provided below in the section describing microfabrication methods.

An example of the formation of miniaturized cardiac microtissues of various geometries in an arrayed format is shown in FIGS. 6 ($a$)-($e$). When executing high content and high-throughput screens, it can be important to maximize the amount of samples in the study. An arrayed format allows more replicates to be generated within a single well. This may be beneficial in addressing issues or problems with lack of tissue formation in any single microwell. An average of many arrayed wells may be employed to produce a reliable output. To enable HCS, the microtissues should retain the ability to be functionally measured. An optimal balance between miniaturizing and maintaining the hallmarks of functional cardiac tissue is a criterion.

In some implementations, microfabrication platforms (and the microwells containing such platforms) may be arrayed in a unidirectional format to facilitate continuous perfusion of cell culture media and drugs. This type of system would be much more physiological and would be adaptable to microfluidic systems.

Microfabrication Methods

Microfabrication platforms with retaining structures that include stabilizing features according to the above embodiments may be fabricated as follows. In one example implementation, a microfabrication approach may be followed in a manner similar to that described above and illustrated in FIG. 1($a$). Either photolithography can be applied form beginning to end to generate layers features, whereby allowing the features to be added sequentially (see the aforementioned SU-8 microfabrication protocol), or a post-processing method can be applied where tall straight walls are engineered using the standard photolithography method, and retaining features added manually afterward. A post-processing method may be employed where a basic straight vertical post is microfabricated through traditional SU-8 based means and then grooves, protuberances, and ramps are added afterward manually under a stereomicroscope. This is done by applying a small volume of hardening material (epoxy) for a protuberance or milling away material for a groove.

However, an alternative method to generate these structures is through high-resolution 3D-printing. A 3D-printing approach may be employed where one or more steps of the design (including the various retention features) is generated using 3D modeling software and printed using a high-resolution 3D printer. In one embodiment, the final file type may be exported as a high fidelity '.stl' file using a standard 3D modeling software such as AutoCad or SolidEdge.

FIG. 6(f) illustrates an example 3D printing method for the microfabrication of a microplate having microwells with tissue microfabrication platforms integrally formed therein. Firstly, a positive mold is 3D printed (in the present case, an Objet24 3D printer from PROTO3000 was used) from a 3D computational model. The material used to print the master was VeroWhite. Once the mold is printed, it may be post-cured, for example, at 60 degrees Celsius for 24 hours, to polymerize any residual material. This printed master is then used to mold replicates of desired platform geometries containing the desired stabilizing features. The mold is then used to make a negative with PDMS. PDMS is cast on top of the mold and cured for 24 hours at 60 degrees Celsius. The negative PDMS mold is coated with silane and then molded again with PDMS to create a positive. To generate a durable and easily demoldable master mold, polyurethane is used to create a mold form the positive PDMS mold. From this polyurethane negative mold, positive PDMS substrates can be generated indefinitely. That is, the end result of the process to the left is a polyurethane master mold, which allows the one to bypass all the steps depicted in the left hand box and to follow the rapid microfabrication procedure depicted in the box at the bottom of FIG. 6(f). This means that the user need only to follow this simplified procedure as long as a master mold is successfully created. Finally, the mold is removed from the polyurethane master, inserted into an autoclave bag, and autoclaved before use. Substrates are coated with Pluronic™ Acid before washing and seeding cells and ECM.

Arrows depict the transition steps (note: some transitions involve an intermediate process, such as placing the mold in the oven).

It will be understood that the material properties and/or material dimensions may be selected in order to obtain retaining structures with mechanical properties that are suitable for force transduction measurements during the remodeling process. For example, the formula shown in FIG. 6(g) depicts the equation used to determine the force per unit length in example microfabrication platforms shown herein, where q=force per unit length, d=displacement of the top of the post, E=Young's modulus of PDMS, I=moment of cylinder, a=length of tissue contacting the post, L=height of post.

FIG. 6(h) illustrates an example method of producing a replica microplate based on a master microplate mold formed via 3D printing. The steps shown in the Figure are as follows. In step (i), a 3D printed mold (positive) is fabricated, for example, using the method described above in FIG. 6(f). In step (ii), a PDMS negative is cast from the original mold. In step (iii), a PDMS positive is cast from negative PDMS mold. In step (iv), a negative polyurethane mold is created from the positive PDMS substrate. In step (v), a PDMS substrate is molded from the polyurethane master mold and is then autoclaved. In step (vi), a Pluronic™ acid-coated PDMS substrate is seeded with cell-laden collagen. In step (vii), droplets of cell-laden collagen are formed at the inner edges of wells. In step (viii), after gently tapping the plate on a flat surface, the droplet of cell-laden collagen has dropped into the ring-shaped reservoir. Finally, in step (ix), after polymerization in the incubator for 20 minutes, media is added to each well.

FIGS. 6(i) and 6(j) are the original 3D AutoCAD models of the 3D printed molds of (i) the arrhythmia model 24-well plates, and (j) of the 96-well force of contraction platform.
Inclusion of Electrodes in Microtissue Platform In one example implementation, two flanking posts within the cardiac microwire microwell were integrated with platinum wire electrodes, to provide electrical point stimulation capability (FIG. 11(b)). Electrodes can be incorporated according to a variety of methods. In one example implementation, retaining structures may be formed housing the electrodes. For example, conductive polymers that are elastic can be used to fabricate deflecting posts that also can serve as stimulating and recording electrodes. In more advanced 3D-printing techniques, multiple materials can be designed and printed simultaneously, including conductive materials. An embodiment with conductive point sources (conductive materials functioning as electrodes) embedded into an elastic post which is insulated within the non-conductive elastic post can be used to deliver a point source electrical stimulation to the tissue.

In another embodiment, metal electrodes can be integrated onto or into the floor of the microwell to allow for stimulation and recording. This can be achieved, for example, by utilizing the 3D printer to design conductive materials into the substrate floor as opposed to the post themselves.

In some embodiments, the simulating electrodes may be placed close to each other, in order to allow for "point stimulation" rather than field stimulation. Point stimulation recapitulates physiological conditions much better than field stimulation.

Much smaller voltages can be used for point stimulation and this allows for more physiological ranges which may limit electrical field-induced cell damage and death. Stimulation less that 1 V can be used in these point stimulation regimens. Spacing for the electrodes may be in the range of approximately 0.2 mm to 2 mm. Additionally, multiple point sources can be installed within one tissue in order to manipulate conduction velocity. For example, point stimulation sources can be setup on either side of the tissue on the distal end in order to modulate the direction of action potential propagation.

Example electrode materials can include platinum, carbon, indium tin oxide, and proprietary conductive polymers (amenable for 3D printing).

In one example implementation, suitable electrode dimensions are approximately of 50-100 μm in diameter. The height between the electrode surface and the tissue may depend on the excitability of the tissue. In one example embodiment, the height between the electrode surface and tissue may range between approximately 0.25-0.5 mm.

In one example implementation, at least one of the retaining structures may be a pair of adjacent structures, and where each adjacent structure in includes an electrode, such that adjacent structures perform the dual role of acting as a retaining structure and providing a pair of electrodes for applying point stimulation. Such an embodiment is illustrated in FIG. 25, where a first retaining structure includes posts 560 and 565, and a second retaining structure includes posts 570 and 575.
Microtissue Constructs with Multiple Cell Types In one embodiment, a microtissue seeded with endothelial cells (cell type 1) can be generated, and then tissues composed of heart cells (cell type 2) can be generated around it by seeding another layer of cells and ECM over top (FIG. 26). This would result in a tissue with a vascular core (based on endothelium) with functional heart cell-based tissue on the outside once remodeling is completed. Interactions of these cells on the border regions can be observed as well. Cell densities of each type would be optimized for specific growth rates related to the respective cell line. Additionally, cell culture media would be a combination of the two types of media required for each cell type.

Figure 26A:
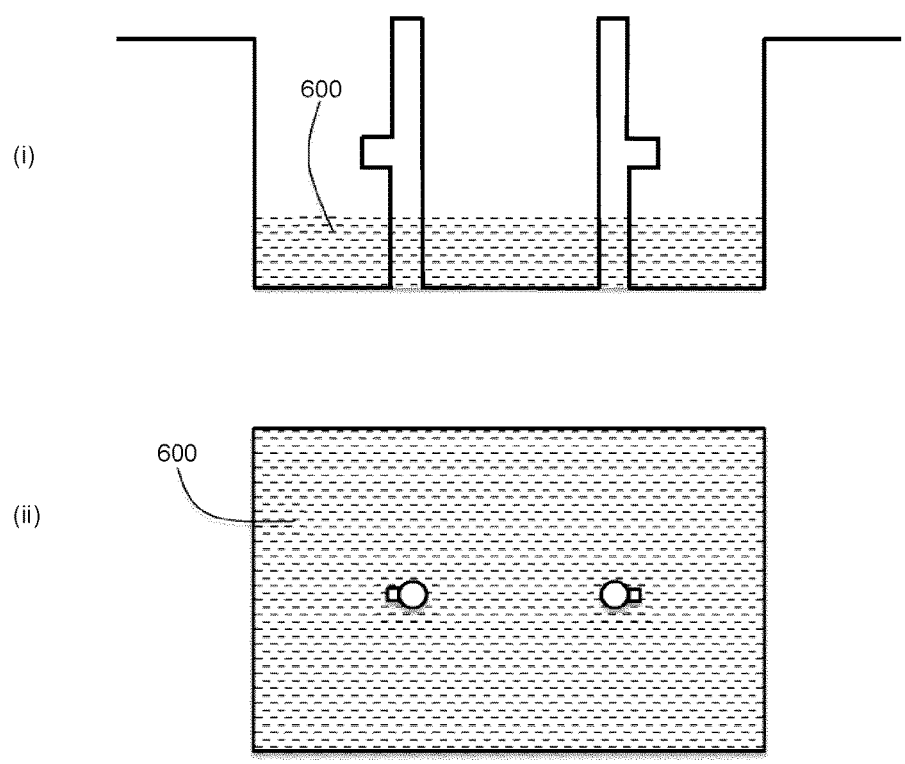
Figure 26B:
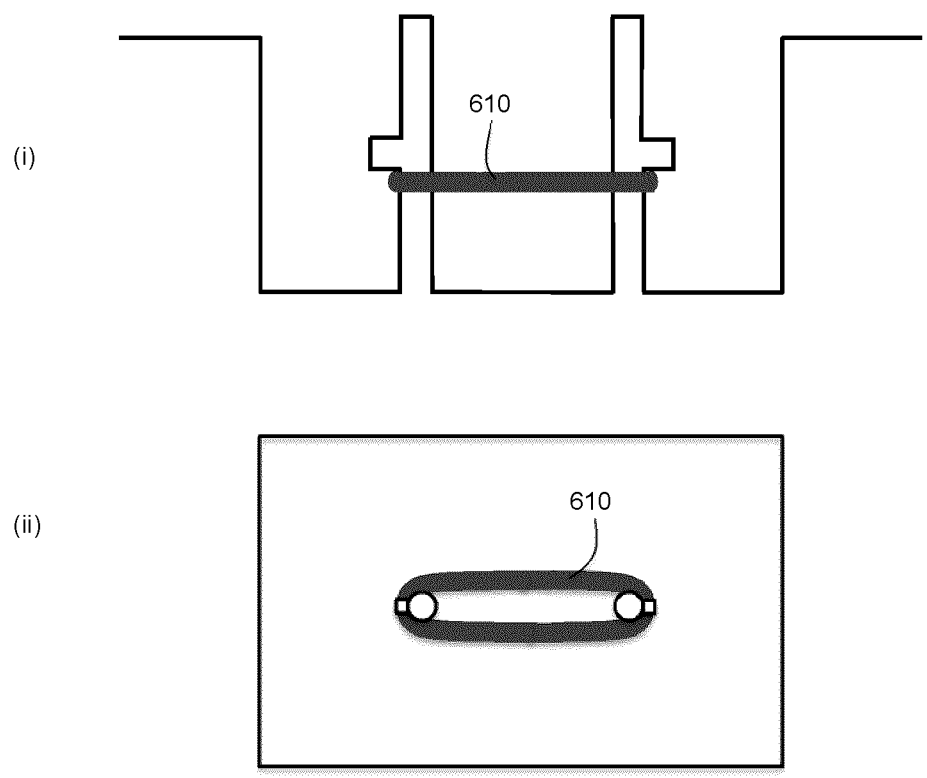
Figure 26C:
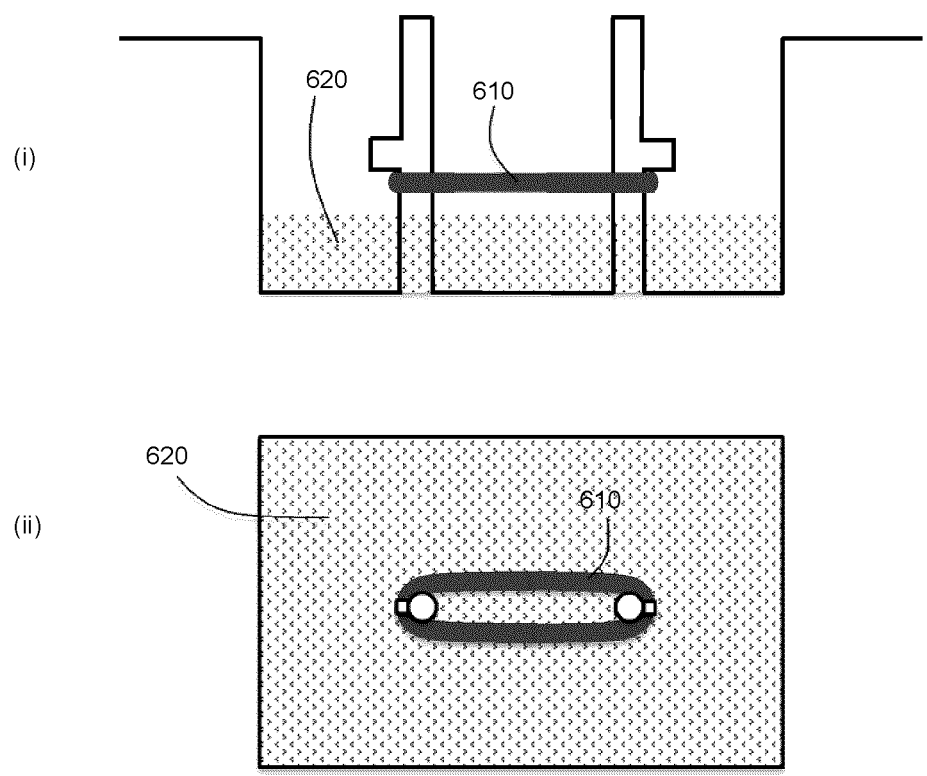
Figure 26D:
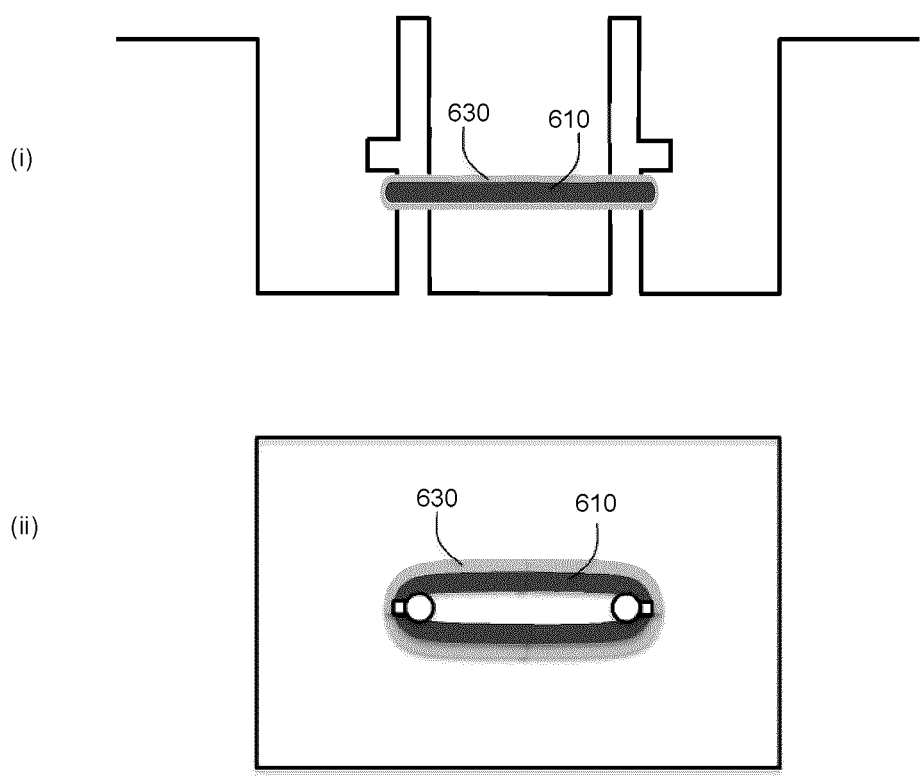

An example method for forming such a multiple cell dual construct is shown illustrated in FIGS. 26(a)-(d). In FIGS. 26(a) and (b), a first seeding mixture 600 is provided to a microfabrication platform, and is remodeled into a first tissue construct 610. Subsequently, as shown in FIGS. 26(c) and (d), a second seeding mixture 620 is added to a microfabrication platform (with tissue construct 610 present), and is remodeled into second tissue construct 630, which forms around first tissue construct 610.

This process is illustrated in FIGS. 27(a)(i)-(iv), in the context of the ramped microwell structure that was also illustrated in FIGS. 22(b)-(d). In panels (i) and (ii), an initial tissue construct formation process is illustrated, in which a tissue construct including cells of a first type 750 is formed around retaining structures 715. In panels (iii) and (iv), the process is repeated for a second cell type, such that the tissue construct formed includes both cell types.

FIGS. 27(b) (i) and (ii) shows fluorescence microscopy images of two different regions of a dual-cell type tissue construct formed according to such an embodiment, showing the two different cell types tagged with different dyes (type 1 is tagged with GFP and type 2 is tagged with cell tracker dye red). Both cell types are of an immortalized mouse fibroblast cell line.

FIGS. 27(c)(i)-(iii) show fluorescence microscopy images of the composite tissue construct at a lower magnification, showing (i) fluorescence from cell type 1, (ii) fluorescence from cell type 2, and (iii) fluorescence from both cell types. Cell type one was seeded and allowed to remodel for 3-4 days. Once remodeled, a second cell type (type two) was added into the reservoir and allowed to remodel around the first tissue type. The result was a layered microtissue. This model can be also be iterated for layered tissue types greater than two.

Modeling of Stress and Contractile Sarcomeres in Cardiac Microwire

The microfabrication approach described above may be supplemented with a computational modeling method to support the rational design and fabrication of a miniaturized 3-D microtissue platform. The modeling may be performed, for example, to ensure that cells maintain high sarcomere expression, to predict the aligned microtissue architecture due to tension, and to model integrated electromechanical stimuli.

Accordingly, in some embodiments, methods of fabrication of cardiac microwires included the use of in-silico modeling to spatially predict and/or evaluate patterned mechanical stresses distributed within various 3-D tissue geometries. To illustrate the role and utility of such modeling, two simple microtissue geometries were selected to model (FIG. 2(b)) using a finite element-based simulation of microtissue contractility: microtissue geometries under 1) biaxial and 2) uniaxial intratissue tension forces (BITF and UNITF respectively).

Unlike existing in-silico methods, which are based on a model for predicting formation of stress fibers in non-muscle cells, the present model was formulated to predict sarcomere formation and alignment in cardiac tissue during its formation. The evolution and contractility of sarcomeric filaments in the microtissues was simulated by adapting a previously proposed framework (Deshpande et al., 2006) to the modeling of cardiac tissue formation. While this framework has previously been implemented for the modeling of stress fibre contractility in a range of cell phenotypes (Deshpande et al., 2007; Pathak et al., 2008; McGarry et al., 2009; Legant et al., 2009), the preceding applications related to non-muscle cells, or did not involve a prediction of sarcomere formation and alignment. Accordingly, in the present embodiment, the model is adapted for the simulation of sarcomeric filaments in cardiomyocytes on the basis that both stress fibres and sarcomeric filaments are composed of and operate via actin-myosin interactions.

According to one example implementation, the formation of aligned contractile sarcomeres at each point in the tissue is predicted by the output parameter Π, defined as the difference between maximum and mean sarcomere activation level ($\Pi = \eta_{max} - \bar{\eta}$). Highly activated, aligned sarcomere formation in a dominant direction is predicted by a value of Π close to 1. In contrast, a value of Π close to 0 predicts that no dominant sarcomere has formed at that point.

As shown below, predicted distributions of Π are directly comparable with fluorescent microscopy images stained for cardiac Troponin T and Alpha-Actinin, whereby removal of background fluorescence reveals the distribution of dominant sarcomere formation.

In order to investigate the relationship between sarcomere formation and the stress state of the tissue, a non-dimensional effective stress $\hat{S} = (\sigma_{max}^P - \sigma_{min}^P)/\sigma_{max}^P$ was defined where $\sigma_{max}^P$ and $\sigma_{min}^P$ are the maximum and minimum principal stress, respectively. Model parameters were calibrated based on experimentally observed changes in the width of the uniaxial tissue construct.

Figure 1B:
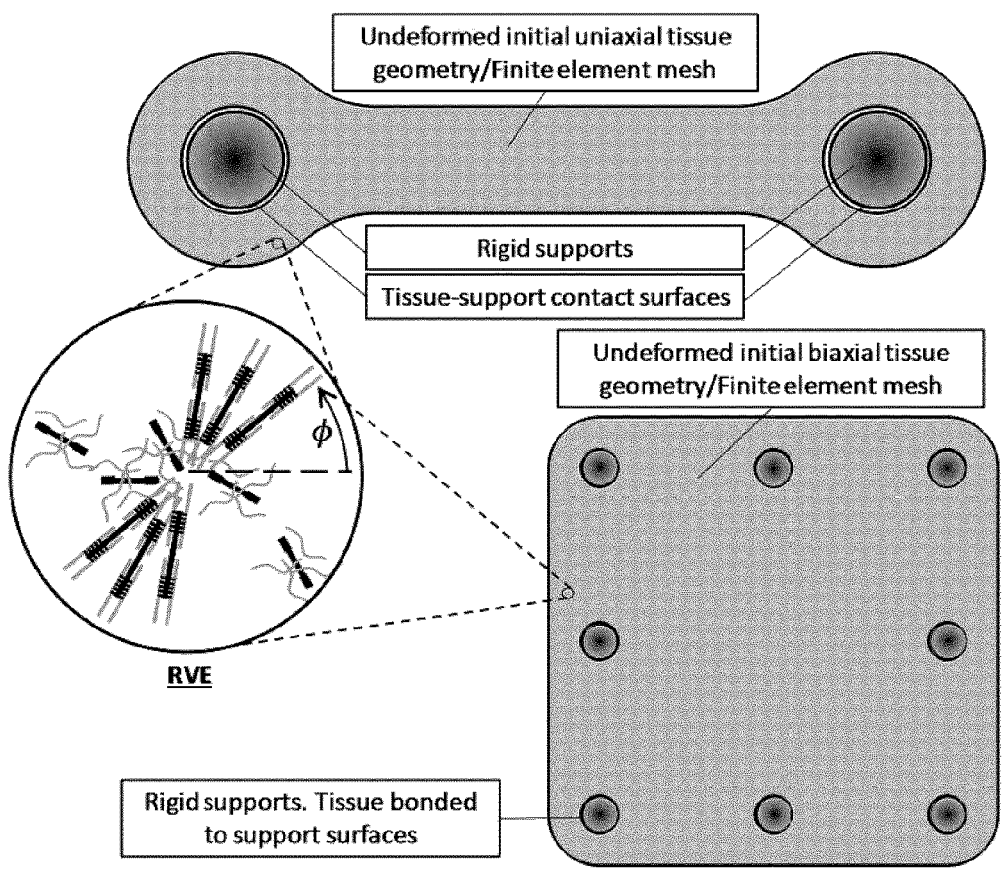
FIG. 1(b) shows two microtissue geometries which were simulated using a finite element-based computational model: one with biaxial intratissue tension force (BITF), and the other with uniaxial tension force is henceforth termed "cardiac microwire". Simulations allow sarcomeric alpha-actinin formation in all directions in the finite element mesh. A cartoon of a representative volume element (RVE) is provided for illustration.

In one example implementation of the model, the microtissue is modeled as a continuum, in which sarcomeric filaments are free to form in all directions at all points in the tissue, as illustrated in the inset to FIG. 1(b). The non-dimensional sarcomere activation level, $\eta(\phi)$, is computed in all directions ($\phi$). A first order kinetic equation governs the evolution of sarcomeric filaments, whereby filament formation is driven by a signal that decays exponentially with time (first term on the RHS of equation 1).

$$\dot{\eta}(\phi) = [1 - \eta(\phi)]\frac{Ck_f}{\theta} - \left(1 - \frac{\sigma(\phi)}{\sigma_0(\phi)}\right)\eta(\phi)\frac{k_b}{\theta} \quad (1)$$

Sarcomere contractility is modeled using a Hill-type equation, whereby the tension generated by a sarcomeric filament decreases with increasing shortening velocity. Hence, as sarcomeric filaments shorten, a reduction in tension occurs. Such a reduction in tension below the isometric value leads to partial dissociation of the sarcomeric filament, as captured by the second term on the RHS of equation 1.

Sarcomere formation is assumed to be driven by an exponentially decaying signal, where the signal intensity, C, in the tissue is given as $$C = e^{\left(\frac{-t}{\theta}\right)}$$

(A1)

The signal may be thought of as the concentration of calcium or Rho. θ is a constant that controls the decay rate of the signal and t is the time elapsed since the signal initiation.

The contractile behaviour of a sarcomeric filament, orientated in the direction φ, is assumed to obey a Hill-type tension-strain rate relationship, similar to that of skeletal muscle (both skeletal muscle and cardiomyocyte sarcomeric filaments produce tension due to actin-myosin interactions). The tension in a sarcomeric filament, σ(φ), which is generated by cross-bridge cycling of actin-myosin pairs, is given as:

$$\frac{\sigma(\phi)}{\sigma_0(\phi)} = \begin{cases} 0 & \frac{\dot{\varepsilon}(\phi)}{\dot{\varepsilon}_0} \leq -\frac{\eta(\phi)}{k_v} \\ 1 + \frac{k_v}{\eta(\phi)}\frac{\dot{\varepsilon}(\phi)}{\dot{\varepsilon}_0} & -\frac{\eta(\phi)}{k_v} \leq \frac{\dot{\varepsilon}(\phi)}{\dot{\varepsilon}_0} \leq 0 \\ 1 & \frac{\dot{\varepsilon}(\phi)}{\dot{\varepsilon}_0} > 0 \end{cases} \quad (A2)$$

where σ(φ) is the sarcomere tension, $\sigma_0(\phi)$ is the isometric tension. The model parameter $k_v$ determines the slope of the Hill curve, representing the reduction in stress upon increasing the shortening strain rate, $\dot{\varepsilon}(\phi)$, by $\dot{\varepsilon}_0$. The isometric tension of the sarcomere depends on the activation level of the sarcomere, η(φ), whereby $\sigma_0(\phi)=\eta(\phi)\sigma_{max}$. The model parameter $\sigma_{max}$ is the maximum tension in a fully activated sarcomere.

A first order kinetic equation governs the evolution of sarcomeric filaments, whereby filament formation is driven by a signal that decays exponentially with time (first term on the RHS of equation A3).

$$\dot{\eta}(\phi) = [1-\eta(\phi)]\frac{Ck_f}{\theta} - \left(1 - \frac{\sigma(\phi)}{\sigma_0(\phi)}\right)\eta(\phi)\frac{k_b}{\theta} \quad (A3)$$

As outlined in equation A2, as sarcomeric filaments shorten, a reduction in tension occurs. Such a reduction in tension below the isometric value leads to partial dissociation of the sarcomeric filament, as captured by the second term on the RHS of equation A3.

As previously mentioned, the simulations performed in the present study are fully predictive, with sarcomeric filaments being allowed to form in all directions in the two-dimensional tissue. In equation A2 the axial strain rate $\dot{\varepsilon}(\phi)$ in the sarcomeric filament at angle φ is determined from the two dimensional strain rate tensor at each integration point such that $$\dot{\varepsilon}(\phi)=\dot{\varepsilon}_{11}\cos^2\phi+\dot{\varepsilon}_{22}\sin^2\phi+\dot{\varepsilon}_{12}\sin 2\phi \quad (A4)$$

The active sarcomeric contribution to the stress tensor at each integration point is given as $$S_{ij}^A = \frac{1}{2\pi}\int_{-\pi/2}^{\pi/2}\begin{bmatrix} 2\sigma(\phi)\cos^2\phi & \sigma(\phi)\sin 2\phi \\ \sigma(\phi)\sin 2\phi & 2\sigma(\phi)\sin^2\phi \end{bmatrix}d\phi \quad (A5)$$

The constitutive formulation is completed by the addition of a passive elastic contribution to represent the collagen matrix and the non-contractile components of cardiomyocytes. The passive stress is given as:

$$S_{ij}^P = \frac{E}{1+v}\varepsilon_{ij} + \frac{Ev}{(1-2v)(1+v)}\delta_{ij}\varepsilon_{kk}, \quad (A6)$$

such that the total stress is given as:

$$S_{ij}=S_{ij}^A+S_{ij}^P \quad (A7)$$

This constitutive framework was implemented in ABAQUS (Dassault Systemes) as a user-defined material subroutine. Microtissue geometries were meshed using four noded plane stress elements (CPS4). Post-processing of results was performed using the software Paraview.

Finite element (FE) models were created for both the "biaxial" and "uniaxial" microtissue, as shown in FIG. 1(b). Non-deformed FE geometries are based on initial microtissue geometries prior to deformation due to cardiomyocyte contractility and remodeling. The circular posts (e.g. PMDS posts as described above) used to constrain the microtissues are modeled as rigid surfaces, as these supports are several orders stiffer than the surrounding microtissue. In the case of the biaxial FE model, the microtissue is assumed to be bonded to the eight supporting circular posts, reflecting the in-vitro coating of each post with an adhesive agent. In the case of the uniaxial microtissue such an adhesive agent was not used, hence in the uniaxial FE models hard contact is assumed between the two circular rigid posts and surrounding microtissue, allowing sliding and separation of the tissue from the posts. 4241 plane stress full integration elements were used for the uniaxial geometry while 37603 such elements were used for the biaxial geometry for all analyses following an initial mesh sensitivity study.

FIG. 14(a) shows a plot of the predicted sarcomere distribution in the uniaxial tissue following 70 hours (steady state). The tissue has deformed significantly from its initial geometry (also illustrated in FIG. 9), undergoing a significant reduction in width (see also FIG. 1C). Additionally, the tissue separates from the inner surface of the circular support due to the contractile action of the sarcomeres.

A high degree of highly aligned sarcomere formation is computed throughout the central region of the tissue, with sarcomeres aligned along the major axis of the tissue. Additionally, a high degree of highly aligned sarcomere formation is computed in the narrow strips that form where the tissue separates from the supports. Low sarcomere formation is predicted in the localized "junction" region where these narrow strips meet. The predicted deformation of the tissue and the predicted distribution and alignment of sarcomeres correlates very closely with experimental observations. The evolution of tissue deformation and sarcomere formation is shown in FIGS. 9(a)-(f) at a number of discrete time-points.

FIG. 14(b) shows the stress state in the tissue, with vector directions indicating the direction of the maximum principal stress. The non-dimensional effective stress $\hat{S}=(\sigma_{max}^P-\sigma_{min}^P)/\sigma_{max}^P$ is close to 1 throughout the tissue, indicating that the stress state is highly uniaxial. A high degree of sarcomere formation is predicted in such regions of uniaxial stress. In contrast, $\hat{S}\approx 0$ in the localized "junction" region, where low sarcomere formation is predicted. It is worth noting that directions of maximum principal stress correlate strongly with the predicted directions of sarcomere formation throughout the tissue. The evolution of tissue deformation and non-dimensional effective stress $\hat{S}$ is shown in FIGS. 10(a)-(f) at a number of discrete time-points.

FIG. 15(a) shows a plot of the predicted sarcomere distribution in the biaxial tissue following 70 hours (steady state). The tissue has deformed significantly from its initial geometry, with significant curving of the of the tissue boundaries being observed. In this case, no separation of the tissue from the circular supports is permitted, as discussed above. The predicted tissue deformation corresponds closely with experimental observation. A high degree of aligned sarcomere formation is predicted in the peripheral regions of the tissue where sarcomeres are predicted to align parallel to the tissue boundaries. Additionally, moderate sarcomere formation is predicted near the four corner supports. Very little sarcomere formation is predicted in the center of the tissue. The predicted deformation of the tissue and the predicted distribution and alignment of sarcomeres correlates very closely with experimental observations. The evolution of tissue deformation and sarcomere formation is shown in FIGS. 7(a)-(h) at a number of discrete time-points.

FIG. 15(b) shows the stress state in the tissue, again with vector directions indicating the direction of the maximum principal stress. The non-dimensional effective stress $\hat{S}$ is close to 1 near the periphery of the tissue, indicating a uniaxial stress state. Again, this demonstrates a strong correlation between sarcomere formation and regions of uniaxial stress, with sarcomeres aligning in directions of maximum principal stress. In the center of the tissue $\hat{S} \approx 0$, indicating a biaxial stress state. No sarcomere formation is predicted in this region of biaxial stress. The evolution of tissue deformation and non-dimensional effective stress $\hat{S}$ is shown in FIGS. 8(a)-(f) at a number of discrete time-points.

Figure 1C:
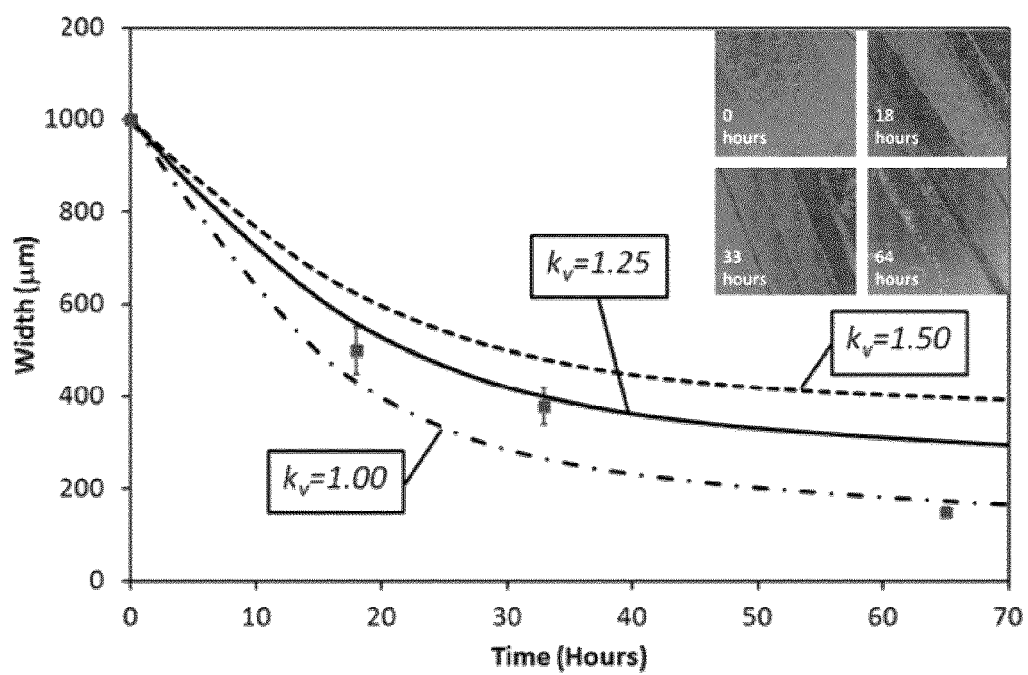
FIG. 1(c) plots experimental and simulated temporal changes in uniaxial microtissue width. Simulated results are shown for $k_v$=1.5, 1.25, 1.0. Experimental results are shown as mean±SEM. Inset: time lapse over 64 hours of remodeling of cardiac microtissues.

As shown in FIG. 1(c), a reasonable prediction of tissue deformation is obtained for a value of $k_v$ between 1 and 1.5 with a ratio of $(\sigma_{max}/E)=25$ and $\dot{\varepsilon}=0.003$ s$^{-1}$. This suggests that cardiomyocytes possess a higher value of isometric tension than NIH 3T3 cells considered in a previous study [19] where $(\sigma_{max}/E)=16$ for a microtissues constructed from 1.75 mg/ml collagen. Additionally, the low value of $k_v$ (<1.5) calibrated for cardiomyocytes in the present study indicates that the slope of the Hill curve is low for this cell type tension in comparison to 3T3 cells ($k_v=2$). This indicates that cardiomyocytes will produce a tension closer to the isometric value than will 3T3 cells for a given shortening strain rate. A value of $k_v=1.25$ is used for all subsequent simulations in the present study.

The temporal behaviour of the tissue, with a steady state tissue width being observed following 70 hours, is arbitrarily captured by adjusting the decay time of the signal C and the reaction rate constants $k_f$ and $k_b$ in equation 1 (see above). For example, in FIG. 1(c), a signal decay constant $\theta=25200$ s (7 hours) is chosen, with $k_f/\theta=0.14$ and $k_f/\theta=0.014$.

An important insight the model provides is that mechanical stress produced by intratissue tension via cell traction forces is a strong modulator of the cytoskeletal and ECM protein structure within a tissue [19]. For the present system, the model predicted areas of stress in both the BITF and UNITF microtissues as well as areas of aligned tissue and sarcomere expression. The present model simulation determined that bordering regions of the BITF microtissue experienced the highest stress (FIG. 1(d)). The lowest stress was predicted to be in the center of the BITF microtissues, with a graded continuum of mechanical stress between these points of minima and maxima.

Figure 1D:
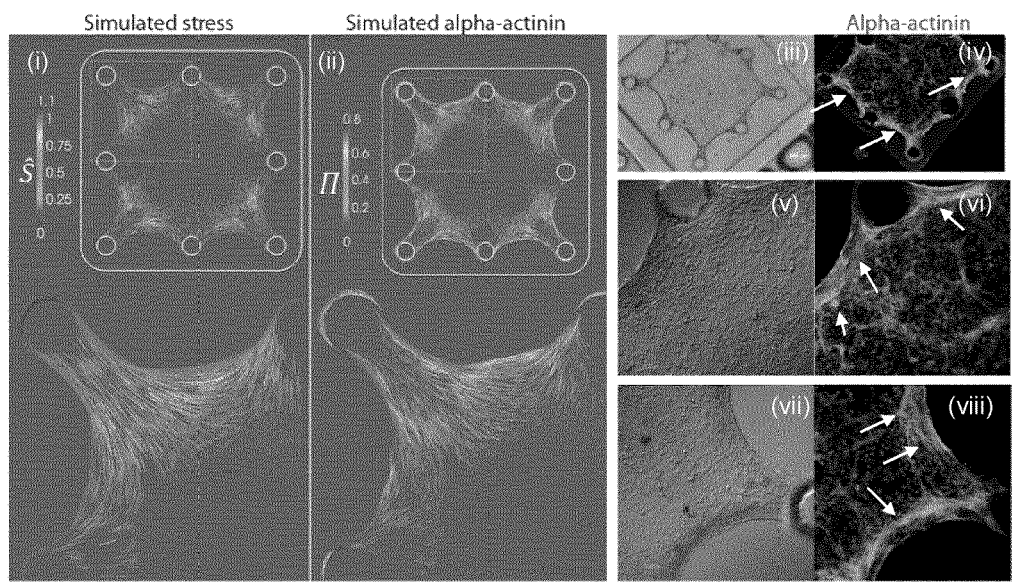
FIG. 1(d) shows results from simulations, plotting (i) stress (represented by a non-dimensional effective stress $\hat{S}$), and (ii) sarcomeric alpha-actinin expression (represented by II), in BITF microtissue geometry co-localizing in border regions, along with images of stained tissue samples for comparison.
Figure 1E:
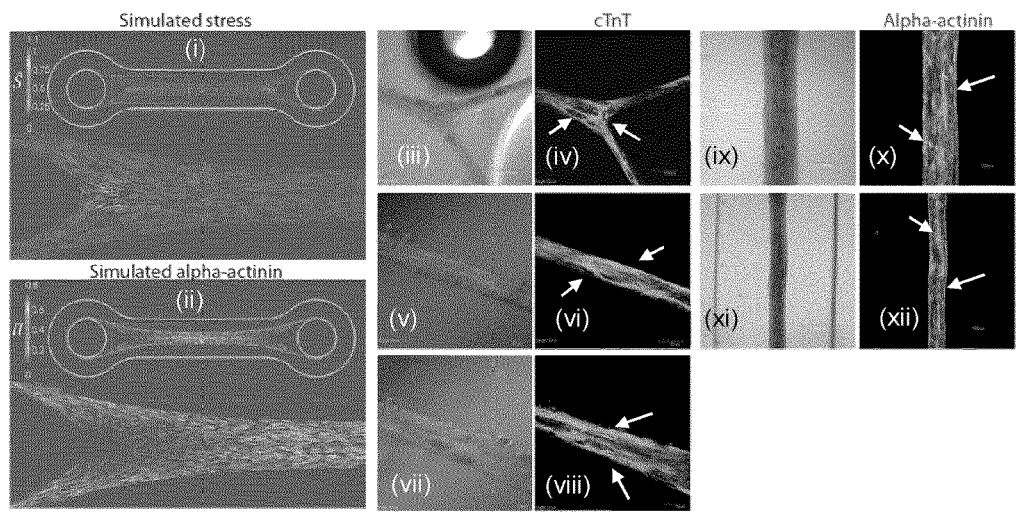
FIGS. 1(e) (i) and (ii) show results from simulations, plotting (i) stress and (ii) sarcomeric alpha-actinin expression in cardiac microwire geometry in all regions along longitudinal axis, along with images of stained tissue samples for comparison. Figures (iii)-(viii) show staining for cardiac troponin T (cTnT) of cardiac microwires (bright field on the left ((iii), (v), (vii)) and cardiac troponin T staining on the right ((iv), (vi), (viii)).
Figure 1F:
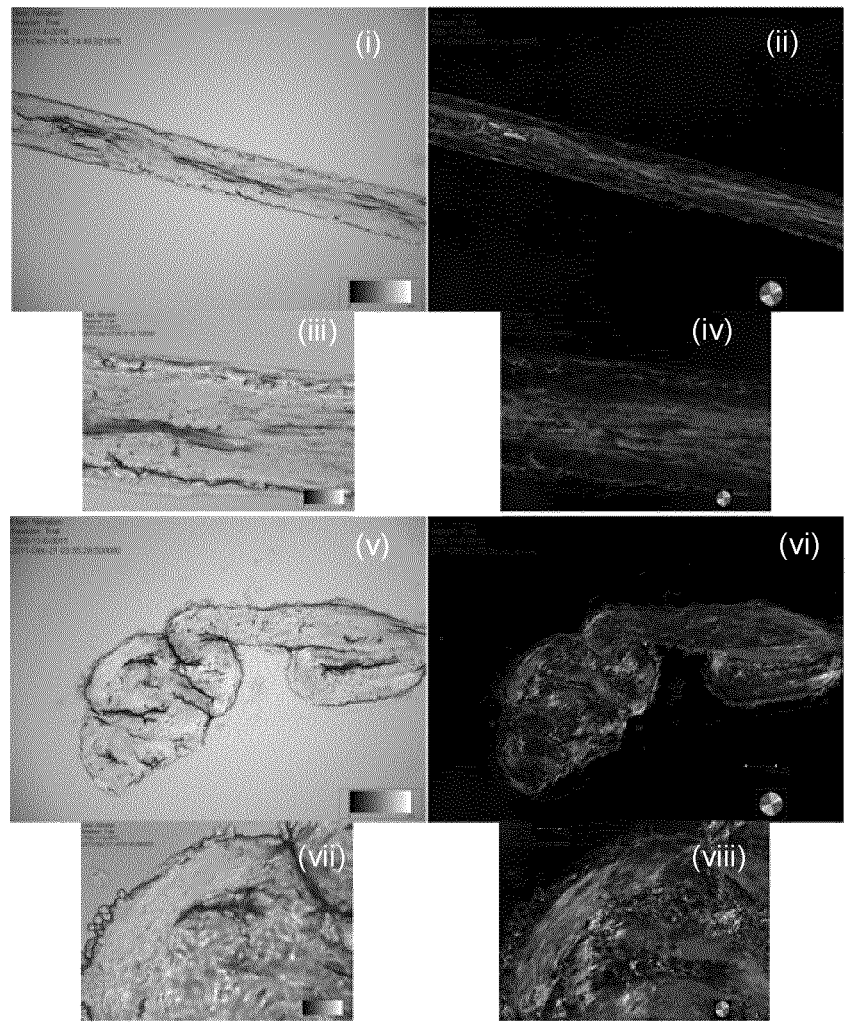
FIG. 1(f) shows images of fibrillar collagen content of a cardiac microwire, measured with a quantitative birefringence imaging system. Pixel shade corresponds to angle of birefringent fibrillar collagen in cardiac microwire. The cardiac microwire held taut shows unidirectionally aligned collagen (i)-(iv). Compacted cardiac microwire maintains fibrillar collagen alignment in direction of curl (v)-(viii).
Figure 1G:
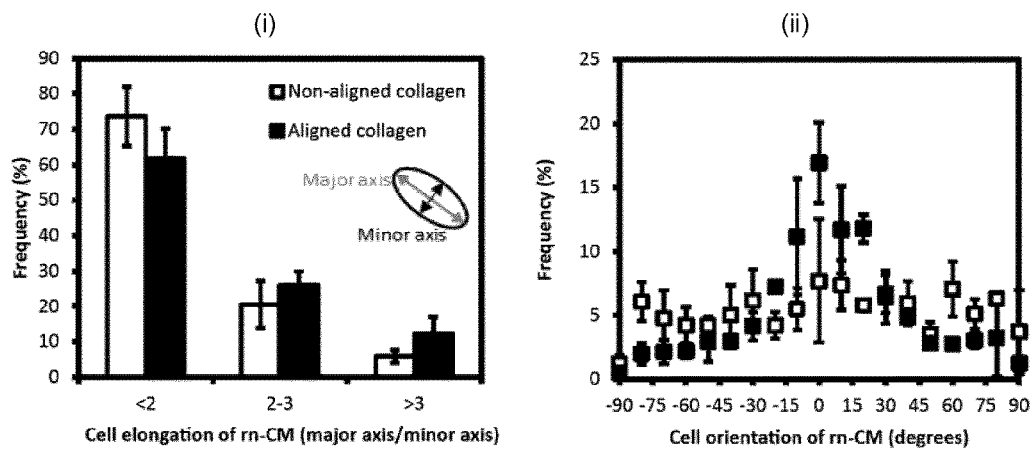
FIG. 1(g) plots (i) cell elongation and (ii) orientation of rat neonatal (rN)-cardiomyocyte on pseudo-3D aligned and unaligned collagen substrates. The measure of cell elongation is the ratio of the major axis to the minor axis of a cell. The measure of cell orientation is relative to direction of alignment of patterned collagen.
Figure 1H:
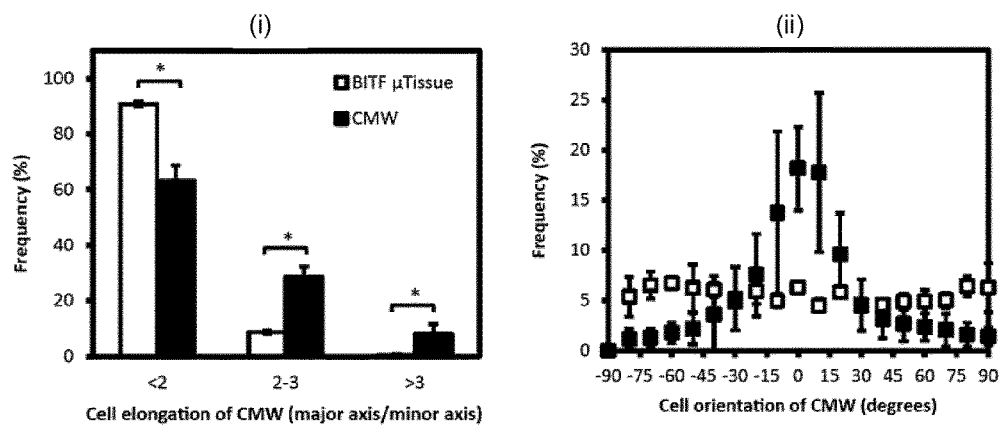
FIG. 1(h) plots (i) cell elongation and (ii) orientation of rN-cardiomyocytes in cardiac microwire. The measure of cell elongation is the ratio of the major axis to the minor axis of a cell. The measure of cell orientation is relative to direction of longitudinal axis of cardiac microwire. Data are reported as the mean±SEM., $P<0.05$ (Mann-Whitney U test).

In the UNITF microtissue, high stress was exhibited throughout the longitudinal length to produce a uniformly high regime of intratissue tension (FIG. 1(e)). As noted above, the evolution of tissue deformation and non-dimensional effective stress $\hat{S}$ for both geometries are shown (FIG. 8 and FIG. 10) at a number of discrete time-points. The model further predicted that for both microtissue geometries under biaxial and uniaxial intratissue tension forces, cardiac sarcomere protein expression is patterned in alignment in areas of high uniaxial stress (FIGS. 1(d) and (e)).

As noted above, the evolution of tissue deformation and sarcomere formation for both geometries are shown (FIG. 8(a)-(f) and FIG. 10(a)-(f)) at a number of discrete time-points. Highly aligned sarcomere formation is dependent on the biaxiality of the local stress state. Aligned sarcomere formation occurs in regions where the stress state is uniaxial in nature. In contrast, sarcomere structures do not occur in regions where the stress state is biaxial in nature. In addition, the computed maximum principal stress direction correlates closely with the computed direction of sarcomere alignment.

The design process and results presented according to the present embodiment constitute a unique method of combining computational approaches with tissue design and "bottom-up" construction of hPSC-derived heart tissue using surface marker-delineated heart cell populations. Embodiments of the present disclosure therefore advance previous microtissue contractility models by transitioning from an actinin-based model to a sarcomere based model specific to engineered cardiac tissue.

The framework described above is applicable to the design and study of engineered cardiac microtissue response. For example, the results from the model indicate that there is benefit in creating post geometries that induce uniaxial tension in the remodeled microtissues. Specifically, this occurs from the stresses that result from the stresses along aligned the axis of force. The expression of sarcomeric alpha actinin also was expressed uniformly (and correlated) to the areas and degree of stresses within the microtissues.

In general, to produce a cardiac tissue construct with homogeneous and highly aligned sarcomeric alpha-actinin structure, selecting a geometry that promotes maximal uniaxial tension forces is preferred. To design pathological tissues of graded levels, geometries that promote increasingly biaxial tension forces could be designed with the intent of promoting fibrotic growth in the regions of low uniaxial stresses.

In one embodiment, the preceding model may be employed in a method for determining conditions under which a cardiac tissue construct will be formed with a distribution and alignment of sarcomeres that closely resembles, or approximates, that of a pre-selected remodeled geometry and a pre-selected distribution of sarcomeres. The method includes providing an initial set of geometrical boundary conditions associated with a microfabrication platform (such as the initial geometrical properties of posts that are provided within the microfabrication platform), and properties and relative quantities of components from which the cardiac tissue construct is to be formed (such as an initial quantity, and viscoelastic properties, of the collagen, cardiomyocytes and fibroblasts). These initial conditions are then employed to calculate, as a first iteration, a steady-state estimate of remolded geometry and the sarcomere distribution in the resulting remodeled cardiac tissue construct. This estimate is compared with the pre-selected geometry and distribution of sarcomeres in order to assess the mismatch between the estimate and the pre-selected geometry. The one or more parameters are then further varied, optionally in an amount dependent on the mismatch, and a new estimate, and mismatch, are calculated. This process is repeated until a sufficient degree of convergence has been achieved. The process of varying the parameters in order to achieve convergence may be performed according to known methods, such as methods based on those disclosed in "Numerical Recipes in C" [Brian Flannery, Saul Teukolsky, and William Vetterling, Numerical Recipes in C: The Art of Scientific Computing, William Press, Cambridge University Press (October 1992)].

After having achieved sufficient convergence, the resulting parameters may be employed to produce the suitable microfabrication platform, and to select the appropriate quantities of the components. The microfabrication platform may then be employed to produce a cardiac tissue construct having a geometry and sarcomere distribution resembling the preselected criteria.

By employing the present computational approaches to predict self-organization of multiple cells in a matrix, increasingly complex structures can be engineered, not just of heart tissue, or vascular tissue, but combinations of tissues in one system to study inter-tissue interactions.

Experimental Validation of Self-Organizing Heart Cells Inducing Uniaxial Stress-Mediated Sarcomeric Alignment in Cardiac Microwire In order to empirically validate the predictions of the aforementioned model, substrates was generated as before, but of the geometries which modeled in FIG. 11(a). Disc inserts (circular cutout from the molded substrate sheet to fit within a well of a 24-well multiwall plate) were designed containing the recessed arrayed microwells, and were placed inside of a universal 24-well TCTP multiwell plate (FIGS. 11(b) and (c)). rR heart cells were suspended in a fully-defined non-polymerized collagen matrix, applied over the microfabricated substrate, and centrifuged to force the cells into the recessed microwells. The excess collagen was removed and the remaining pockets of cell-laden collagen were polymerized.

Cells were observed to begin to extend filopodia and remodel the surrounding collagen matrix, and within 3 days the microtissues had formed and hit a plateau in morphology. Along with time in culture, it was observed that higher concentrations (2.2 mg/mL-3 mg/mL) of collagen prolonged the time and extent of microtissue remodeling, as did lowering the input cell density.

As predicted by the aforementioned model, overall sarcomere expression in the cardiac microwire microtissue was observed to be high and spatially homogeneous as revealed by immunostaining for cardiac sarcomeric proteins alpha-actinin and cTnT (FIG. 1(e)) in comparison to the BITF microtissue (FIG. 1(d)). As also determined by the model, highly aligned sarcomeric expression correlated to areas of high stress. Additionally, in areas where the model predicted tension-induced alignment due to high uniaxial stress, elongated and oriented cell alignment was observed parallel to modeled localized tension force lines. Overall cell elongation was significantly higher in the cardiac microwire system, due to the uniaxial tension forces acting on the cells additional to the remodeled aligned collagen architecture (FIG. 1(h)). Additionally, cells in cardiac microwire demonstrated higher alignment compared to cells in BITF microtissue (FIG. 1(h)). These results closely resemble the morphology profile of earlier studies on 2-D collagen-deposited glass substrates (FIG. 1(g)).

As a next step, a cardiac microwire was generated to be composed of hESC-derived heart cells and similar remodeling characteristics and protein expression were observed. To ensure that the cells were aligning the collagen-based ECM after three days of remodeling, the cardiac microwire was assessed using the LC-PolScope quantitative birefringence imaging system. In the PolScope images (FIG. 1(f)), the shade of the pixel determines the orientation angle of the fibrillar collagen. It was confirmed that the fibrillar collagen within the cardiac microwire was indeed remodeled and aligned in parallel to the longitudinal axis of the cardiac microwire.

Functional Maturation of Cardiac Microwire

Excitation threshold (ET) and maximum capture rate (MCR) were shown to improve significantly when hESC-derived heart cells were dissociated from their original aggregates and cultured as cardiac microwire (FIGS. 2(a) and 2(b)). MCR improved even further when the cardiac microwires were electrically point stimulated with a biphasic square wave pulse for three days. This was achieved by integrating the two flanking posts within the cardiac microwire microwell with platinum wire electrodes to provide electrical point stimulation capability, as described above (and shown in FIGS. 11(a) and (b)).

Cardiac microwires had an intrinsic spontaneous beating frequency of ~1 Hz which is an expected baseline for human cardiomyocytes. Using drugs of known effects, the cardiac microwire was perturbed and optically mapped their response (transmembrane AP and intracellular calcium transient) using voltage- and calcium-sensitive dyes, respectively.

Addition of Epinephrine (0.1 μg/mL), an adrenergic neurotransmitter, to the cardiac microwires increased the AP activation rate relative to the baseline, while adding increasing concentrations of Lidocaine (2 μg/mL and 4 μg/mL), an antiarrhythmic drug, reduced and nearly abolished activation (FIG. 2(c)). Adding Verapamil (0.25 μg/mL), an L-type $Ca^{2+}$ channel blocker, reduced the amplitude of calcium waves in cardiac microwire relative to the baseline, and subsequently supplementing with Epinephrine (0.1 μg/mL) increased the rate of calcium transients (FIG. 2(d)).

Conduction velocities of a cardiac microwire generated with ~75% CM (on par with condition B), in the absence of a scaffold, were recorded and compared to healthy and diseased conduction velocities of the human heart (FIG. 5). Cardiac microwire conduction velocity (47.4±12.4 cm/s) was found to be comparable to that of a healthy human heart (46.4±2.7 cm/s). Other cardiac microwires, composed of 25% CM and 50% CM, showed non-synchronous and/or weak action potentials. Additionally, cardiac microwires composed of higher non-myocyte percentages (e.g. higher than approximately 25%) remodeled extensively and snapped due to excessive loads. CMW composed of 100% CM did not remodel to allow for well integrated tissue and so also did not contract synchronously. Action potentials were not able to traverse down length of tissue. It has been found that cardiac microwires composed of 75% CM and 25% non-CM (FB) generate the most structurally sound tissues and as a result, most functional in terms of electrophysiology (conduction velocity).

The dynamics of AP propagation in cardiac microwire were also studied and manipulated. Normal AP propagation in cardiac microwire initiates in the loop of one end, converges, traverses down the length of the wire, and then diverges at the neck of the opposite loop (FIG. 2(e) (top set)). In some cases, it was possible to observe the AP propagation dynamics perturbed by physical deformities similar to reentrant waves in arrhythmias caused by scar formation. This conduction block was observed at the neck of the loop as can be seen in FIG. 2(e) (bottom set).

It was also determined that AP propagation directionality in cardiac microwire could be manipulated using electrical point stimulation. Starting with cardiac microwire with spontaneous AP traversing from left to right, the AP direction was reversed by electrically pacing from the right side (FIG. 2(f)).

A reentrant wave was modeled on a fibrillating heart by manipulating the geometry of the microtissue. Cardiac microwires were generated using a circular substrate to create a ring of tissue mimicking a reentrant wave during fibrillation (FIG. 2(g)). Electrophysiological assessment revealed spontaneous infinite loop-like cycles of AP propagation traversing the ring. It was observed approximately one third of total cardiac microwire rings generated were able to spontaneously undergo and sustain such reentrant waves after 1 week of remodeling.

According to example implementations of the present disclosure, cardiac microwires may be formed with conduction velocities that are measured on par with that of a healthy adult heart, and with increased gene expression levels of key cardiac maturation markers, including genes implicated in sarcomere structure, as well as ANF and BNP, which increase during the fetal heart gene program where organogenesis commences [20]. Example embodiments disclosed herein thus demonstrate the maturation of hPSC-derived cardiomyocytes, through self-organizing cell and ECM interactions between fibroblasts, type 1 collagen, and cardiomyocytes in bulk 3-D tissue.

Alternative Construct Geometries for Investigating Pathologies with Cardiac Microwires Designing, simulating, and testing other useful diseases tissue geometries, such as reentrant waves during ventricular fibrillation may provide insight into therapies. It may also be provoking to further expand to a bio-chemo-electro-mechanical model which could integrate biochemical signaling linked to ion-channel-based electrical activity driven by dynamic contractile forces. Currently, there are no computational models that link biochemical signaling, electrophysiological activity, and mechanical outputs together. With these types of HCS platforms, it is possible to create data to begin to inform these types of models. By screening a panel of input compounds and determining their effects on electrophysiology and contractility, one can build the bases for these types of models. Specifically, by generating dose curves for a variety of ligand-receptor interactions that are known, and by observing the resulting effect on cardiac function, one can map the effects of growth factor stimulation to functional response. One can then develop a model of how some of these functional changes can be modulated by manipulating certain pathways specific to cardiomyocytes.

Cardiac microtissues generated in a ring-type format can be a surrogate for re-entrant waves and can be used to model arrhythmias. Examples provided herein demonstrate the capability of initiating spontaneous reentrant waves characteristic of arrhythmias, and the ability to abolish such arrhythmias with either electrical stimulation or biochemical factors. In some embodiments, biaxial cardiac tissue constructs can be generated to promote low levels of localized CM development, in order to promote conduction block. In other embodiments, local ablation, such as laser ablation, could also be used to remove local regions of normal cardiac microtissues to kill cells in a small region, in order to prevent conduction.

The preceding embodiments involving the generation of synthetic pathologies in cardiac tissue constructs (such as the reentrant wave-based arrhythmia model) could be employed, for example, in screening of drug candidates, or other compounds or therapeutics of interest. For example, such cardiac tissue constructs could be employed to screen a panel of factors, such as factors which may help to slow down the activation propagation, and thus potentially abolish the reentrant nature of the conduction. While this example embodiment relates to the development and/or screening for anti-arrhythmogenic drugs, it is to be understood that cardiac tissue constructs exhibiting synthetic pathologies could be employed for a wide range of uses, including, but not limited to, drug screening.

Dependence of Input Population of NKX2-5+ and CD90+ Cells on Tissue Morphogenesis in Cardiac Microwires hESC-derived heart cells were sorted in order to generate tissues with specific input populations consisting of cardiac myocytes and fibroblasts. The cardiac differentiation protocol was applied to an NKX2-5-GFP reporter hESC line that contains the EGFP cDNA inserted into the NKX2-5-GFP locus of HES3 hESC [1, 9]. At the end of the differentiation protocol on day 20, the aggregates were dissociated (FIGS. 13(a) and (b)) and sorted using Flow Activated Cell Sorting (FACS) (FIGS. 16(a) and (b)).

Cardiac microwires of specific cardiomyocyte to fibroblast ratios and control aggregates of the same ratios were generated (FIG. 3(a)). A control set of non-dissociated hESC-cardiomyocyte aggregates were also maintained. Cardiac microwires were generated as previously described, and microtissue aggregates were generated in the AggreWell system.

Both the cardiac microwire and aggregate microtissues were cultured over seven days Familiar remodeling kinetics were observed compared to other experiments described herein, however, there were clear differences in tissue morphology between the tissue composition conditions. As the composition percentage of CD90+(FB) increased, a tighter, and more integrated tissue morphology under higher tension was observed. Many of the cardiac microwire consisting of 75% CD90+ cells snapped from failure due to the high tension forces exerted by the cFB. Additionally, the majority of 75% CD90+ cardiac microwire did not display synchronous contractions, and those that did exhibited very low spontaneous activation rates (less than 1 Hz).

In the condition with 100% NKX2-5+ cells, cardiac microwire formed unstable tissue with minimal cell-cell and cell-ECM integration and were undergoing asynchronous contractions (FIG. 3(b) and FIG. 13 (a-c)). Globular contracting aggregates, likely clonal populations of proliferating cardiomyocytes, separated by patches of collagen were observed throughout the cardiac microwire.

As the percentage of CD90+ cells decreased to 25%, however, the cardiac microwire took on a more robust architecture with synchronous contractions resembling in vivo-like tissue morphology (FIG. 3(c), FIG. 13(d,e)).

To determine the spatial localization of the fibroblast population within the tissues before and after tissue generation, the tissues were stained and imaged for Vimentin. Fibroblasts in non-dissociated hESC-cardiomyocytes aggregates (FIG. 3(d)) in many cases displayed spatial heterogeneity among cardiomyocytes. In the engineered aggregates and cardiac microwire, however, fibroblasts and cardiomyocytes displayed spatial homogeneity. Engineered aggregates and cardiac microwire composed of 75% NKX2-5+ and 25% CD90+ cells exhibiting a homogeneous spatial distribution of fibroblasts within cardiomyocyte cardiomyocytes are shown in FIGS. 3(e) and (f).

Gene Expressions of Cardiomyocyte Control and Maturation Markers Show Dilution Consistency of Input Cell Composition and Maturation Effects in Cardiac Microwires In order to determine further effects of tissue formulation on tissue development, gene expression of key cardiac maturation markers was examined in the engineered tissue after 7 days in culture. Control cardiomyocyte markers were first examined for determining dilution consistency of input cell composition. Conditions 'A', 'B', 'C', 'D' correspond respectively to 100, 75, 50, and 25 percent NKX2-5-GFP+ cells with the remainder consisting of CD90+ cells as per FIG. 3(a).

The NKX2-5 gene was the basis of initial cardiomyocyte sorting, and was used as both a control and a normalizing factor for measured cardiac-specific genes. As NKX2-5 is a cardiac transcription factor, negligible variations in mRNA levels were assumed within the cardiomyocyte population. As expected, NKX2-5 expression showed a decreasing trend with increasing dilution of cardiomyocyte in the engineered tissue (FIG. 4(a)). DDR2, a marker for fibroblasts, showed an increasing trend with increasing concentration of fibroblasts (FIG. 4(b)). Cx43, a common marker to both cardiomyocytes and fibroblasts showed consistently level trends. Cardiomyocyte marker expression (SIRPA, and cTnT) in both aggregates and cardiac microwire also remained consistently level after being normalized to NKX2-5 (FIGS. 4(d) and (e)).

The effects of maturation were then examined via a panel of genes including markers indicative of healthy cardiomyocyte maturation. Atrial natriuretic factor (ANF), secreted by the atria, and brain natriuretic peptide (BNP), secreted by the ventricle, are cardiac hormones that are involved in normal and diseased heart physiology [21, 22]. Increasing trends of ANF expression in cardiac microwires were observed relative to the control aggregates, especially in the 'B' condition (FIG. 4(f)). Significant increases were observed of BNP expression in cardiac microwire in both conditions 'A' and 'B' (FIG. 4(g)).

Expression levels of MYL2 (MLC2v) and MYL7 (MLC2a), genes specific to sarcomere structure, were both also observed to be higher in the 'B' condition for cardiac microwire. Although there were no significant differences in MYH6 (α-MHC) expression between conditions, MYH7 (β-MHC) expression was significantly higher for both 'B' and 'C' conditions. The ratio of MYH7/MYH6 was found to be increased in cardiac microwire for all conditions except 'A'.

The preceding gene expression results indicate that the largest increase in levels of maturation occurred in CMW composed of 75% CM and 25% FB, suggesting that a first step in generating adult-like tissue may involve the a cardiac tissue construct having a similar composition ratio. As noted above, other composition ratios, such as approximately 55-95% CM and 5-45% non-CM cells, may also be selected in order to generate cardiac tissue constructs that also demonstrate properties associated with maturation (or healthy heart function).

High Content Screening Using Cardiac Microwires

As noted above, some embodiments of the present disclosure may be well suited for applications in high content screening. In one example implementation, a screening platform may employ a 96-well plate footprint, with one or more cardiac microtissues within each well (in some implementations, it may be useful or beneficial to include more than one cardiac tissue construct per well). In some implementations, the cells may be seeded such that there is limited cell waste.

Measurable outputs from a CMW include electrophysiological measurements, force of contractility measurements, as well as common immunostaining outputs which can be captured, for example, with a confocal microscope.

Additionally, media samples (supernatant of cell-conditioned media) can be obtained to observe secreted factors during screening. In general, embodiments of the present disclosure provide a true HCS platform with multiple outputs (protein expression, force of contraction, conduction velocity, excitation threshold, maximum capture rate, action potential duration, rate of contraction, duration of contraction, gene expression, and secreted soluble factors) not found in conventional platforms, while retaining the low cell numbers required—similar to that of conventional monolayer platforms (25,000-100,000 cells per tissue/well which comes out to ~$2.5\times10^6$-$10\times10^6$ cells per 96-well plate).

In one example implementation of a screening application, seeding could be performed with a multichannel pipette. The relative concentrations of the cell components of the cardiac tissue construct could be chosen to be similar to the conditions found to be suitable for mimicking the behaviour of a healthy human heart (for example, such as approximately 75% CM and 25% non-CM, or other suitable ratios as described above). Tissues would be allowed to remodel for a suitable time duration, such as one week (with or without electrical stimulation, starting after several days). Finally, test factors would be applied after remodeling (for example, after day 7) and allowed to take effect. The assay would be conducted after a suitable time period, such as 4 days Immediate effects of compounds could also be tested by determining a baseline reading, applying a compound, and then measuring changes in tissue response. After live cell measurements have been taken, tissues can be fixed, permeabilized, and immunostained for imaging. Conditioned media samples could also be taken daily for secreted factor analysis. For example, levels of ANF, BNP, or cTnT can be detected as biomarkers of cardiac disease. The entire process (both seeding and imaging) could be automated by adapting the system to a robotic handler.

Example 1: Materials and Methods

The following examples are presented to enable those skilled in the art to understand and to practice embodiments of the present disclosure. They should not be considered as a limitation on the scope of the present embodiments, but merely as being illustrative and representative thereof.

Atomic Force Microscopy of Collagen Deposited Slides

The data were collected on a Nanoscope IIIA Bioscope AFM. Tapping mode imaging was used in air using a TESP cantilever at a drive frequency of ~320 KHz, at a scan rate of 1 Hz (as a 512×512 pixel image) using the Nanoscope software version 5.30A.

Preparation and Seeding of Collagen Deposited Glass Substrates

Samples from collaborators at FibrAling Corporation are received loaded into tubes from with an uncoated glass border at the grasping end. Using clean forceps/tweezers, the glass chips are removed by their top grasping edge. Using the light reflectance to choose the collagen coated side, glass chips are placed in sterile tissue culture plates making note that fibril (coating) direction is parallel to collagen-glass border.

Glass chips are dipped into Dulbecco's Phosphate Buffered Saline (DPBS) for 20 seconds (Sigma D8537). They are then immediately rinsed in DI water using a gentle rotation motion for 5-10 seconds. They are then gently blow dried with clean, dry nitrogen or air and then immersed in 70% ethanol for a minimum of 1 hour to sterilize. After rinsing the sample in DPBS, slides are allowed to sit in culture media for 15 minutes before being seeded with cells. Cells are suspended in culture media at desired density and pipetted onto slide in a tissue culture plate. The cells are given 2 days to adhere before exchanging culture with fresh media.

Isolation of Rat Neonatal Cardiomyocytes

Rat neonatal cardiomyocytes were isolated as previously reported (Dengler et al., 2011). Briefly, hearts were isolated from 1- to 2-day old neonatal Sprague Dawley rats using protocol approved by the University of Toronto Committee on Animal Care. Rat hearts of 1 to 2 litters of approximately 13 pups/litter were aseptically excised and placed in cold Hanks balanced salt solution (HBSS, Sigma), washed several times with HBSS and quartered.

Quartered hearts were then incubated overnight at 4° C. in a 0.06% w/v solution of Trypsin (Gibco) in HBSS on an orbital shaker at 50 RPM (Labent Orbit LS, Mandel). After 14-16 hours, hearts were washed with cardiomyocyte culture medium (high glucose [4.5 g/L] Dulbecco's Modified Eagle Medium (DMEM) with L-glutamine (Gibco) supplemented with 10% fetal bovine serum (FBS, Gibco), 1% penicillin/streptomycin (Gibco) and 1% N-2-hydroxyethyl-piperazine-N-2-ethane sulfonic acid (HEPES, Gibco)) and subjected to a series of five digests (8 minutes, 37° C., 70 rpm) in a 0.1% (w/v) solution of collagenase type II (Worthington) in HBSS. The supernatant of each digest was collected, centrifuged (5 minutes, 750 rpm) and resuspended in cardiomyocyte medium. Cells were pre-plated for 60 minutes on tissue culture polystyrene (TCP) T75 flasks (BD Flacon) to enrich for cardiomyocytes (non-adherent cells). The supernatant was collected, and cell number was determined via trypan blue (Gibco) exclusion.

Cardiac Differentiation of Human Embryonic Stem Cells

Cardiac differentiation of human Embryonic Stem Cells was carried out as reported previously (Celine L Bauwens et al., 2011). In this study, the HES2 (ES Cell International) hESC line was used. The hESC were maintained and expanded as described previously [23]. Briefly, HES2 cells were passaged (up to 5 times) on mouse embryonic feeders (MEF) for 6 days in HES2 maintenance media (80% DMEM/F12, 20% KOSR, 20 ng/mL bFGF, 0.5% P/S, 1% NEAA, 1% BME), media was changed daily. Cells are maintained in normoxia at 37° C. in a 5.0% $CO_2$ atmosphere. The cells were then trypsinized along with MEFs and plated onto Matrigel™ (diluted at 1:30) coated plates at a split ratio of 1:3 for MEF depletion. After two days of MEF depletion, HES2 cells were again trypsinized and seeded into AggreWells manufactured in-house to form hEB. The hEB were generated using 400 μm microwell PDMS inserts cast from a silicon master mould. The inserts were cut and glued into 24-well tissue culture plates and then sterilized using ethanol. The microwells were then coated with 5% Pluronic™ Acid for at least an hour and washed with PBS before cell seeding.

A single cell suspension of aggregation media containing base media and T0 cytokines supplemented with ROCK inhibitor Y-27632 was then seeded into the wells and allowed to aggregate overnight after centrifuging at 200 g. Cells are maintained in hypoxia at 37° C. in a 5.0% $CO_2$ and 5.0% $O_2$ atmosphere. After 24 hours, hEB were formed and aggregation media was exchanged for T1 media. On day 4, hEB were removed from AggreWells and placed in Low cluster 6-well plates (NUNC). Corresponding media for T4, T8, T12 was freshly made and exchanged. On T12, cells were returned to normoxia at 37° C. in a 5.0% $CO_2$ atmosphere. Media was replaced every 8 days onward.

Generation, Cultivation, and Imaging of Cardiac Microtissues

Either rat neonatal cardiomyocytes or hESC-derived cardiomyocytes suspended in a collagen mastermix and seeded into cardiac microtissue wells at a density of $0.5\times10^6$ cell/mL. Microwell substrates were prepared by sterilizing with ethanol, washing and coating with 5% Pluronic™ Acid for at least an hour each. While coating, rat neonatal cardiomyocytes and/or hESC-derived cardiomyocytes are prepared. Aggregates from hESC-cardiomyocyte differentiation are put in Collagenase for 1 hour with DNAse in the incubator. Aggregates are then immersed in 0.25% Trypsin for 5-10 minutes with DNAse. Aggregates are then immersed in STOP solution (50% FBS and 50% DMEM F12) and triturated with a 20-gauge syringe 10 times. Once aggregates are single cells, they are immersed in STAIN solution (10% FBS and 90% DMEM F12) and counted. The collagen mastermix is prepared by combining the following: 10× M199 (GIBCO), Glutamax (GIBCO), Collagen 1 (3.66 mg/mL) (BD), Glucose (0.3 g/mL) (GIBCO), NaOH (SIGMA), NaHCO3 (0.075 g/mL) (SIGMA), Hepes (GIBCO), GFR Matrigel™ (BD), ddH20 at appropriate ratios for desired collagen concentrations. The collagen mastermix is constantly kept on ice under 4 degrees Celsius to prevent premature crosslinking. Finally, pipet 500 uL of mastermix into each well (of 24-well plate) and centrifuge at high speed (300 g) to eliminate bubbles. Maintain centrifuge at ice-cold temperature. Prepare cell-laden collagen (additional 250 uL per well) and pipet/mix into well to bring final cell density to 500,000 cells per well (final volume in each well should be 750 uL). Centrifuge entire plate (200 g) to force cells into microwell recessions. Carefully and slowly aspirate excess cell-laden collagen in each well to leave pockets of cell-laden collagen in each microwell. Place entire plate into normoxic incubator for 15 minutes. After 15 minutes, add 1 mL of cell culture media slowly as to not disrupt the polymerized collagen microtissues. Exchange media every 4 days. Microtissues should remodel between 1-3 days depending on input cell composition. Imaging of microtissues can be done in situ. Samples can also be fixed, permeabilized, and stained inside the microwells and imaged using a fluorescence microscope.

Electrical Stimulation and Functional Analysis of Cardiac Microwires

For electrical point stimulation, microwells were embedded with 0.005" platinum wires (99.99% purity, A-M Systems Inc.) and hooked up to a commercial stimulator (Model S88X Grass, Astro-Med® Inc.). After 72 hours of cultivation without electrical stimulation, the microtissues to be stimulated were stimulated with biphasic, square pulses, 1 ms in duration, threshold amplitude of 6V (field strength of 6 V/cm) and frequency of 1 Hz for the remainder of cultivation (4 days). The stimulation voltage was selected to induce synchronous construct contractions. Constructs were held in place within the PDMS substrate 0.1 mm stainless steel Minutiens pins (Austerlitz) were used to ensure the microtissues did not slip out.

Tissue function was established by measuring excitation threshold (ET), the minimum voltage required to pace the tissue simultaneously, and maximum capture rate (MCR), the maximum stimulation rate at which the construct can be induced to beat simultaneously, at 7 days after cell seeding. Tissue constructs or cardiomyocyte aggregates were individually placed between a pair of carbon electrodes in stimulation chambers (autoclaved before use). ET (V/cm) was measured by stimulating the tissue with square pulses of 2 ms pulse width at a frequency of 1 or 2 Hz and gradually increasing the output voltage of the stimulator until >80% of the tissue was beating synchronously with the stimulator output. MCR was measured by setting the output voltage at 12 V, and increasing frequency until >80% of the tissue was no longer synchronously beating with the driving signal. All measurements were taken using an Olympus 1X2-UCB inverted fluorescent microscope housed in an environmental chamber (SolentScientific) maintained at a temperature of 37° C., and equipped with a Retiga camera (QImaging).

Flow Cytometry

Aggregates are dissociated using collagenase treatment and Trypsin and immediately fixed with 4% paraformaldehyde (PFA) overnight at 4 degrees Celsius. They are then permeabilized at room temperature with 100% methanol for 2 minutes. Primary antibody is added after a 2% HF wash. It is then incubated at room temperature for 20 minutes. Next, the sample is washed with HF, and secondary antibody is added for another 20 minutes at room temperature. Lastly, the sample is washed again and is ready for flow cytometry analysis. The samples were always kept on ice before measuring on the flow cytometer.

Immunostaining and Image Analysis of Cardiac Microwires

Microtissues were washed with PBS and fixed for 24 hours with 4% PFA at 4 degrees Celsius. They were then permeabilized in 0.1% Triton X in blocking solution (Normal Donkey Serum). Primary antibody was then added for 3 days at 4 degrees Celsius. Lastly, the microtissues were washed three times and stained with the appropriate secondary antibody (AlexaFluor series) and with DAPI for nuclear staining, for one day overnight in the fridge. Each incubation step was performed on a rocker table. Before imaging, the sample was washed three times and resuspended in 2% HF. Samples were imaged using a confocal microscopy (FV1000 laser scanning confocal; Olympus). All image analysis was done using custom macros built in ImageJ (cell alignment and elongation analysis, and total cell marker expression enumeration).

Optical Mapping of Cardiac Microwires

For optical measurements, microtissues were stained with 5 mM of Di-4-ANEPPS (Invitrogen, Carlsbad Calif.) voltage-sensitive dye for 20 minutes, followed by 3 washouts with fresh warm Tyrode's solution (Sigma-Aldrich) adjusted to pH 7.4. The temperature was kept constant at 37° C. using a block incubator. Dye fluorescence was recorded using a microscope mapping system (Ultima, Scimedia, Tokyo Japan). The system included a CMOS camera with a 1 cm sensor (100×100 pixel) attached to a custom-built microscope using PLAN APO objective and condensing lenses (Leica Microsystems GmbH, Wetzlar Germany), giving a magnification of 1.5×. The spatial resolution was 63 µm/pixel. The fluorescence was excited using a Xenon light source (Moritek Corp. Japan) and a 530 nm green filter (Semrock, Rochester N.Y.) and the emission signal was long pass filtered using a 610 nm red filter. Tissue constructs were point stimulated at 1000-ms cycle length using a bipolar electrode made with 2 fine silver wires (AWG#32) inserted in a large stainless steel needle mounted on a micromanipulator. Spontaneous tissue beating was also recorded, in addition to responses to frequency sweep from 1 to 5 Hz. Local activation times were measured at the peak of dF/dT for each pixel. Activation maps were constructed for a selected beat.

Conduction velocity was calculated at each location using activation times of 9 neighbouring sites. Conduction velocity values from all sites were used to calculate the average conduction velocity across the construct surface; minimum and maximum values were also noted. Phase contrast images of microtissue surfaces were taken prior to optical mapping, to correlate tissue architecture geometry with conduction velocity. Concentrations of drugs used applied as indicated. Stock solutions were prepared as recommended by vendors: Epinephrine at 1:1000 (Hospira), Lidocaine at 1:1000 (Hospira), and Verapamil at 1:1000 (Sandoz).

Example 2: Experimental Studies of Tissue Constructs Formed in Microwell-Based Microtissue Platforms with a Ramped Base Investigation of Tissue Thickness, Uniformity, Re-Modeling Time, and Tissue Vitality Using Mouse Myoblast Cells Using a mouse myoblast cell line called C2C12, the following parameters were investigated: tissue thickness uniformity, re-modeling time, and the vitality of the tissues. The reason for using the C2C12 cell line was because they proliferate relatively quickly and also have the ability to differentiate into contractile myotubes that are responsive to electrical stimulation. To get a better understanding of the C2C12 cell line, three separate cultures were counted every day for four days. The results are displayed in FIG. 28.

By seeding 40 uL of the cell/collagen-matrix in six different concentrations, the remodeling time and the tissue thickness uniformity was mapped over 3 days. The table in FIG. 29 outlines the six different cell/collagen-matrix conditions. In the table shown in FIG. 30, the largest deviation from the mean thickness is reported in a percentage value for each day in each condition.

From the table shown in FIG. 30, it is clear that the tissue uniformity in all conditions did not seem to deviate from the mean on a significant level. To provide a different perspective, a plot was created for the day 1 measurements, plotting the thickness for all four corners for each condition, which is presented in FIG. 31.

The remodeling time of the tissue for the different conditions was also investigated and the data is presented below in FIG. 32. Generally, lower collagen concentrations and higher cell densities resulted in faster remodeling times.

Additionally, studies were performed to assess whether or not the cells in the tissues were surviving and if so, for how long. A live/dead stain was performed on each of the conditions at day 1 and day 2. The images are presented below in FIGS. 33(a) and (b), which show (a) live and (b) dead staining images.

It is clear from the images shown in FIG. 33 that significant cell death occurred between day 1 and day 2. Without intending to be limited by theory, it is hypothesized that this occurred because the tissues were over 300 micrometers in thickness, and thus could not allow for proper diffusion of nutrients to the entire tissue, leading to cell death. Once potential solution to overcome this problem would be to reduce the amount of cells being seeded into each well (it should be noted that the C2C12 cells being used proliferate at very high rates thus contributing to the over population of cells).

Figure 35B:
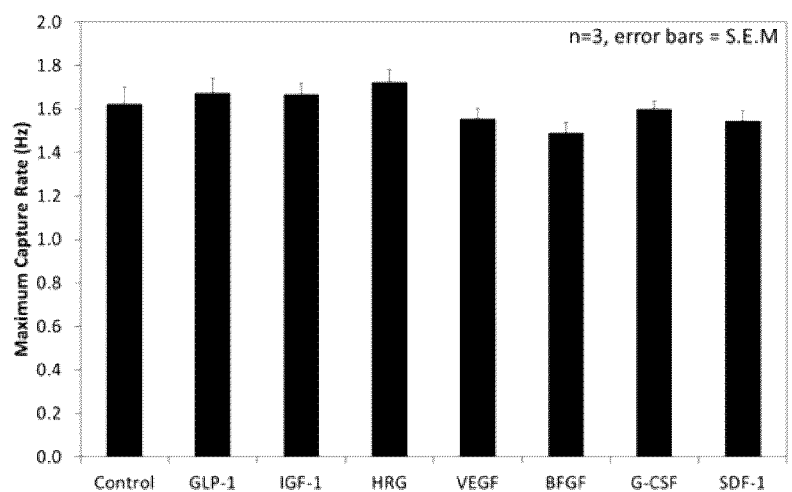

A preliminary screen was also performed in order to determine the maturation effect of growth factors. The effect of seven growth factors (listed in the table in FIG. 34) on two electrophysiological parameters (ET and MCR) were tested. The results of these studies are shown in FIG. 35. It was observed that IGF1 and HRG reduced ET compared to the control condition. The challenge with higher level functional readouts with in vitro models is that further analyses need to be done to determine the mode of action. In order to determine the mechanism of IGF1 and HRG, other functional parameters as well as molecular readouts over a time course will be investigated.

As shown in FIGS. 36(a) and (b), arrhythmia models can be created using circular-shaped substrates. The goal was to mimic tachycardia by mimicking scar formation in vitro. Cells were seeded in the same way as before and allowed to remodel to create ring-shaped tissues. Assessment revealed spontaneous infinite loop-like cycles of activation propagation traversing the ring; one cycle is shown. Signal tracings show multiple cycles. (E) Normal rhythm was observed in $CMW_{circ}$ after defibrillation. Electrical field stimulation of 10 V was used to defibrillate arrhythmias in CMW-circular geometries to normal rhythm Signal tracings show multiple cycles. Initiation site in blue (I*) indicates starting location of impulse propagation and termination site in blue (T*) indicates final location of impulse propagation.

Measuring Force of Contraction with the Cardiac MicroRing System—Drug Response

In the present example, microwells with ramped support structures having retaining structures provided thereon, as described above, were seeded at 0.1×10^6 cells per tissue in 2.0 mg/mL Collagen 1. Tissues remodeled over two weeks along with contractile force as measured using the microcantilevers in the system. After two weeks, tissues were introduced with drugs in 100% DMSO vehicle. Final concentrations applied to tissues were ensured to be less than 0.01% DMSO to ensure non-toxic effects. Concentrations were mixed separately in a 96 well plate and applied to the tissues. Measurements were taken after 15 minutes of incubation with the drug at 37 degrees Celsius.

FIGS. 37 and 38 show the measured relative contractile force (relative fold-change) with respect to the maximum contractile force control (FIG. 37) or no-drug control (FIG. 38). Videos of approximately 10 seconds were recorded and analyzed offline using ImageJ for each condition. As can be seen in FIG. 37, the contractile force was observed to increase over 2 weeks, and plateaued at approximately 1.5 weeks. Contractile force assays were conducted after the contractile force was plateaued to ensure no changes in contractile force due to tissue remodeling. As shown in FIG. 38, Nifedipine and Terfenadine were observed to reduce the contractile force (relative to control) with increasing concentrations.

Example 3: Example Designs of 96-Well Tissue Microfabrication System

The present example provides example designs that bring together the aspects of a 96 well tissue culture plate as well as a specific design in the bottom of each well, based on the ramped support embodiment shown in FIGS. 22(b)-(d) (example diameter approximately equal to 5.0-8.0 mm and depth approximately equal to 9.0-14.0 mm) The specific design encompasses a recessed well (for example, approximately 3.0-6.0 mm in diameter and approximately 0.5-2.0 mm deep) with a cone in the center (base diameter approximately equal to 2.0-3.0 mm and top diameter of approximately 1.0-2.0 mm and a height of approximately 0.5-2.0 mm) On top of the cone are two, cylindrical, posts (approximately 0.1-0.6 mm in diameter) that are separated by 2 mm (centre to centre).

As noted above, the purpose of the cone is to provide support to the remodeling tissue as well as aid the tissue to the base of the posts. This cone will prevent the tissue from fusing between the posts, thus forming a ring-shaped tissue.

In some illustrative and example embodiments, the posts may have a height of approximately 1.8-2.2 mm, while in other embodiments, the may have a height of 1.25-1.8 mm. In another example embodiment, the posts may have a height of approximately 0.5-1.0 mm, and each post may have an outward facing stabilizing protuberance (e.g. in the shape of a rectangular prism, for example, with dimensions approximately equal to 0.3 mm in height, 0.5 mm in length, and 0.3 mm in width). The latter design may be advantageous due to the presence of the stabilizing features that provide a hooking mechanism prohibiting further motion of the tissue construct, such that the tissue construct is not able to surpass the tops of the retaining structures. The tall posts will also serve as an amplification method of the post deflection during tissue contraction.

The posts may be fabricated such that deformation occurs at a detectible level during tissue remodeling. As noted above, a mechanical model of the posts can be employed to select suitable properties and dimensions of the posts.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

REFERENCES

1. Elliott, D., et al., NKX2-5(eGFP/w) hESCs for isolation of human cardiac progenitors and cardiomyocytes. Nature methods, 2011. 8(12): p. 1037-1040.
2. Burridge, P., et al., Production of de novo cardiomyocytes: human pluripotent stem cell differentiation and direct reprogramming Cell stem cell, 2012. 10(1): p. 16-28.
3. Zhang, J., et al., Extracellular Matrix Promotes Highly Efficient Cardiac Differentiation of Human Pluripotent Stem Cells: The Matrix Sandwich Method. Circulation research, 2012.
4. Xu, C., et al., Efficient generation and cryopreservation of cardiomyocytes derived from human embryonic stem cells. Regenerative medicine, 2011. 6(1): p. 53-66.
5. Zhu, W.-Z., B. Van Biber, and M. Laflamme, Methods for the derivation and use of cardiomyocytes from human pluripotent stem cells. Methods in molecular biology (Clifton, N.J.), 2011. 767: p. 419-431.
6. Lian, X., et al., Robust cardiomyocyte differentiation from human pluripotent stem cells via temporal modulation of canonical Wnt signaling. Proceedings of the National Academy of Sciences of the United States of America, 2012.
7. Kattman, S., et al., Stage-specific optimization of activin/nodal and BMP signaling promotes cardiac differentiation of mouse and human pluripotent stem cell lines. Cell stem cell, 2011. 8(2): p. 228-240.
8. Uosaki, H., et al., Efficient and scalable purification of cardiomyocytes from human embryonic and induced pluripotent stem cells by VCAM1 surface expression. PloS one, 2011. 6(8).
9. Dubois, N., et al., SIRPA is a specific cell-surface marker for isolating cardiomyocytes derived from human pluripotent stem cells. Nature biotechnology, 2011. 29(11): p. 1011-1018.
10. Kean, T., et al., Development of a peptide-targeted, myocardial ischemia-homing, mesenchymal stem cell. Journal of drug targeting, 2012. 20(1): p. 23-32.
11. Panáková, D., A. Werdich, and C. Macrae, Wnt11 patterns a myocardial electrical gradient through regulation of the L-type Ca(2+) channel. Nature, 2010. 466 (7308): p. 874-878.
12. Kurazumi, H., et al., The effects of mechanical stress on the growth, differentiation, and paracrine factor production of cardiac stem cells. PloS one, 2011. 6(12).
13. Kim, D.-H., et al., Nanoscale cues regulate the structure and function of macroscopic cardiac tissue constructs.

Proceedings of the National Academy of Sciences of the United States of America, 2010. 107(65a45732-3d8c-d790-2439-4587336d3efb): p. 565-635.
14. Feng, Y., X.-Y. Yu, and Y. Wang, Recent concepts for the roles of progenitor/stem cell niche in heart repair. American journal of cardiovascular disease, 2012. 2(1): p. 75-83.
15. Gupta, M., et al., Combinatorial polymer electrospun matrices promote physiologically-relevant cardiomyogenic stem cell differentiation. PloS one, 2011. 6(12).
16. Schaaf, S., et al., Human engineered heart tissue as a versatile tool in basic research and preclinical toxicology. PloS one, 2011. 6(10).
17. Sassoli, C., et al., Mesenchymal stromal cells affect cardiomyocyte growth through juxtacrine Notch-1/Jagged-1 signaling and paracrine mechanisms: clues for cardiac regeneration. Journal of molecular and cellular cardiology, 2011. 51(3): p. 399-408.
18. Badie, N., et al., Conduction block in micropatterned cardiomyocyte cultures replicating the structure of ventricular cross-sections. Cardiovascular research, 2012. 93(2): p. 263-271.
19. Radisic, M., et al., Functional assembly of engineered myocardium by electrical stimulation of cardiac myocytes cultured on scaffolds. Proceedings of the National Academy of Sciences of the United States of America, 2004. 101(0f46d10f-6651-b669-44de-45d102a88b81): p. 18129-18163.
20. Legant, W., et al., Microfabricated tissue gauges to measure and manipulate forces from 3D microtissues. Proceedings of the National Academy of Sciences of the United States of America, 2009. 106(25): p. 10097-10102.
21. Deshpande, V., R. McMeeking, and A. Evans, A biochemo-mechanical model for cell contractility. Proceedings of the National Academy of Sciences of the United States of America, 2006. 103(38): p. 14015-14020.
22. Cameron, V. and L. Ellmers, Minireview: natriuretic peptides during development of the fetal heart and circulation. Endocrinology, 2003. 144(6): p. 2191-2194.
23. Bauwens, C., et al., Geometric control of cardiomyogenic induction in human pluripotent stem cells. Tissue engineering. Part A, 2011. 17(a62ce53c-3184-a62e-579e-45203336718d): p. 1901-1910.

Therefore what is claimed is:

1. A microfabrication platform for forming a tissue construct, comprising:
   a microwell;
   a ramped support structure provided within said microwell, said ramped support structure comprising an annular ramped surface and an upper platform, wherein said annular ramped surface extends upwardly from a base of said microwell to said upper platform; and
   one or more retaining structures provided on said upper platform of said ramped support structure, wherein said one or more retaining structures are positioned to apply tension to a tissue construct within said microwell during formation of the tissue construct.

2. The microfabrication platform according to claim 1 wherein said one or more retaining structures comprise two retaining structures that are provided at a relative separation suitable for applying tension to the tissue construct within said microwell during formation of the tissue construct.

3. The microfabrication platform according to claim 1 wherein said one or more retaining structures comprise a single retaining structure for retaining a ring-shaped tissue construct.

4. The microfabrication platform according to claim 1 wherein at least one retaining structure includes a stabilizing feature for stabilizing the position of the tissue construct during its formation.

5. The microfabrication platform according to claim 4 wherein said stabilizing feature is provided at an intermediate location between an upper portion of said ramped support structure and a distal end of said retaining structure.

6. The microfabrication platform according to claim 4 wherein one or more of said retaining structures is configured as a cantilever, wherein a deflection of said cantilever is associated with an amount of tension in the tissue construct supported by the retaining structures.

7. The microfabrication platform according to claim 6 wherein a distal end of said cantilever extends beyond a position at which the tissue construct is stabilized by the stabilizing feature, such that deflection of said distal end is amplified.

8. The microfabrication platform according to claim 1 wherein said ramped support structure is integrally formed with said microwell.

9. The microfabrication platform according to claim 1 wherein said ramped support structure comprises a side wall having a conical shape.

10. The microfabrication platform according to claim 1 wherein said ramped support structure comprises a curved side wall.

11. The microfabrication platform according to claim 1 wherein said ramped support structure is configured to induce upward motion of a tissue construct formed within said microwell during a tissue remodeling process.

12. The microfabrication platform according to claim 1 wherein a volume of said microwell surrounding said ramped support structure is sufficiently large to contain an amount of unpolymerized matrix that is suitable for forming a tissue construct, without initially covering an upper portion of said ramped support structure with unpolymerized matrix.

13. The microfabrication platform according to claim 1 wherein said ramped support structure comprises an upper platform disposed above said base of said microwell, and wherein said one or more retaining structures are supported by said upper platform.

14. The microfabrication platform according to claim 13 wherein said one or more retaining structures are integrally formed with said ramped support structure.

15. The microfabrication platform according to claim 1 wherein said microwell comprises a side wall, and wherein at least a portion of said side wall is configured to direct liquid into a portion of said microwell surrounding said ramped support structure.

16. The microfabrication platform according to claim 15 wherein said side wall comprises a lower portion and an upper portion, and wherein said upper portion has a curved shape that is configured to direct liquid into said portion of said microwell surrounding said ramped support structure.

17. The microfabrication platform according to claim 1 wherein said one or more retaining structures includes two or more retaining structures, and wherein a blocking structure is provided between a portion of said two or more retaining structures, and wherein said blocking structure is configured to prevent the formation of tissue between the two or more retaining structures during the formation of the tissue construct.

18. The microfabrication platform according to claim 1 wherein said one or more retaining structures includes two or more retaining structures, and wherein said two or more retaining structures are positioned to produce substantially uniaxial tension within the tissue construct during its formation.

19. The microfabrication platform according to claim 1 wherein a surface of each retaining structure is coated with a poloxamer, wherein said poloxamer is suitable for maintaining relative motion between the tissue construct and the retaining structure during formation of the tissue construct.

20. The microfabrication platform according to claim 1 further comprising a pair of electrodes supported by said ramped support structure and having a relative spacing suitable for point stimulation of the tissue construct.

21. A microplate comprising a plurality of microfabrication platforms, wherein said plurality of microfabrication platforms are provided according to claim 1.

22. A method of forming a tissue construct using a microfabrication platform;
the microfabrication platform comprising:
a microwell;
a ramped support structure provided within the microwell, the ramped support structure comprising an annular ramped surface and an upper platform, wherein the annular ramped surface extends upwardly from a base of the microwell to the upper platform; and
one or more retaining structures provided on the ramped support structure, wherein the one or more retaining structures are configured to apply tension to a tissue construct within the microwell during formation of the tissue construct;
the method comprising:
dispensing, into the microwell, a cell-containing pre-polymerized matrix that is configured to form the tissue construct according to a remodeling process, wherein the pre-polymerized matrix is dispensed into a region surrounding the ramped support structure without contacting the one or more retaining structures; and
incubating the microwell for a time duration suitable for remodeling of the pre-polymerized matrix into the tissue construct, such that the tissue construct moves upwards along the ramped support structure during the remodeling process and is retrained in a ring geometry by the retaining structures.

23. The method platform according to claim 22 wherein the microwell comprises a side wall comprising a lower portion and an upper portion, and wherein the upper portion has a curved shape that is configured to direct liquid into said portion of said microwell surrounding said ramped support structure, and wherein the step of dispensing the pre-polymerized matrix into the microwell comprises:
dispensing the pre-polymerized matrix such that the pre-polymerized matrix contacts the upper portion of the side wall, such that the pre-polymerized matrix flows into the region surrounding the ramped support structure without centrifugation.

24. The method according to claim 22 further comprising:
during or after formation of the tissue construct, adding one or more drug candidates to the microwell; and
measuring a response of the tissue construct to the drug candidate.

25. The method according to claim 24 wherein the response is measured via optical mapping.

26. The method according to claim 24 wherein one or more of the retaining structures is configured as a cantilever, wherein a deflection of said cantilever is associated with an amount of tension in the tissue construct supported by the retaining structures; the method further comprising:
detecting the response via measurement of the deflection of one or more of the retaining structures configured as the cantilever.

27. A microfabrication platform for forming a tissue construct, comprising:
a microwell;
a support structure provided within said microwell, said support structure comprising an annular lateral surface and an upper platform, wherein said lateral surface extends upwardly and inwardly from a base of said microwell to said upper platform; and
two or more retaining structures supported by said support structure, wherein said two or more retaining structures are configured to apply tension to a tissue construct within said microwell during formation of the tissue construct;
wherein said lateral surface has a shape configured to raise the tissue construct from said well base while preventing tissue formation between said retaining structures during a tissue remodeling process.

28. The microfabrication platform according to claim 1 wherein at least one retaining structure comprises a proximal portion and a distal portion, wherein said distal portion is angled relative to said proximal portion.

29. The microfabrication platform according to claim 4 wherein at least one retaining structure comprises a proximal portion and a distal portion, wherein said distal portion is angled relative to said proximal portion such that said distal portion extends in an upward and outward direction relative to said proximal portion to form said stabilizing feature.

* * * * *